US005721139A

United States Patent [19]

Mather et al.

[11] Patent Number: 5,721,139
[45] Date of Patent: Feb. 24, 1998

[54] ISOLATING AND CULTURING SCHWANN CELLS

[75] Inventors: Jennie P. Mather; Ronghao Li, both of Millbrae; Jian Chen, Burlingame, all of Calif.

[73] Assignee: Genentech, Inc., South San Francisco, Calif.

[21] Appl. No.: 435,436

[22] Filed: May 10, 1995

[51] Int. Cl.⁶ .................................................. C12N 5/06
[52] U.S. Cl. ...................... 435/383; 435/368; 435/366; 435/363; 435/325; 435/384; 435/387
[58] Field of Search ............................ 435/240.1, 240.2, 435/240.3, 368, 366, 363, 325, 384, 389, 387

[56] References Cited

U.S. PATENT DOCUMENTS

| | | | |
|---|---|---|---|
| 4,443,546 | 4/1984 | Stemerman et al. | 435/240 |
| 5,082,670 | 1/1992 | Gage et al. | 424/520 |
| 5,147,790 | 9/1992 | Wilson | 435/70.3 |
| 5,326,699 | 7/1994 | Torishima et al. | 435/240.2 |

FOREIGN PATENT DOCUMENTS

| | | |
|---|---|---|
| WO 92/03536 | 3/1992 | WIPO. |
| WO 92/18627 | 10/1992 | WIPO. |
| WO 94/04560 | 3/1993 | WIPO. |
| WO 94/00140 | 1/1994 | WIPO. |

OTHER PUBLICATIONS

Needham, L.K., "The Journal of Neuroscience," vol. 7(1), pp. 1–9, Jan. 1987.

Ohashi, K. et al., "The Journal of Biological Chemistry," vol. 270(39), pp. 22681–22684, Sep. 1995.

Stewart, H.J.S. et al., "Journal of Neuroscience Research," vol. 30(2), pp. 346–352, Oct. 1991.

Eccleston, P.A. et al., "Developmental Biology," vol. 124(2), pp. 409–417, 1987.

Zhang, B.T. et al., "Journal of Neuroscience Research," vol. 41, pp. 648–654, 1995.

Tong, Z.B., "Yokohama Igaku," vol. 46(2), pp. 111–117. Japanese original plus English translation, 1995.

Sigma Cell Culture Catalogue & Price List, pp. 46, 49, 50, 62, 63, 68, and 70, 1994.

Bellosta et al., "The Receptor Tyrosine Kinase ARK Mediates Cell Aggregation by Homophilic Binding" *Molecular & Cellular Biology* 15(2):614–625 (Feb. 1995).

Brockes, "Assay and isolation of glial growth factor from the bovine pituitary" *Methods in Enzymology* 147:217–225 (1987).

Brockes et al., "Glial growth factor-like activity in Schwann Cell tumors" *Annals of Neurology* 20:317–322 (1986).

Brockes et al., "Purification and preliminary characterization of a glial growth factor from the bovine pituitary" *Journal of Biological Chemistry* 255(18):8374–8377 (1980).

Brockes et al., "Studies on cultured rat schwann cells. I. Establishment of purified populations from cultures of peripheral nerve" *Brain Research* 165:105–118 (1979).

Brummendorf et al., "Axonal Glycoproteins with Immunoglobulin—and Fibronectin Type III–Related Domains in Vertebrates: Structural Features. Binding Activities and Signal Transduction" *Journal of Neurochemistry* 61(4):1207–1219 (1993).

Bunge, "Expanding roles for the Schwann cell: ensheathment, myelination, trophism and regeneration" *Current Opinion in Neurobiology* 3:805–809 (1993).

Collier et al., "Schwann Cells as a Source of Neurotrophic Activity for Dopamine Neurons" *Exper. Neurol.* 124:129–133 (1993).

Colombo et al., "Localization of Growth arrest–specific genes on mouse Chromosomes 1, 7, 8, 11, 13, and 16" *Mammalian Genome* 2:130–134 (1992).

Dahlback et al., "High molecular weight complex in human plasma between vitamin K–dependent protein S and complement component C4b–binding protein" *Proc. Natl. Acad. Sci. USA* 78 (4):2512–2516 (Apr. 1981).

Dai et al., "Molecular Cloning of a Novel Receptor Tyrosine Kinase, tif, Highly Expressed in Human Ovary and Testis" *Oncogene* 9:975–979 (1994).

Esmon, "The Protein C Anticoagulant Pathway" *Arteriosclerosis and Thrombosis* 12 (2):135–145 (Feb. 1992).

Ferrero et al., "Expression of a Growth Arrest Specific Gene (gas–6) During Liver Regeneration: Molecular Mechanisms and Signalling Pathways" *Journal of Cellular Physiology* 158:263–269 (1994).

Fujimoto, "brt, A Mouse Gene Encoding a Novel Receptor–type Protein–Tyrosine Kinase, is Preferentially Expressed in the Brain" *Oncogene* 9:693–698 (1994).

Gasic et al., "Coagulation factors X, Xa, and protein S as potent mitogens of cultured aortic smooth muscle cells" *Proc. Natl. Acad. Sci. USA* 89:2317–2320 (Mar. 1992).

Graham et al., "Cloning and mRNA Expression Analysis of a Novel Human Protooncogene, c–mer[1]" *Cell Growth & Differentiation* 5:647–657 (Jun. 1994).

Griffin et al., "Reevaluation of Total, Free, and Bound Protein S and C4b–Binding Protein Levels in Plasma Anticoagulated With Citrate or Hirudin" *Blood* 79(12):3203–3211 (Jun. 1992).

(List continued on next page.)

Primary Examiner—Jean C. Witz
Attorney, Agent, or Firm—Wendy M. Lee

[57] ABSTRACT

A method for enhancing the survival and/or proliferation of Schwann cells (especially human Schwann cells) in cell culture is disclosed which involves culturing the cells in serum free culture medium comprising gas6 and other mitogenic agents, such as heregulin and forskolin. The culturing step is generally preceded by a pre-incubation period wherein nerve tissue comprising the Schwann cells is cultured under appropriate conditions and for a period of time such that demyelination occurs. The isolated Schwann cells can be used as cellular prostheses to treat patients with nervous system injuries. The invention also provides a cell culture medium for culturing Schwann cells.

34 Claims, 21 Drawing Sheets

OTHER PUBLICATIONS

Guenard et al., "Syngenic Schwann Cells Derived from Adult Nerves Seeded in Semipermeable Guidance Channels Enhance Peripheral Nerve Regeneration" *Journal of Neuroscience* 12(9):3310–3320 (1992).

Hammond et al., "The cDNA–deduced primary structure of human sex hormone–binding globulin and location of its steroid–binding domain" *FEBS Letters* 215(1):100–104 (May 1987).

Haynes et al., "Diploid and hyperdiploid rat Schwann cell strains displaying negative autoregulation of growth in vitro and myelin sheath–formulation in vivo" *Journal of Neuroscience Methods* 52:119–127 (1994).

Janssen et al., "A novel putative tyrosine kinase receptor with oncogenic potential" *Oncogene* 6:2113–2120 (1991).

Joseph et al., "Sex hormone–binding globulin, androgen–binding protein, and vitamin K–dependent protein S are homologous to laminin A, merosin, and Drosophila crumbs protein" *FASEB J.* 6:2477–2481 (1992).

Lai et al., "Structure, expression, and activity of Tyro 3, a neural adhesion–related receptor tyrosine kinase" *Oncogene* 9:2567–2578 (1994).

Levi et al., "The functional characteristics of Schwann Cells cultured from human peripheral nerve after transplantation into a gap within the rat sciatic nerve" *J. Neuroscience* 14(3);1309–1319 (1994).

Levi et al., "The influence of Heregulins on Human Schwann Cell Proliferation" *J. Neuroscience* 15(2):1329–1340 (Feb. 1995).

Li et al., "Schwann Cells Induce Sprouting in Motor and Sensory Axons in the Adult Rat Spinal Cord" *J. Neuroscience* 14(7):4050–4063 (Jul. 1994).

Manfioletti et al., "The protein encoded by a growth arrest–specific gene (gas6) is a new member of the vitamin K–dependent proteins related to protein S, a negative coregulator in the blood coagulation cascade" *Molecular & Cellular Biology* 13(8):4976–4985 (Aug. 1993).

Mark et al., "rse, a Novel Receptor–type Tyrosine Kinase with Homology to Axl/Ufo, Is Expressed at High Levels in the Brain" *Journal of Biological Chemistry* 269 (14):10720–10728 (Apr. 8, 1994).

Messing et al., "Hypomeylinating Peripheral Neurophathies and Schwannomas in Transgenic Mice Expressing SV40 T-Antigen" *Journal of Neuroscience* 14(6):3533–3539 (Jun. 1994).

Morgan et al., "Negative regulation of the $P_o$ gene Schwann cells: suppression of $P_o$ mRNA and protei induction in cultured Schwann cells by FGF2 and TGFβ1, TGFβ2, and TGFβ3" *Development* 120:1399–1409 (1994).

Morrissey et al., "Isolation and Functinal characterization of Schwann Cells Derived from Adult Peripheral Nerve" *Journal of Neuroscience* 11(8):2433–2442 (Aug. 1991).

O'Bryan et al., "axl, a transforming gene isolated from primary human myeloid leukemia cells, encodes a novel receptor tyrosine kinase" *Molecular & Cellular Biology* 11(10):5016–5031 (Oct. 1991).

Ohashi et al., "Cloning of the cDNA for a Novel Receptor Tyrosine Kinase, Sky, Predominantly Expressed in Brain" *Oncogene* 9:699–705 (1994).

Paino et al., "Induction of Axon Growth into Schwann Cell Implants Grafted into Lesioned Adult Rat Spinal Cord" *Experimental Neurology* 114:254–257 (1991).

Paino et al., "Regrowth of axons in lesionied adult rat spinal cord: promotion of implants of cultured Schwann cells" *Journal of Neurocytology* 23:433–452 (1994).

Peulve et al., "Establishment of Adult Rat Schwann Cell Cultures: Effect of b–FGF, α–MSH, NGF, PDGF, and TGF–β on Cell Cycle" *Experimental Cell Research* 214:543–550.

Rescigno et al., "A putative receptor tyrosine kinase with unique structural topology" *Oncogene* 6:1909–1913 (1991).

Rutishauser, "Adhesion molecules of the nervous system" *Current Opinion in Neurobiology* 3:709–715 (1993).

Rutkowski et al., "Selective Culture of Mitotically Active Human Schwann Cells from Adult Sural Nerves" *Annals of Neurology* 31(6):580–586 (Jun. 1992).

Scherer et al., "Expression of Growth–Associated Protein–43 kD in Schwann Cells is Regulated by Axon–Schwann Cell Interactions and cAMP" *Journal of Neuroscience Research* 38:575–589 (1994).

Schneider et al., "Genes Specifically Expressed at Growth Arrest of Mammalian Cells" *Cell* 54:787–793 (Sep. 9, 1988).

Schulz et al., "Isolation and expression analysis of tyro3, a murine growth factor receptor tyrosine kinase preferentially expressed in adult brain" *Molecular Brain Research* 28:273–280 (1995).

Stitt et al., "The Anticoagulation Factor Protein S and Its Relative, Gas6, are Ligands for the Tyro 3/Axl Family of Receptor Tyrosine Kinases" *Cell* 80:661–670 (Feb. 1995).

Varnum et al., "Axl receptor tyrosine kinase stimulated by the vitamin K–dependent protein encoded by growth–arrest–specific gene 6" *Nature* 373:623–626 (Feb. 1995).

Walker, "Regulation of Activated Protein C by Protein S" *Journal of Biological Chemistry* 256(21):11128–11131 (Nov. 1981).

Walker, "Regulation of Vitamin K–dependent Protein S" *Journal of Biological Chemistry* 259(16):10335–10339 (Aug. 1984).

Walker et al., "Inactivation of Factor VIII by Activated Protein C and Protein S" *Archives of Biochemistry & Biophysics* 252(1):322–328 (Jan. 1987).

Walker et al., "Regulation of Activated Protein C by a New Protein" *Journal of Biological Chemistry* 255(12):5521–5524 (Jun. 1980).

Watabe et al., "Mitogenic Effects of Platelet–derived Growth Factor, Fibroblast Growth Factor, Transforming Growth Factor–β, and Heparin–Binding Serum Factor for Adult Mouse Schwann Cells" *Journal of Neuroscience Research* 39:525–534 (1994).

Yamamoto et al., "cAMP–dependent differential regulation of extracellular matrix (ECM) gene expression in cultured rat Schwann cells" *Brain Research* 653:335–339 (1994).

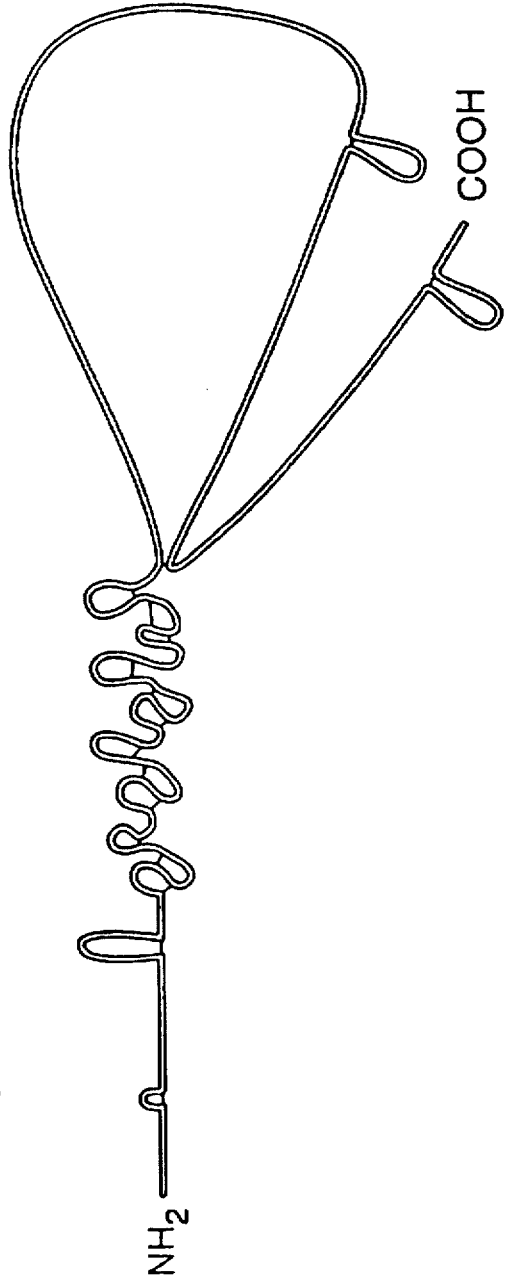
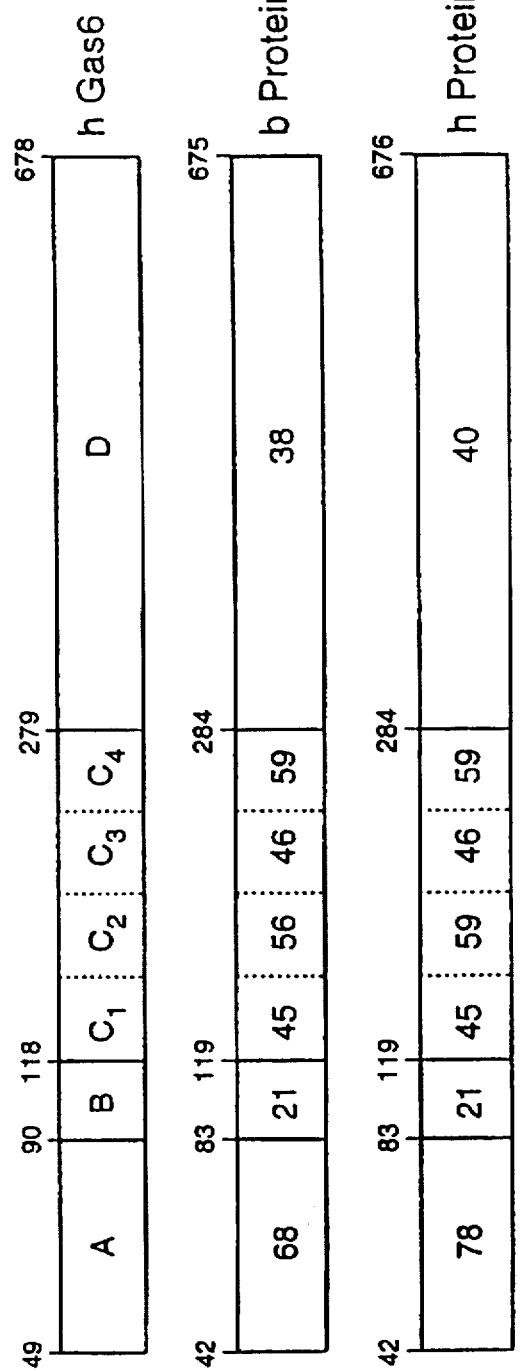
FIG._1A
FIG._1B
FIG._1C
FIG._1D

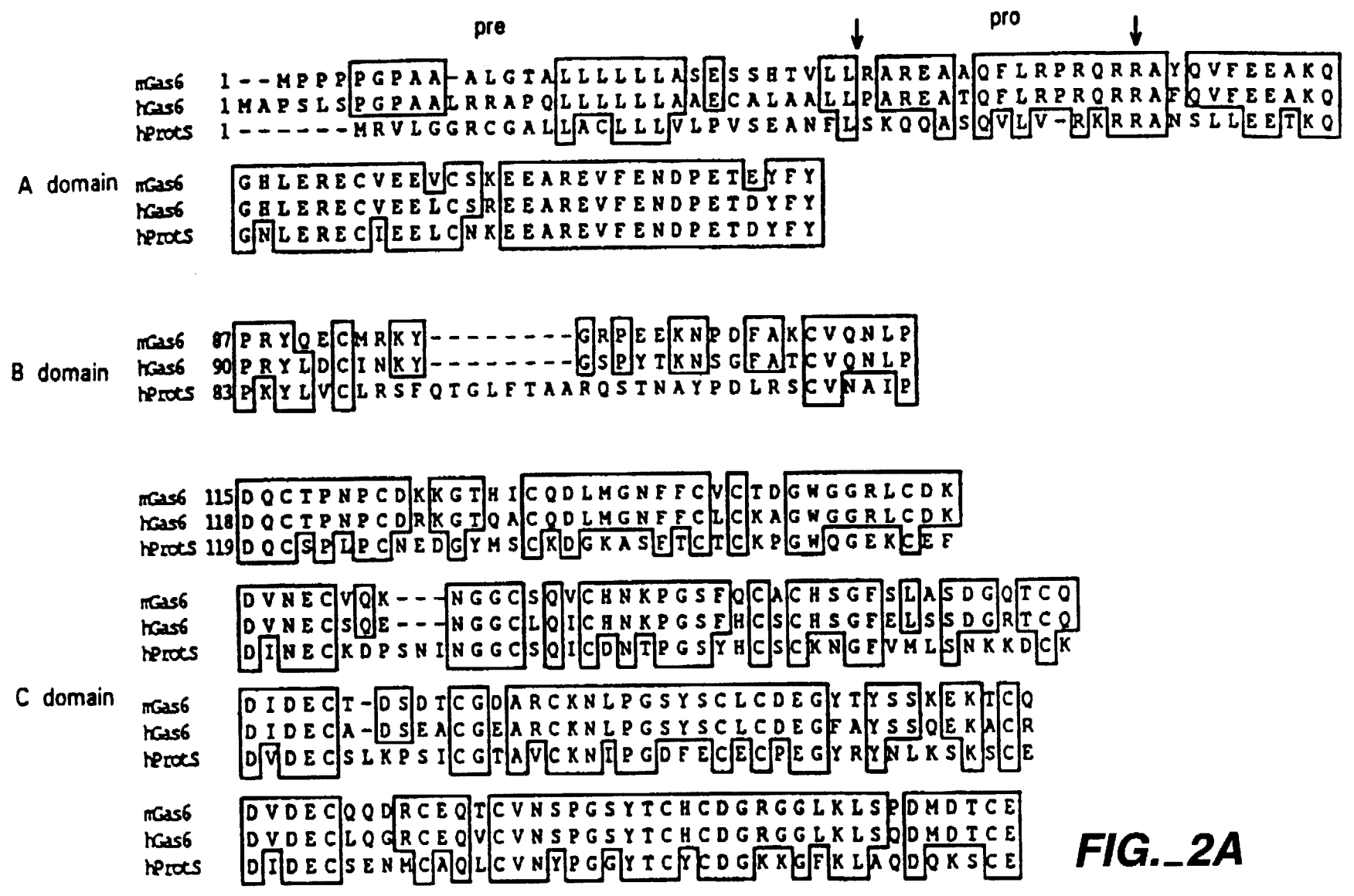

FIG._2A

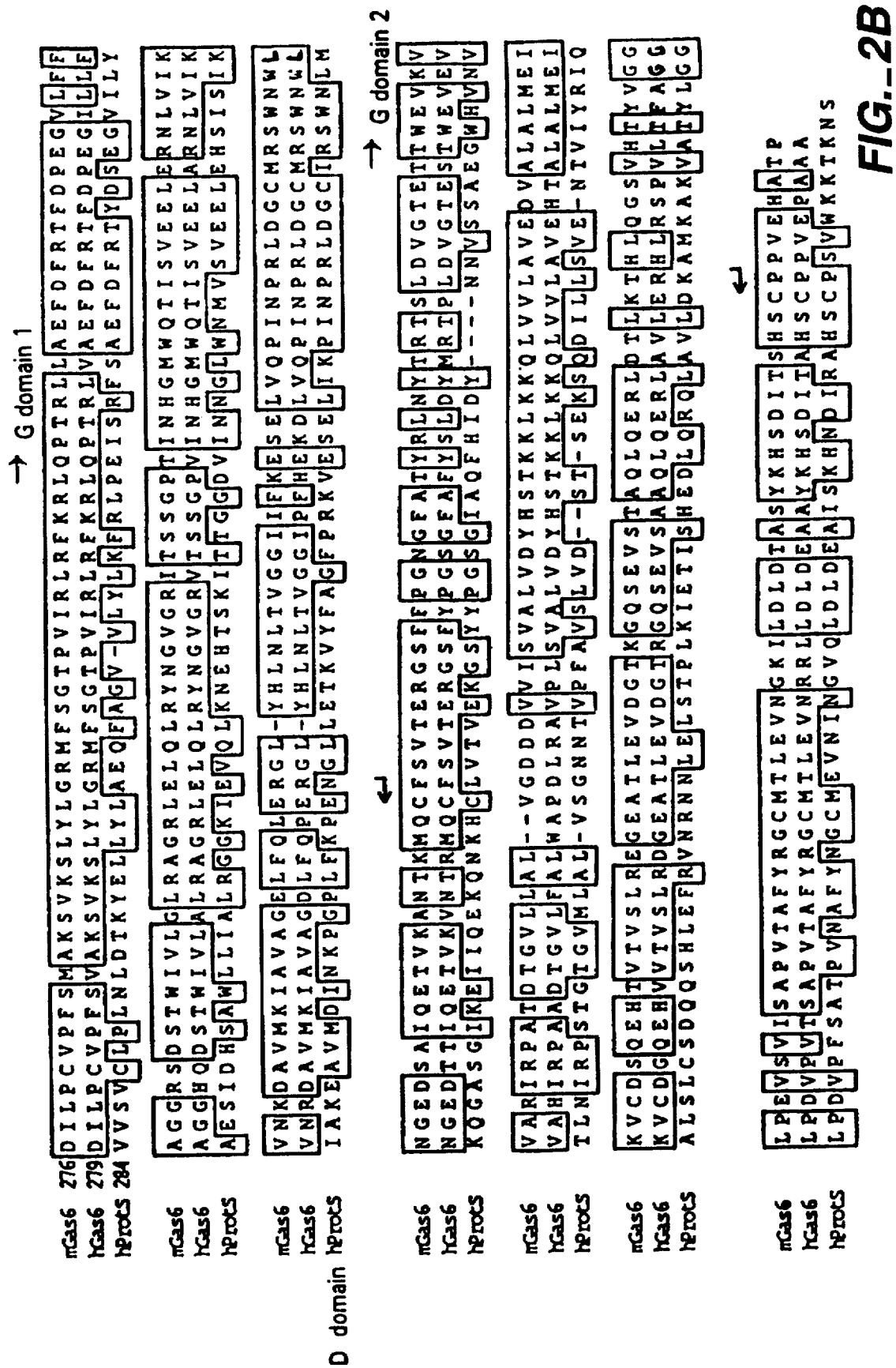
FIG._2B

FIG._3A

```
  1 GAATTCGGGACAGCCTCTCTGCCGCTGCCGCCGCTGTGGCTGTCCTCCTTCTGCTTT
 76 TACTTCCTGCATGACAGTGTTTTCTCATCTGAGCAGACACCAGCTTCAGATGCTCGAGTGAGAAACATGC
151 CTTTCAGTTTGGGCTACTGTTAATCAGCCGGCAGCTCCGTCGATCTATTTCGTCCCTGTCCTCT
226 TGACGAGCCCGGGATGTTTGAGTAGCATTTAAAGAACTAGAAACAGCAGCTTAAAGAAT
301 TATTACGATATACTTTGATTTGTAGTGTGCTAGAGAGCTTTTCTCCCCCTTGCATCTTTCTGAACTCTCTTGA
376 TTTTAATAATGGCCTTGGACTTGGACGATTTATCGTGTATCATTTGGTTGGGGGG
451 CCTCTGCTGTGTAATGACCGTGAGAGCCGCCAGCCTTCTCTGAGGTGAGCCGATGGAGATTTATTCCCAG
                                                        M  E  I  Y  S  P  D
                                                        1
526 ACATGTCTGAGGTCGCCGCGAGAGGTCCTCCAGTCAGTCCACTCAGTGCAGACCCATCCTGATGGC
      M  S  E  V  A  A  E  R  S  S  S  P  S  T  Q  L  S  A  D  P  S  L  D  G  L
      8
601 TTCCGGCAGCAGAGACATGCCAGAGCCCAGAGCCCCTGAGAACTGAAGATGGGAGACTTGGCCTCAACTGCAGAAAATCTGCATTGTCCCATCC
     P  A  A  E  D  M  P  E  P  Q  T  E  D  G  R  T  P  G  L  V  G  L  A  V  P
     33
676 CCTGCCTGTGCCTAGAAGCTGAAGCGCTGAGAGGTTGCCTCAACTGCAGAGGCCTGAATAGTGAAAATCTGCATTGTCCCATCC
     P  A  A  E  D  M  P  E  P  Q  T  E  D  G  R  T  P  G  L  V  G  L  A  V  P
     58
751 TGGCTGTGCCTTGTCTCAGCTGGCATCGCTGGGCTTAAGTGGTTTGTGGACAGATCTTTGAATATG
      A  L  V  S  L  L  I  A  G  L  K  W  V  F  V  D  K  I  F  E  Y  D
      83
826 ACTTCCTACTCACCTTGACCCTGGGGGGGTTAGGCAGGACCCTATTATTCTCTGGACCCTGATATCAGCAACTGCTGCCTCAG
      S  P  T  H  L  D  P  G  G  L  G  Q  D  P  I  I  S  L  D  A  T  A  A  S  A
      108
901 CTGTGTGGGTGTCGTCTGAGGCATACACTTCACCTGTCTCTAGGCTCAATCTGAAGTGAGGTTCAAGTTACAG
      V  W  V  S  S  E  A  Y  T  S  P  V  S  R  A  Q  S  E  S  E  V  Q  V  T  V
      133
```

```
 976  TCCAAGGTGCACAAGGCTGTGTGTCCTTTGAACCATCAGGGCACCGACACCGAAGAATGTATTTTTGCCTTT
 158   Q  G  D  K  A  V  V  S  F  E  P  S  A  A  P  T  P  K  N  R  I  F  A  F  S

1051  CTTTCTGCCGTCCACTGGCGCCATCTCCCCTTCACCCGAACCCTGAGGTGAGAACGCCCAGTCAGCAA
 183   F  L  P  S  T  A  P  S  F  P  S  P  T  R  N  P  E  V  R  T  P  K  S  A  T

1126  CTCAGCCACAACAACAGAAACTAATCTCCAAACTGCTCTAACTTTCTACATTCCACCACTGGACAA
 208   Q  P  Q  T  T  E  T  N  L  Q  T  A  P  K  L  S  T  S  T  T  G  T  S

1201  GCCATCTGTAAAATGTGCGGAGAAGAGAAACTTCTGTGAATGGAGGGGAGTGCTTCATGTGAAAGACC
 233   S  I  C  K  M  C  G  E  E  K  L  L  *  M  E  G  S  A  S  C  E  R  P   [alt: A E K E K T F [C] V N G G E [C] F M V K D L ]

1276  TTTCAAACCCCTGTAAAATGTGCAAGTGCCCAAATGAGTTTACTGGTGATCGCTGCCAAAACTACGTAATGG
 258   S  N  P  S  R  Y  L  [C] K  [C] P  N  E  F  T  G  D  R  [C] Q  N  Y  V  M  A

1351  CCAGCTTCTACAGTACGTCCACTCCAACTCCCTTCGTGCTTCTCCGAATAGAGCATGCTCAGTTGGTGCTCTTCTT
 283   S  F  Y  S  T  S  T  P  F  L  S  L  P  E  Q

1426  GTTGCTGCATCTCCCCTCAGATTCCACTAGAGTGTCTTACCAGATCTAATATTGACTGCCTCTGCCT

1501  GTCGCATGAGAACATTAACAAAGCAATTGTATACTTCCTCGTCCGACTAGTTGGCTCTGAGATACTATA

1576  GGTGTGTGAGGCTCCAGATGTTTCTGAATTGATACAAATTGATAGTCAATATCAAGCAG

1651  TGAAATATGATATAAGGCATTTCACTTTTATTGATAAATAAATCATTCTACTGAACAGTCCA

1726  TCTTCTTTATACAATGACCACATCCGAAAGGGTGTGCTAAGCTGTAACGATATGCCACTTGAAATGATGGTA

1801  AGTAATTTGATTCAGAATGTGTATTGTCACAATAACATATAAAGGAAAAAAAAACCGAATTC
```

EGF-like

FIG.—3B

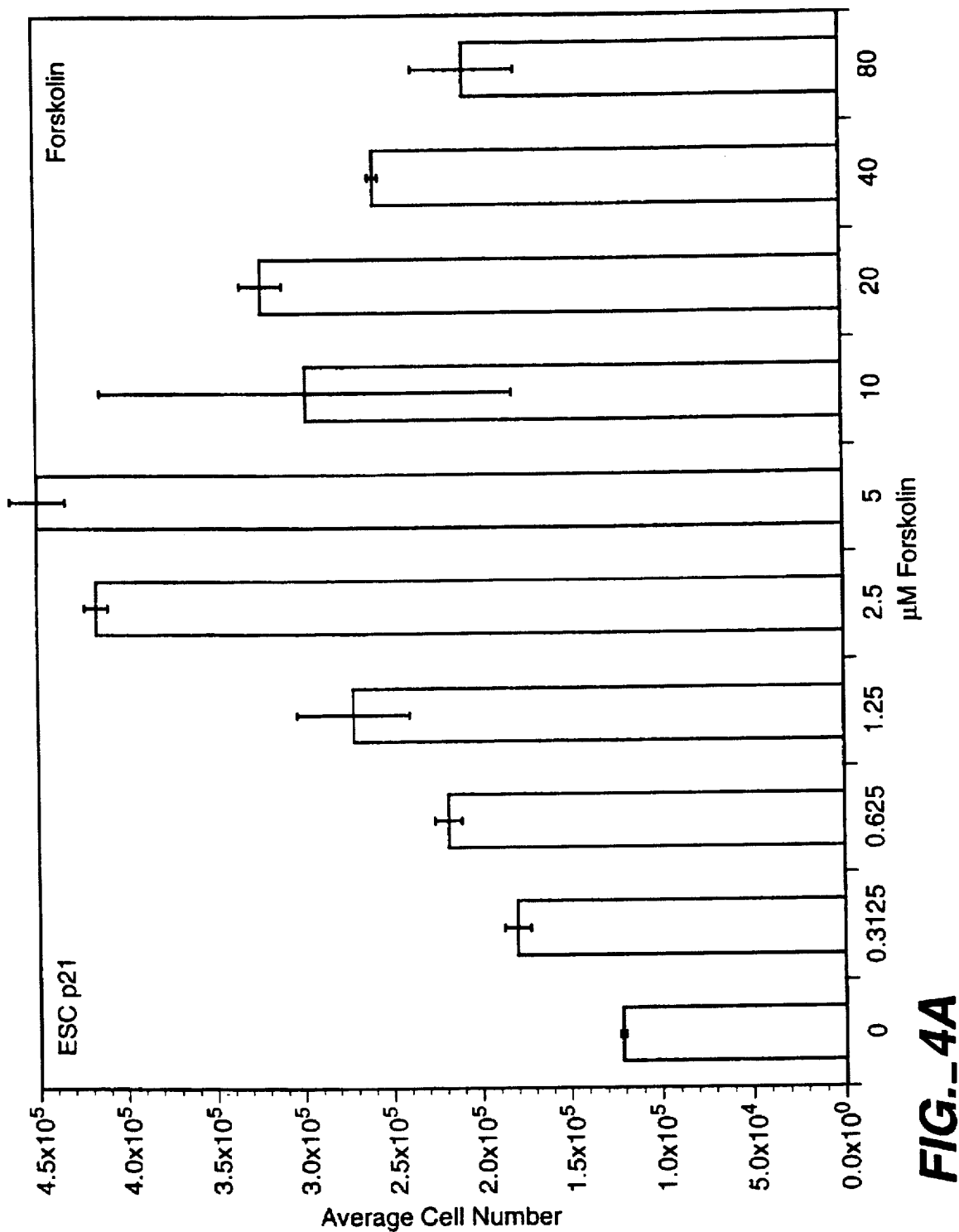
FIG._4A

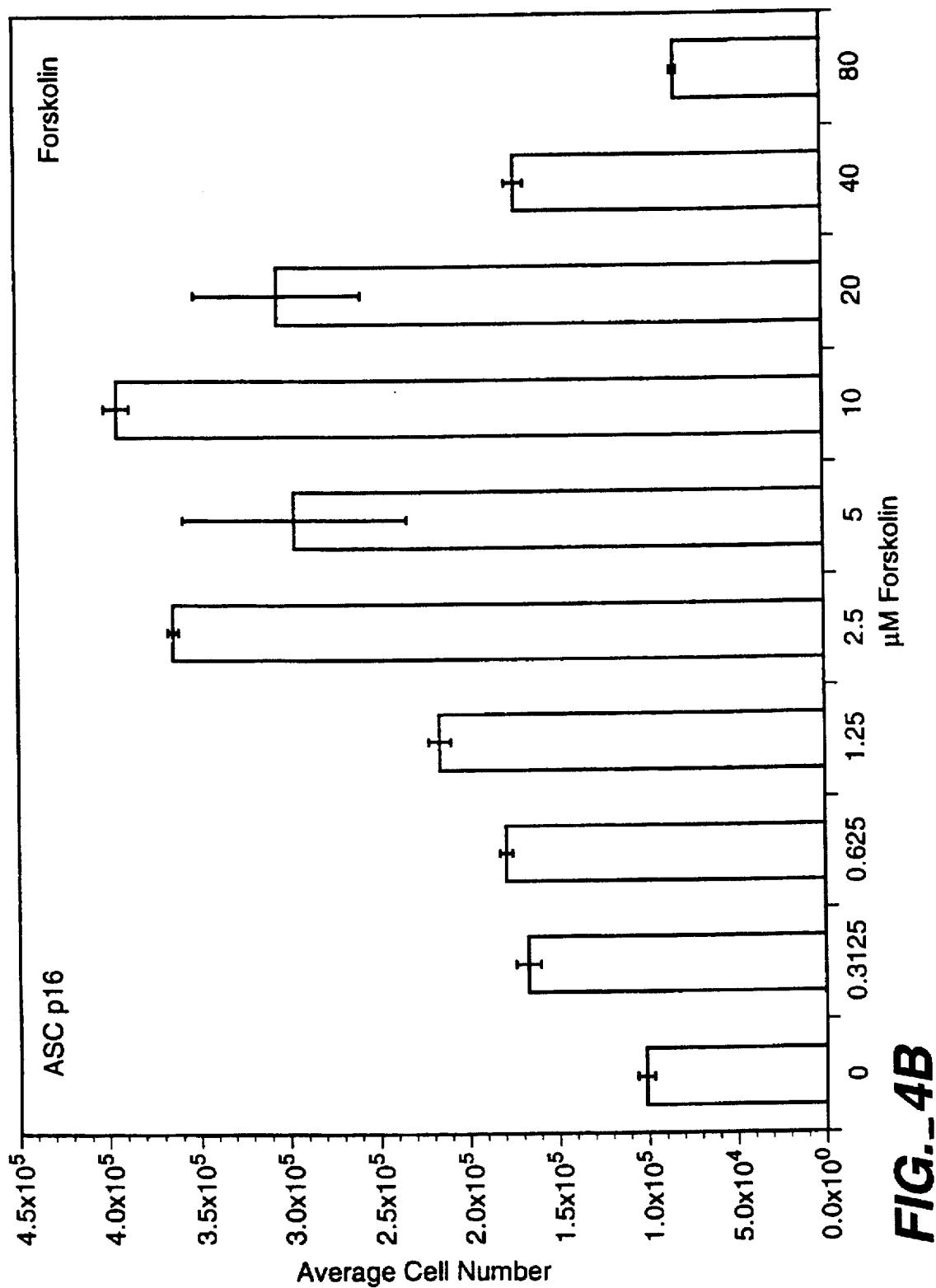
FIG._4B

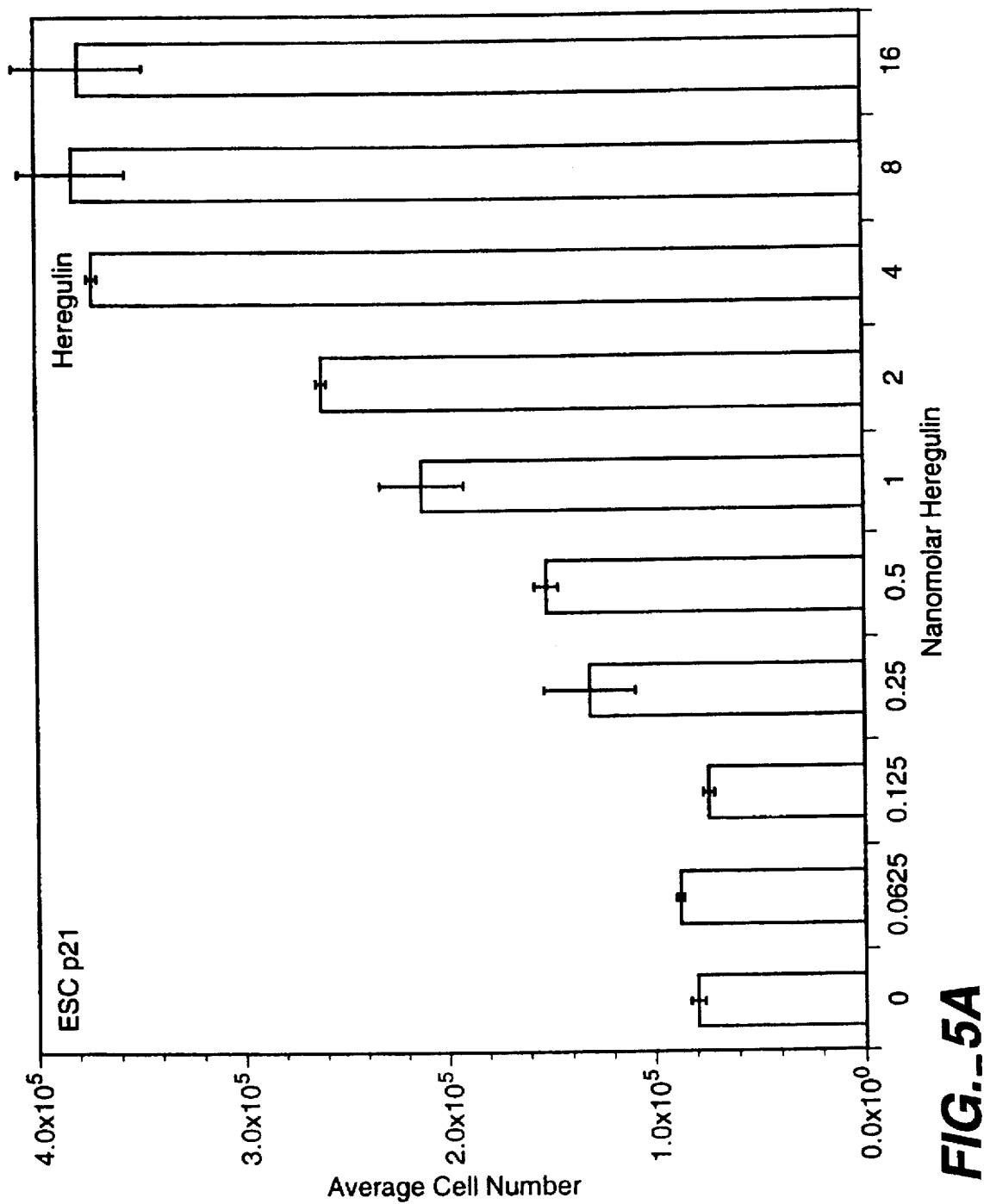
FIG._5A

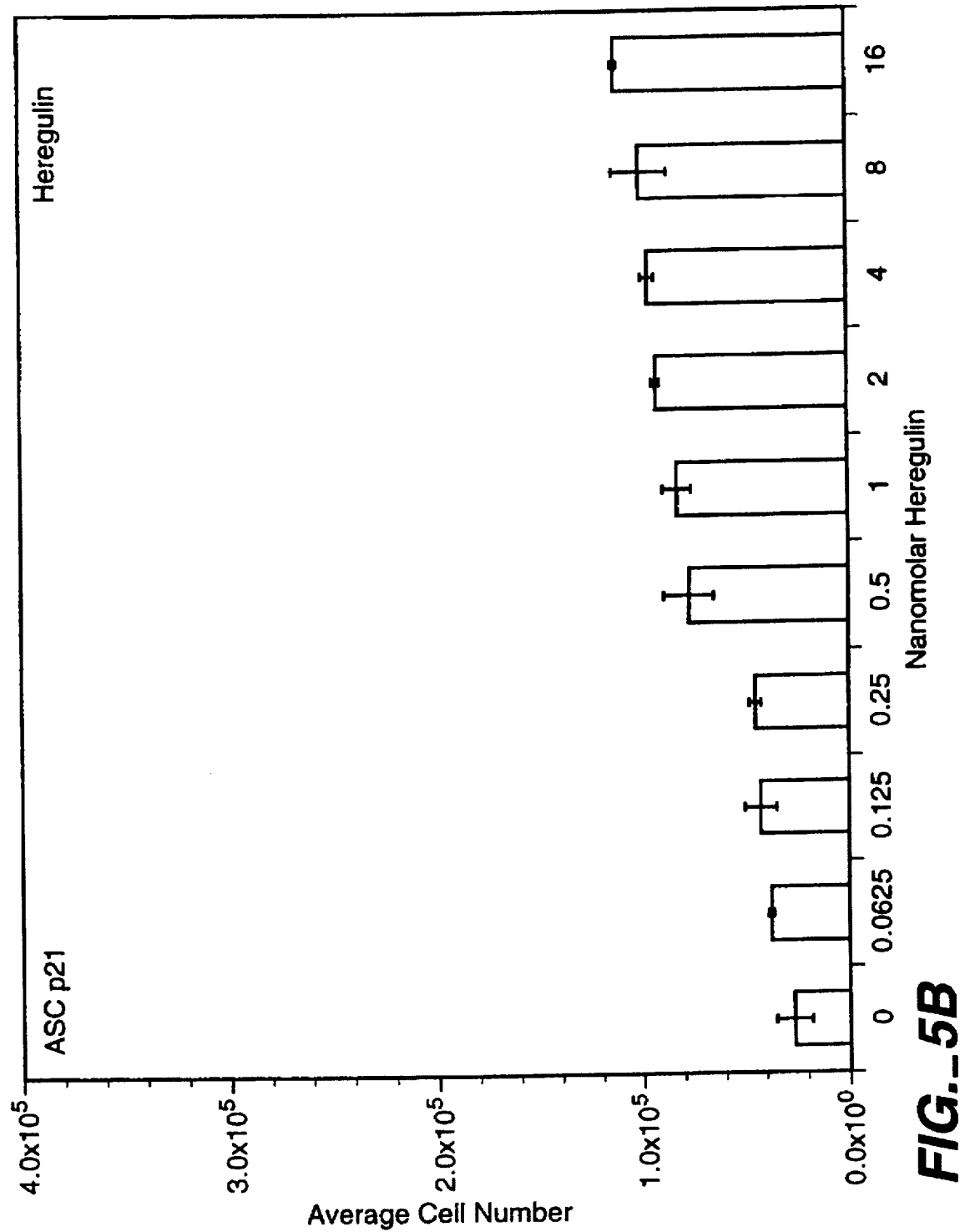
FIG._5B

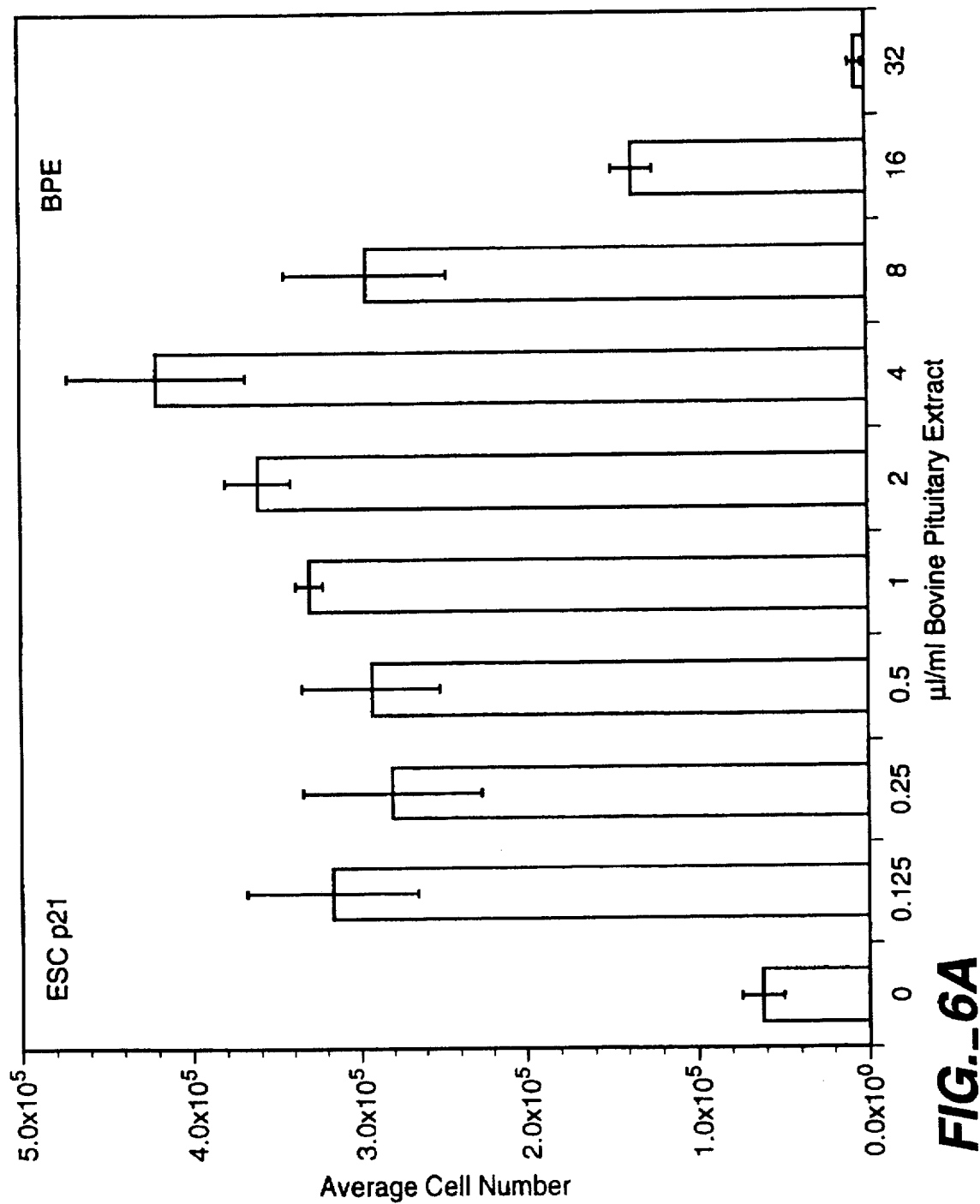
FIG._6A

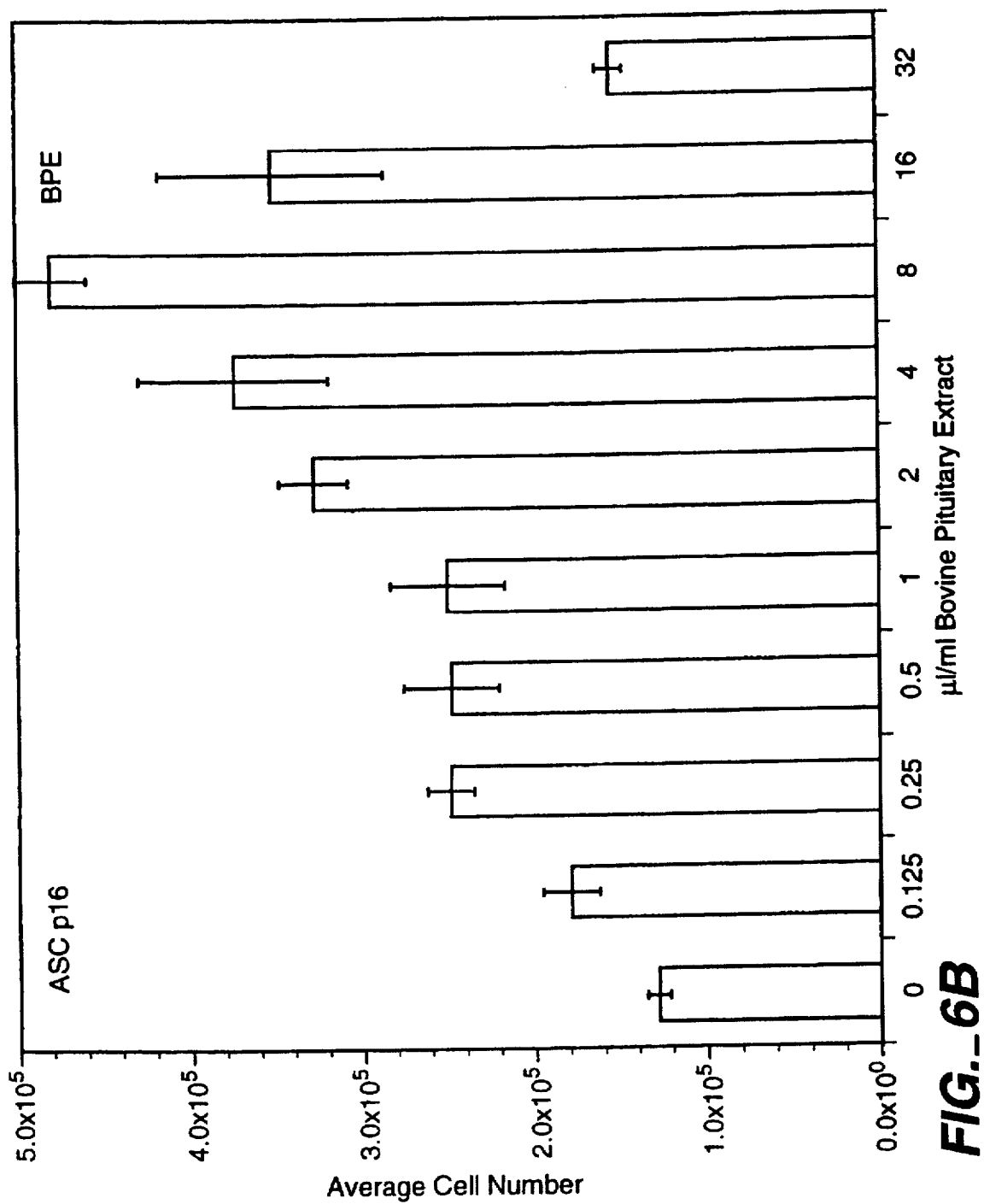
FIG._6B

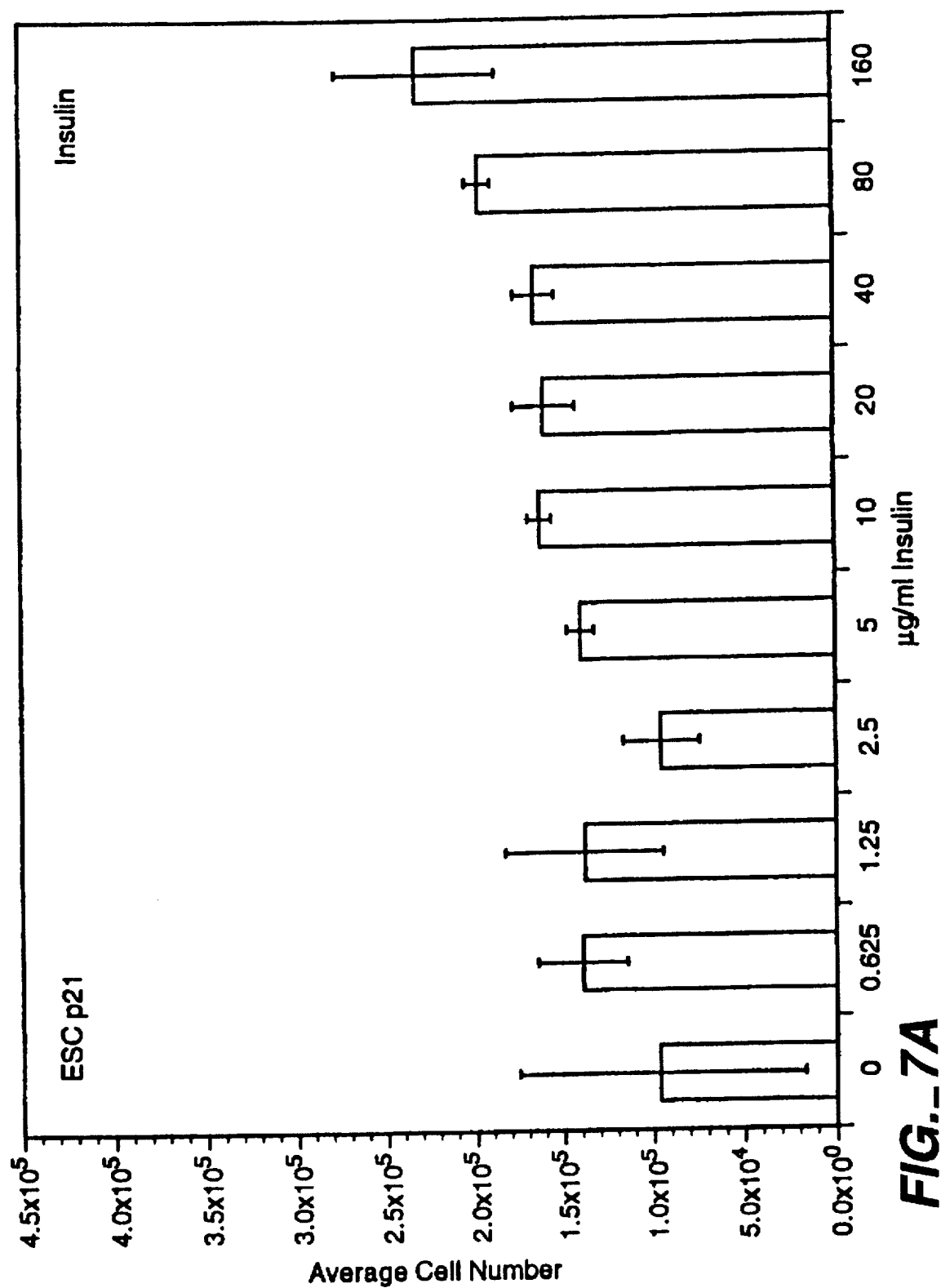
FIG._7A

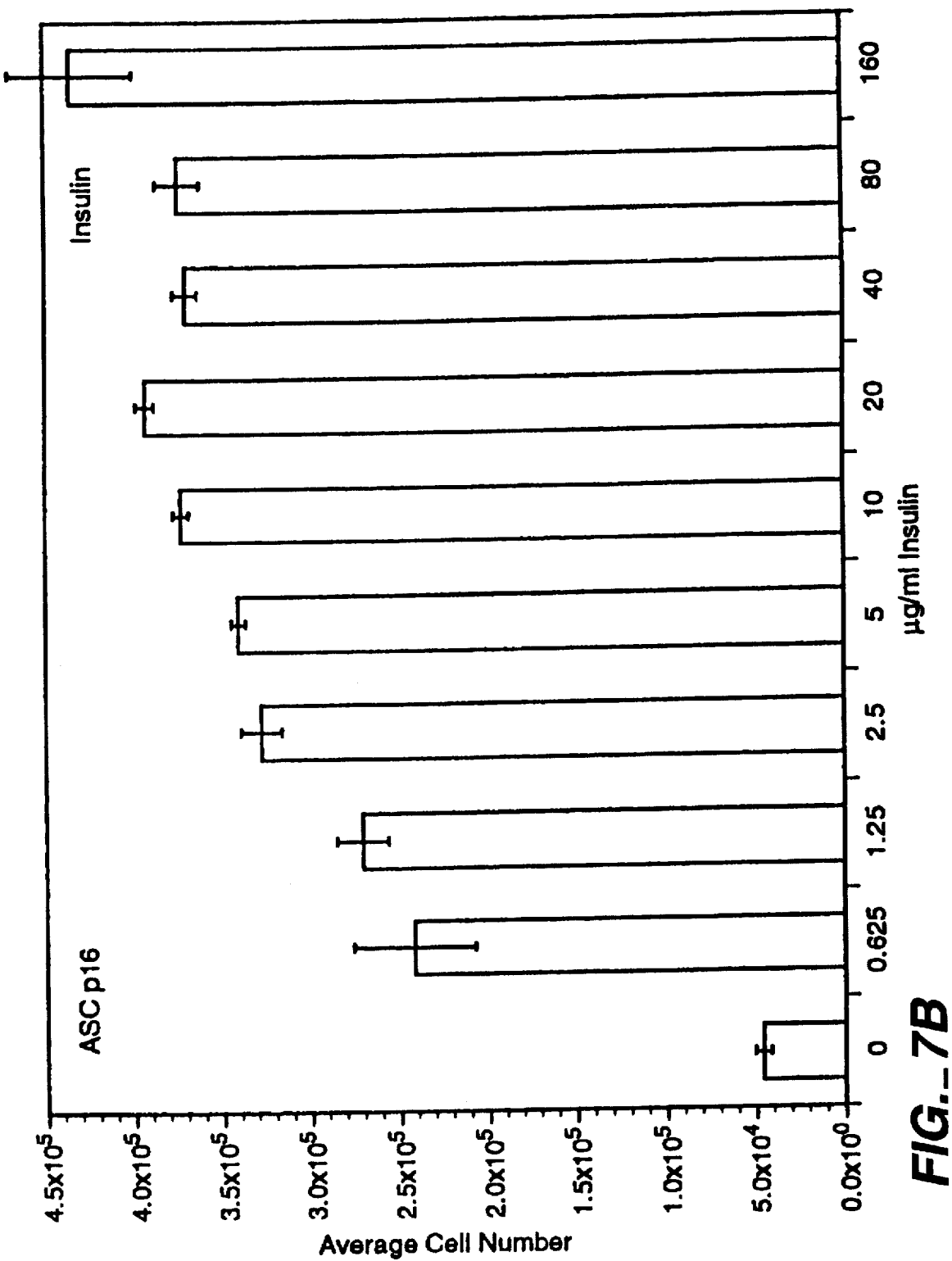
FIG._7B

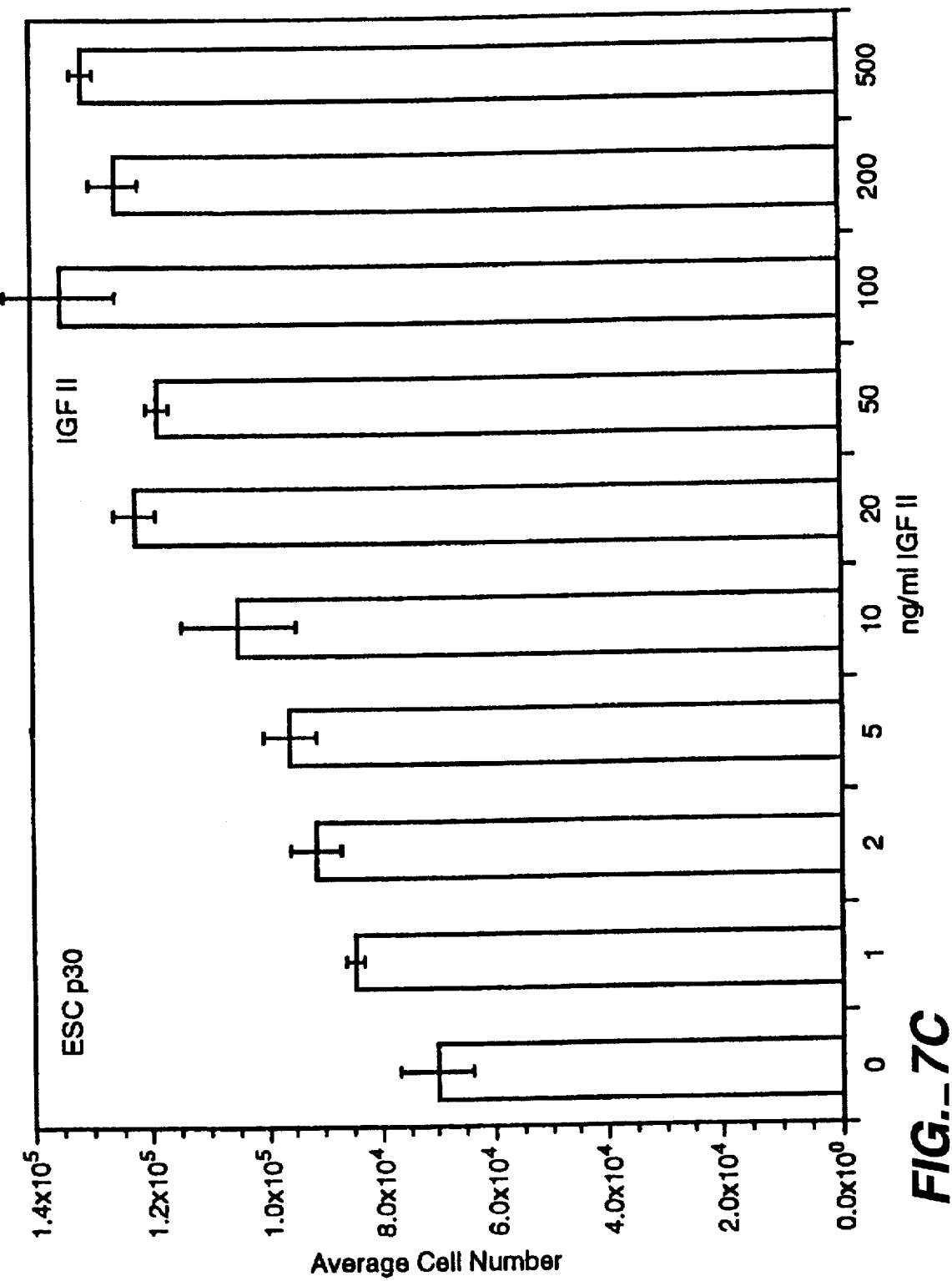
FIG._7C

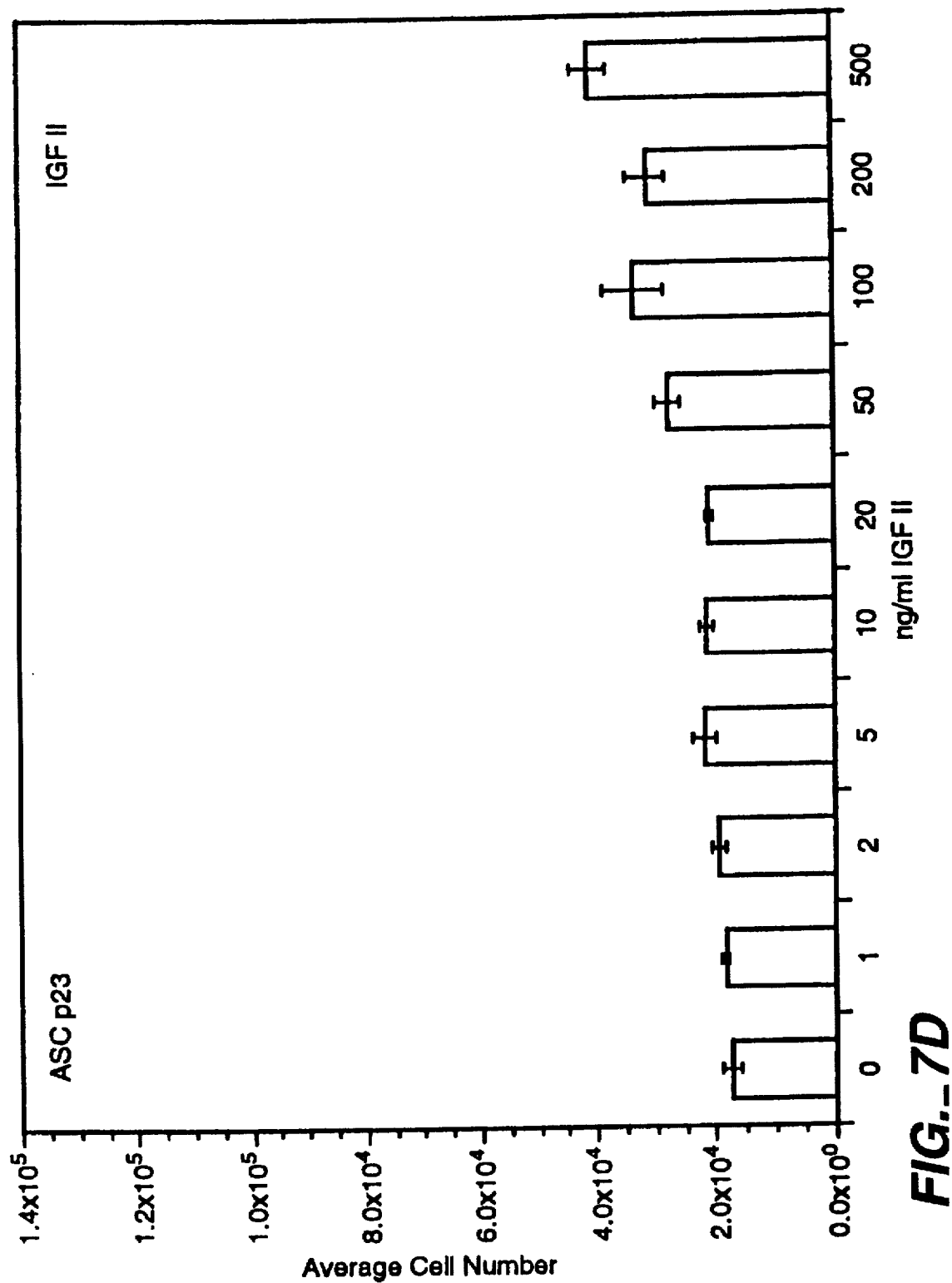
FIG._7D

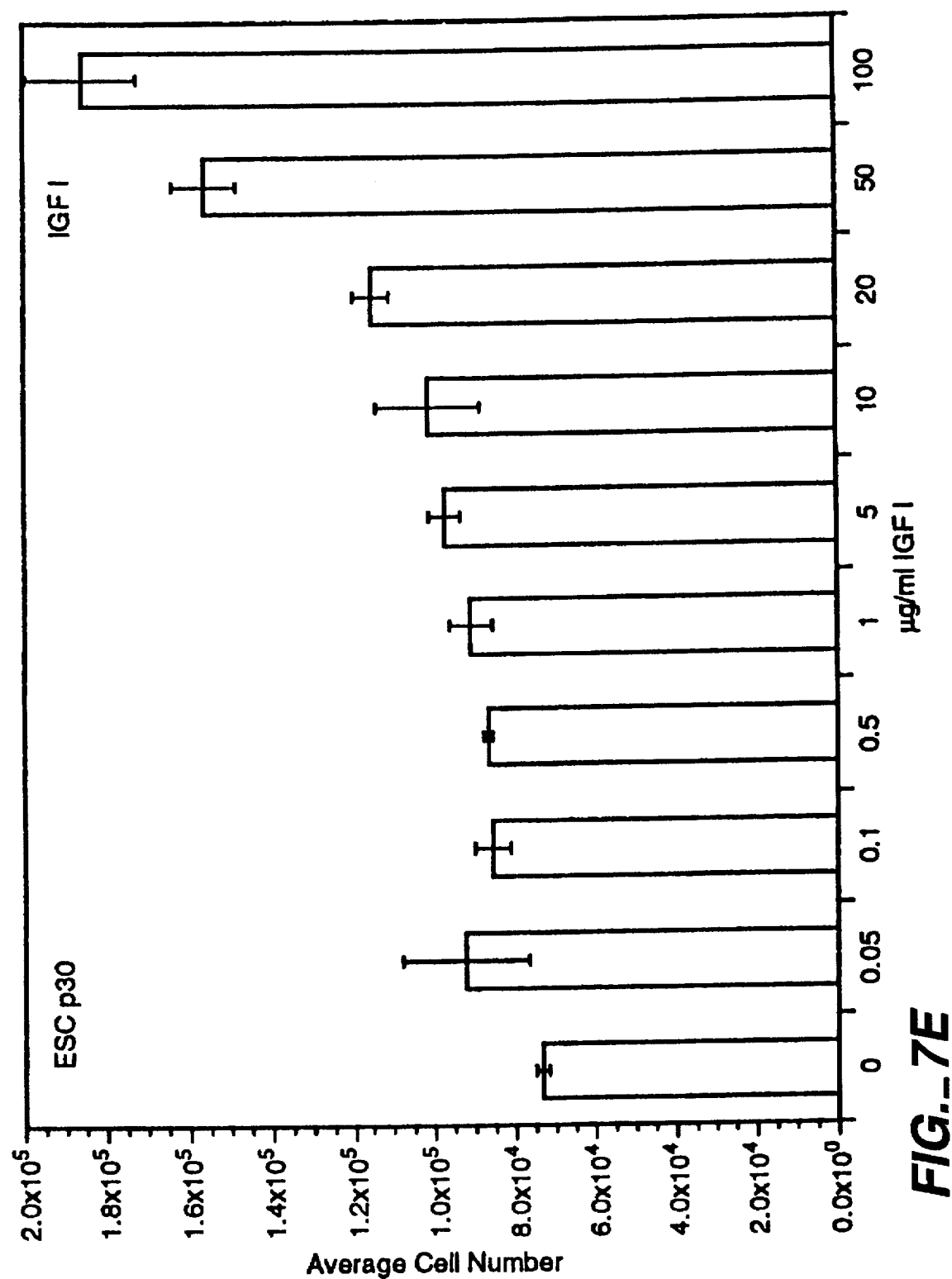
FIG._7E

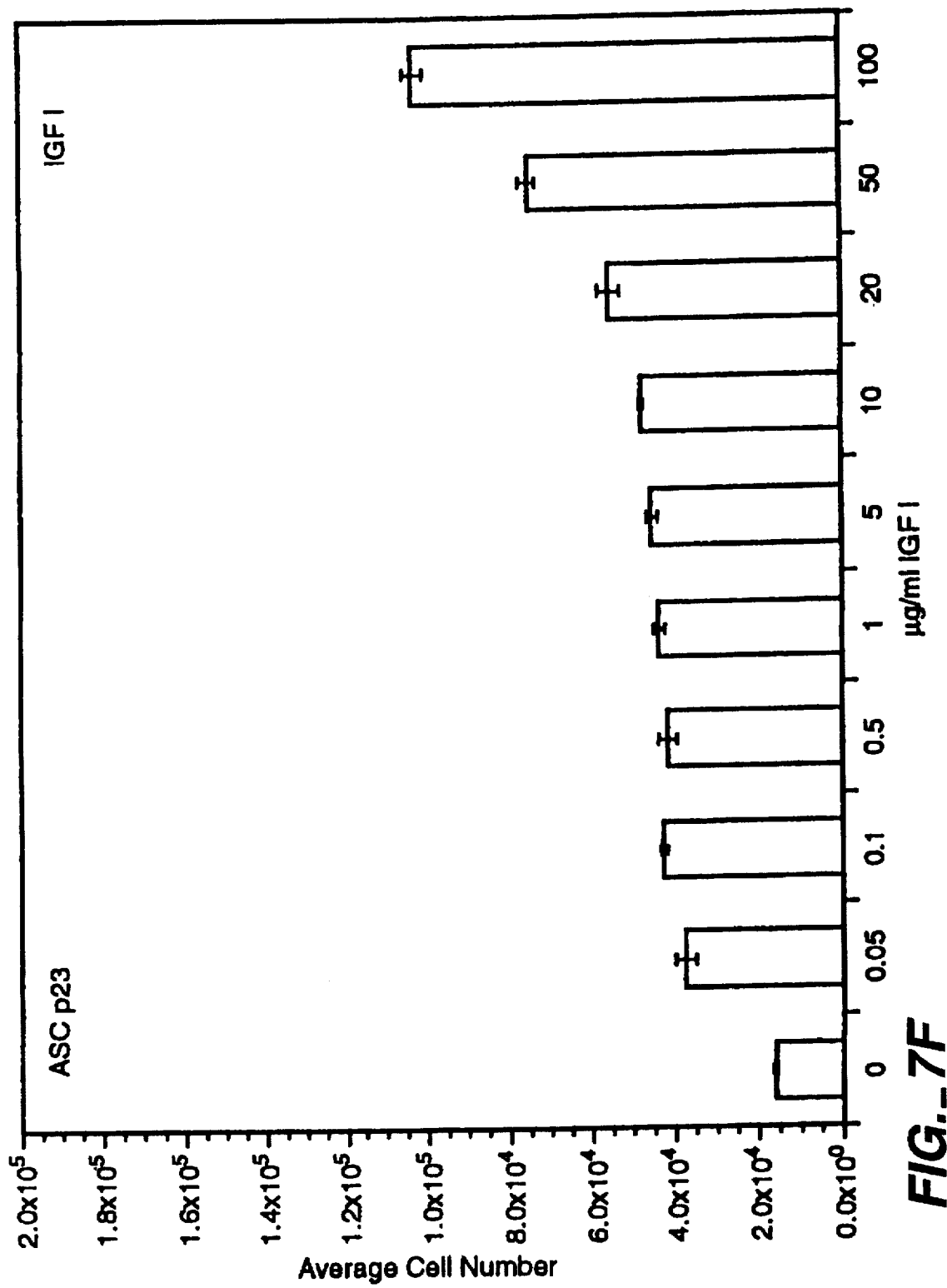
FIG._7F

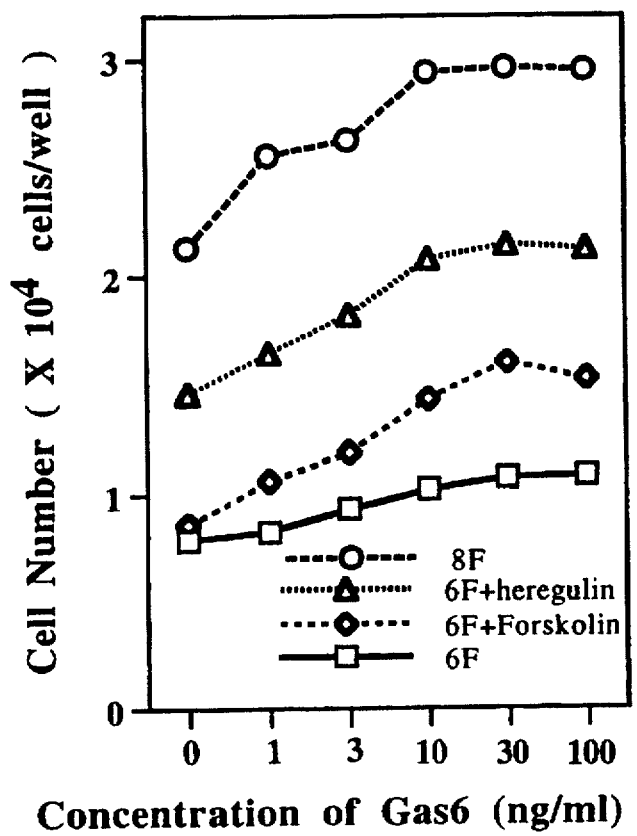
FIG._8A
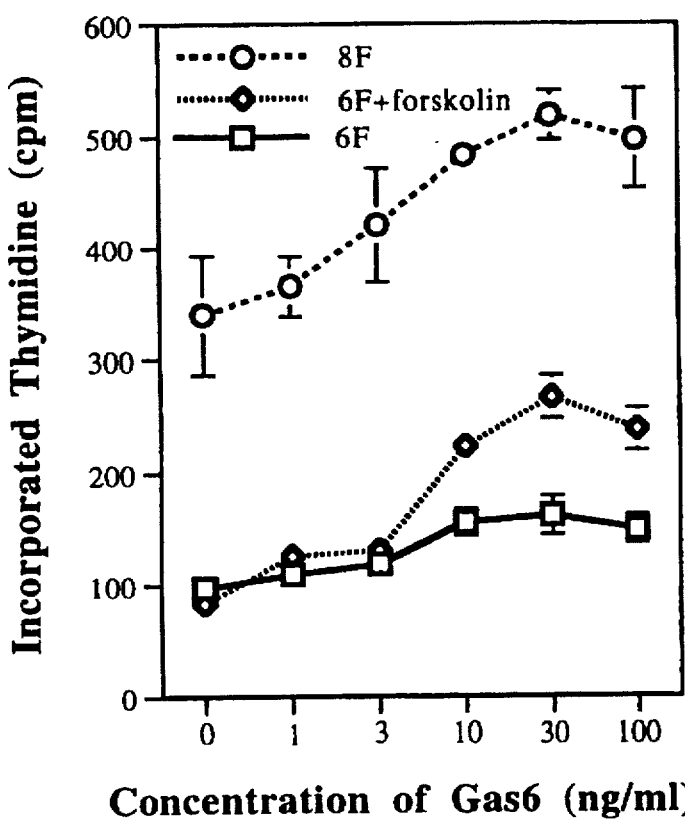
FIG._8B

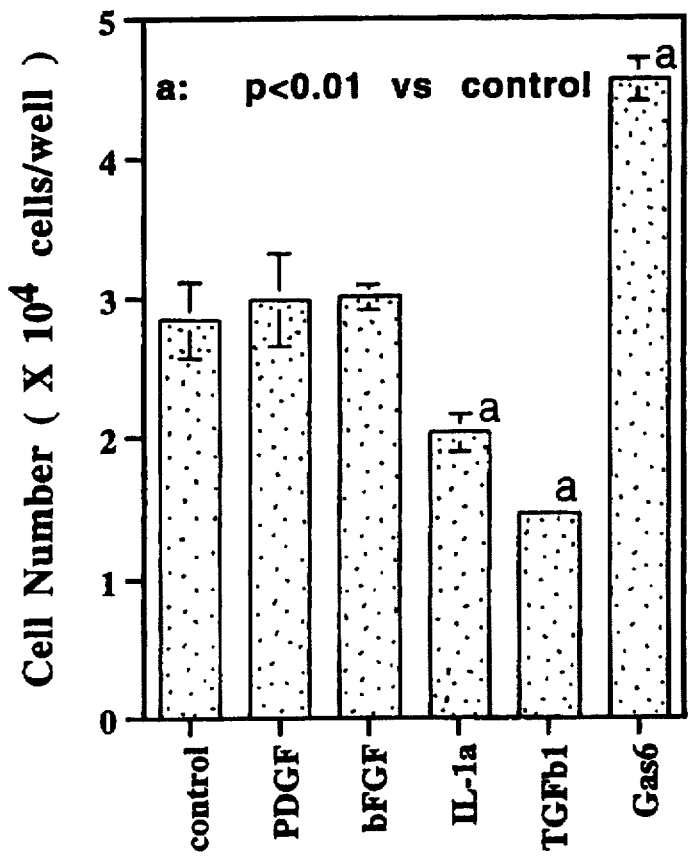
FIG._8C
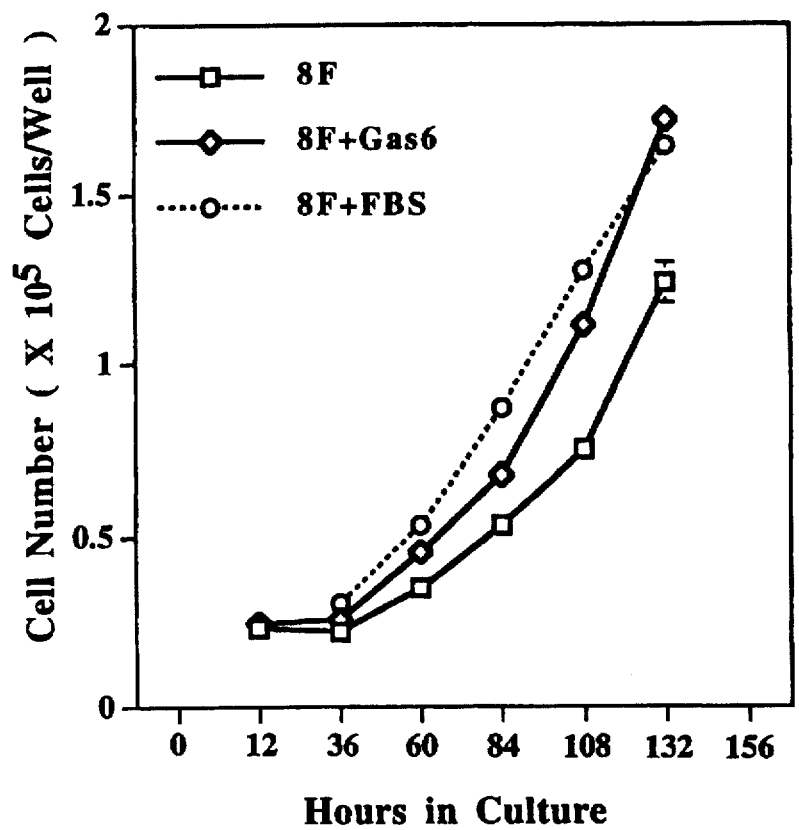
FIG._9

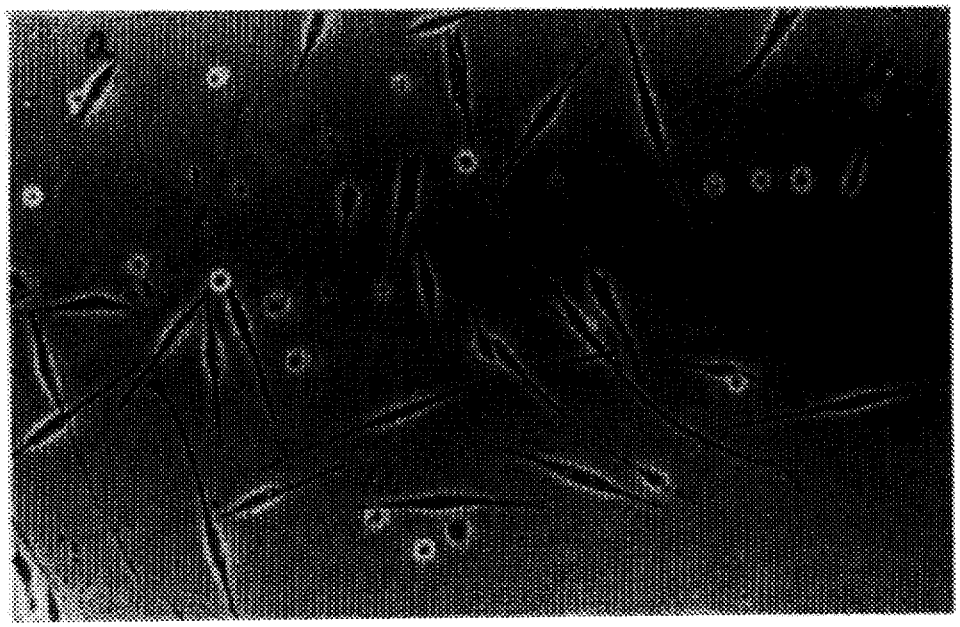
FIG._10A
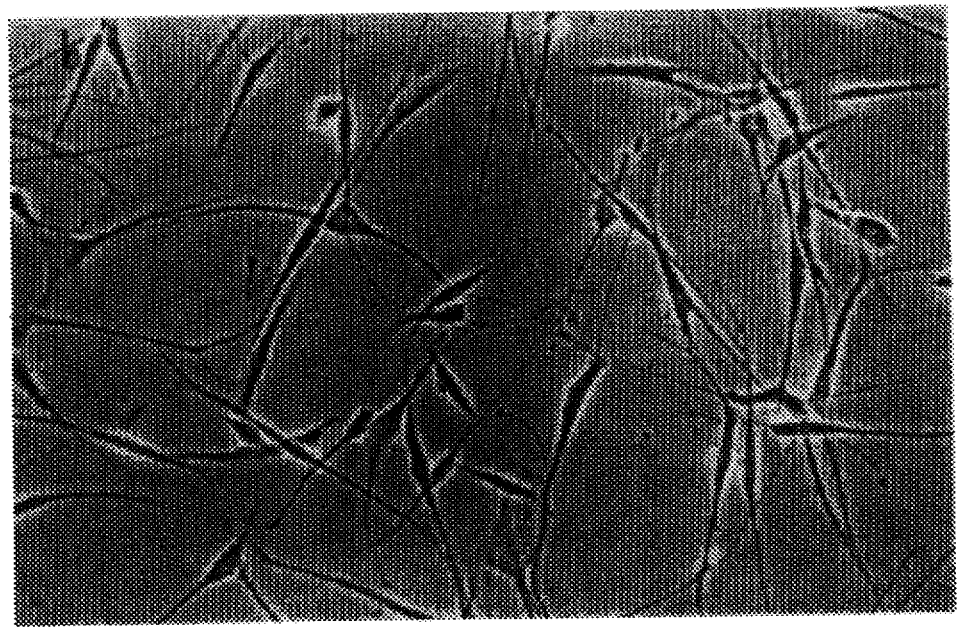
FIG._10B

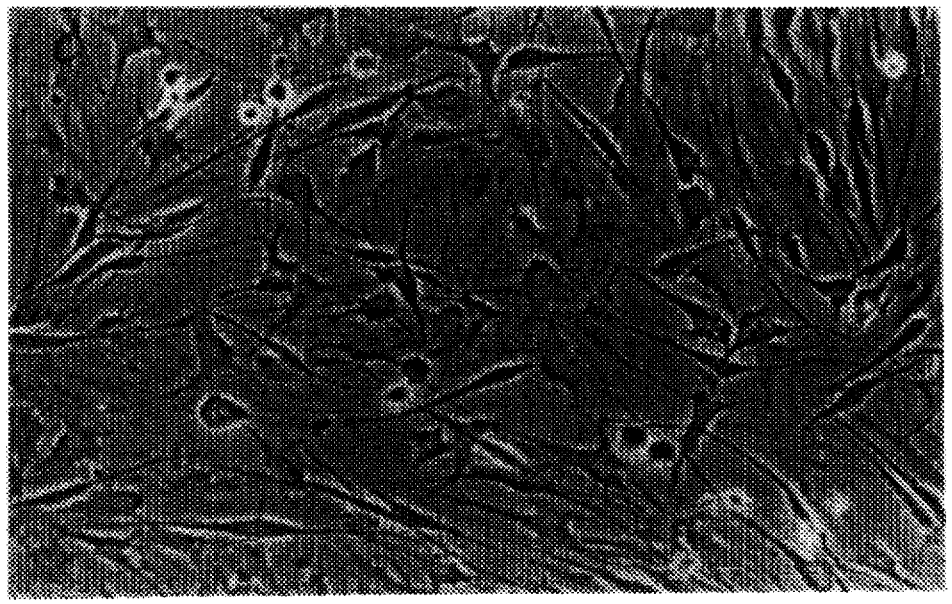
FIG._10C
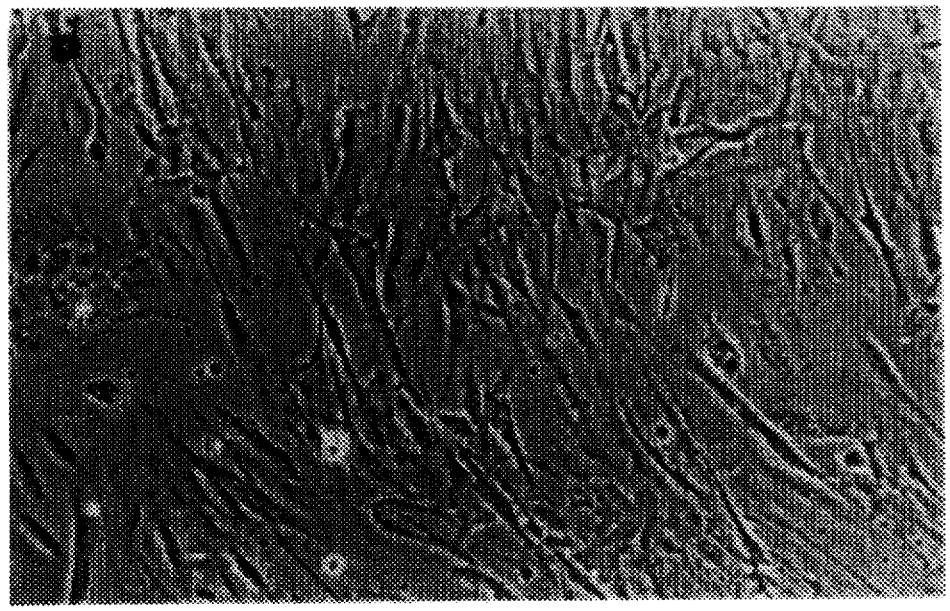
FIG._10D

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 673 amino acids
        ( B ) TYPE: amino acid
        ( D ) TOPOLOGY: linear (xi) SEQUENCE DESCRIPTION: SEQ ID NO:1:

| Met | Pro | Pro | Pro | Pro | Gly | Pro | Ala | Ala | Ala | Leu | Gly | Thr | Ala | Leu |
|---|---|---|---|---|---|---|---|---|---|---|---|---|---|---|
| 1 | | | | 5 | | | | | 10 | | | | | 15 |

| Leu | Leu | Leu | Leu | Leu | Ala | Ser | Glu | Ser | Ser | His | Thr | Val | Leu | Leu |
| | | | | 20 | | | | | 25 | | | | | 30 |

| Arg | Ala | Arg | Glu | Ala | Ala | Gln | Phe | Leu | Arg | Pro | Arg | Gln | Arg | Arg |
| | | | | 35 | | | | | 40 | | | | | 45 |

| Ala | Tyr | Gln | Val | Phe | Glu | Glu | Ala | Lys | Gln | Gly | His | Leu | Glu | Arg |
| | | | | 50 | | | | | 55 | | | | | 60 |

| Glu | Cys | Val | Glu | Glu | Val | Cys | Ser | Lys | Glu | Glu | Ala | Arg | Glu | Val |
| | | | | 65 | | | | | 70 | | | | | 75 |

| Phe | Glu | Asn | Asp | Pro | Glu | Thr | Glu | Tyr | Phe | Tyr | Pro | Arg | Tyr | Gln |
| | | | | 80 | | | | | 85 | | | | | 90 |

| Glu | Cys | Met | Arg | Lys | Tyr | Gly | Arg | Pro | Glu | Glu | Lys | Asn | Pro | Asp |
| | | | | 95 | | | | | 100 | | | | | 105 |

| Phe | Ala | Lys | Cys | Val | Gln | Asn | Leu | Pro | Asp | Gln | Cys | Thr | Pro | Asn |
| | | | | 110 | | | | | 115 | | | | | 120 |

| Pro | Cys | Asp | Lys | Lys | Gly | Thr | His | Ile | Cys | Gln | Asp | Leu | Met | Gly |
| | | | | 125 | | | | | 130 | | | | | 135 |

| Asn | Phe | Phe | Cys | Val | Cys | Thr | Asp | Gly | Trp | Gly | Gly | Arg | Leu | Cys |
| | | | | 140 | | | | | 145 | | | | | 150 |

| Asp | Lys | Asp | Val | Asn | Glu | Cys | Val | Gln | Lys | Asn | Gly | Gly | Cys | Ser |
| | | | | 155 | | | | | 160 | | | | | 165 |

| Gln | Val | Cys | His | Asn | Lys | Pro | Gly | Ser | Phe | Gln | Cys | Ala | Cys | His |
| | | | | 170 | | | | | 175 | | | | | 180 |

| Ser | Gly | Phe | Ser | Leu | Ala | Ser | Asp | Gly | Gln | Thr | Cys | Gln | Asp | Ile |
| | | | | 185 | | | | | 190 | | | | | 195 |

| Asp | Glu | Cys | Thr | Asp | Ser | Asp | Thr | Cys | Gly | Asp | Ala | Arg | Cys | Lys |
| | | | | 200 | | | | | 205 | | | | | 210 |

| Asn | Leu | Pro | Gly | Ser | Tyr | Ser | Cys | Leu | Cys | Asp | Glu | Gly | Tyr | Thr |
| | | | | 215 | | | | | 220 | | | | | 225 |

| Tyr | Ser | Ser | Lys | Glu | Lys | Thr | Cys | Gln | Asp | Val | Asp | Glu | Cys | Gln |
| | | | | 230 | | | | | 235 | | | | | 240 |

| Gln | Asp | Arg | Cys | Glu | Gln | Thr | Cys | Val | Asn | Ser | Pro | Gly | Ser | Tyr |
| | | | | 245 | | | | | 250 | | | | | 255 |

| Thr | Cys | His | Cys | Asp | Gly | Arg | Gly | Gly | Leu | Lys | Leu | Ser | Pro | Asp |
| | | | | 260 | | | | | 265 | | | | | 270 |

| Met | Asp | Thr | Cys | Glu | Asp | Ile | Leu | Pro | Cys | Val | Pro | Phe | Ser | Met |
| | | | | 275 | | | | | 280 | | | | | 285 |

| Ala | Lys | Ser | Val | Lys | Ser | Leu | Tyr | Leu | Gly | Arg | Met | Phe | Ser | Gly |
| | | | | 290 | | | | | 295 | | | | | 300 |

| Thr | Pro | Val | Ile | Arg | Leu | Arg | Phe | Lys | Arg | Leu | Gln | Pro | Thr | Arg |
| | | | | 305 | | | | | 310 | | | | | 315 |

| Leu | Leu | Ala | Glu | Phe | Asp | Phe | Arg | Thr | Phe | Asp | Pro | Glu | Gly | Val |
| | | | | 320 | | | | | 325 | | | | | 330 |

| Leu | Phe | Phe | Ala | Gly | Gly | Arg | Ser | Asp | Ser | Thr | Trp | Ile | Val | Leu |
| | | | | 335 | | | | | 340 | | | | | 345 |

| Gly | Leu | Arg | Ala | Gly | Arg | Leu | Glu | Leu | Gln | Leu | Arg | Tyr | Asn | Gly |
| | | | | 350 | | | | | 355 | | | | | 360 |

| Val | Gly | Arg | Ile | Thr | Ser | Ser | Gly | Pro | Thr | Ile | Asn | His | Gly | Met |
| | | | | 365 | | | | | 370 | | | | | 375 |

| Trp | Gln | Thr | Ile | Ser | Val | Glu | Glu | Leu | Glu | Arg | Asn | Leu | Val | Ile |
| | | | | 380 | | | | | 385 | | | | | 390 |

| | | | | | | | | | | | | |
|---|---|---|---|---|---|---|---|---|---|---|---|---|
| Lys | Val | Asn | Lys | Asp<br>395 | Ala | Val | Met | Lys<br>400 | Ile | Ala | Val | Ala | Gly | Glu<br>405 |
| Leu | Phe | Gln | Leu | Glu<br>410 | Arg | Gly | Leu | Tyr | His<br>415 | Leu | Asn | Leu | Thr | Val<br>420 |
| Gly | Gly | Ile | Pro | Phe<br>425 | Lys | Glu | Ser | Glu | Leu<br>430 | Val | Gln | Pro | Ile | Asn<br>435 |
| Pro | Arg | Leu | Asp | Gly<br>440 | Cys | Met | Arg | Ser | Trp<br>445 | Asn | Trp | Leu | Asn | Gly<br>450 |
| Glu | Asp | Ser | Ala | Ile<br>455 | Gln | Glu | Thr | Val | Lys<br>460 | Ala | Asn | Thr | Lys | Met<br>465 |
| Gln | Cys | Phe | Ser | Val<br>470 | Thr | Glu | Arg | Gly | Ser<br>475 | Phe | Phe | Pro | Gly | Asn<br>480 |
| Gly | Phe | Ala | Thr | Tyr<br>485 | Arg | Leu | Asn | Tyr | Thr<br>490 | Arg | Thr | Ser | Leu | Asp<br>495 |
| Val | Gly | Thr | Glu | Thr<br>500 | Thr | Trp | Glu | Val | Lys<br>505 | Val | Val | Ala | Arg | Ile<br>510 |
| Arg | Pro | Ala | Thr | Asp<br>515 | Thr | Gly | Val | Leu | Leu<br>520 | Ala | Leu | Val | Gly | Asp<br>525 |
| Asp | Asp | Val | Val | Ile<br>530 | Ser | Val | Ala | Leu | Val<br>535 | Asp | Tyr | His | Ser | Thr<br>540 |
| Lys | Lys | Leu | Lys | Lys<br>545 | Gln | Leu | Val | Val | Leu<br>550 | Ala | Val | Glu | Asp | Val<br>555 |
| Ala | Leu | Ala | Leu | Met<br>560 | Glu | Ile | Lys | Val | Cys<br>565 | Asp | Ser | Gln | Glu | His<br>570 |
| Thr | Val | Thr | Val | Ser<br>575 | Leu | Arg | Glu | Gly | Glu<br>580 | Ala | Thr | Leu | Glu | Val<br>585 |
| Asp | Gly | Thr | Lys | Gly<br>590 | Gln | Ser | Glu | Val | Ser<br>595 | Thr | Ala | Gln | Leu | Gln<br>600 |
| Glu | Arg | Leu | Asp | Thr<br>605 | Leu | Lys | Thr | His | Leu<br>610 | Gln | Gly | Ser | Val | His<br>615 |
| Thr | Tyr | Val | Gly | Gly<br>620 | Leu | Pro | Glu | Val | Ser<br>625 | Val | Ile | Ser | Ala | Pro<br>630 |
| Val | Thr | Ala | Phe | Tyr<br>635 | Arg | Gly | Cys | Met | Thr<br>640 | Leu | Glu | Val | Asn | Gly<br>645 |
| Lys | Ile | Leu | Asp | Leu<br>650 | Asp | Thr | Ala | Ser | Tyr<br>655 | Lys | His | Ser | Asp | Ile<br>660 |
| Thr | Ser | His | Ser | Cys<br>665 | Pro | Pro | Val | Glu | His<br>670 | Ala | Thr | Pro<br>673 | | |

( 2 ) INFORMATION FOR SEQ ID NO:2:

( i ) SEQUENCE CHARACTERISTICS:
        ( A ) LENGTH: 678 amino acids
        ( B ) TYPE: amino acid
        ( D ) TOPOLOGY: linear ( x i ) SEQUENCE DESCRIPTION: SEQ ID NO:2:

| | | | | | | | | | | | | |
|---|---|---|---|---|---|---|---|---|---|---|---|---|
| Met<br>1 | Ala | Pro | Ser | Leu<br>5 | Ser | Pro | Gly | Pro | Ala<br>10 | Ala | Leu | Arg | Arg | Ala<br>15 |
| Pro | Gln | Leu | Leu | Leu<br>20 | Leu | Leu | Leu | Ala | Ala<br>25 | Glu | Cys | Ala | Leu | Ala<br>30 |
| Ala | Leu | Leu | Pro | Ala<br>35 | Arg | Glu | Ala | Thr | Gln<br>40 | Phe | Leu | Arg | Pro | Arg<br>45 |
| Gln | Arg | Arg | Ala | Phe<br>50 | Gln | Val | Phe | Glu | Glu<br>55 | Ala | Lys | Gln | Gly | His<br>60 |
| Leu | Glu | Arg | Glu | Cys | Val | Glu | Glu | Leu | Cys | Ser | Arg | Glu | Glu | Ala |

-continued

|  |  |  |  | 65 |  |  |  | 70 |  |  |  | 75 |
|---|---|---|---|---|---|---|---|---|---|---|---|---|
| Arg | Glu | Val | Phe | Glu | Asn | Asp | Pro | Glu | Thr | Asp | Tyr | Phe | Tyr | Pro |
|  |  |  |  | 80 |  |  |  | 85 |  |  |  | 90 |
| Arg | Tyr | Leu | Asp | Cys | Ile | Asn | Lys | Tyr | Gly | Ser | Pro | Tyr | Thr | Lys |
|  |  |  |  | 95 |  |  |  | 100 |  |  |  | 105 |
| Asn | Ser | Gly | Phe | Ala | Thr | Cys | Val | Gln | Asn | Leu | Pro | Asp | Gln | Cys |
|  |  |  |  | 110 |  |  |  | 115 |  |  |  | 120 |
| Thr | Pro | Asn | Pro | Cys | Asp | Arg | Lys | Gly | Thr | Gln | Ala | Cys | Gln | Asp |
|  |  |  |  | 125 |  |  |  | 130 |  |  |  | 135 |
| Leu | Met | Gly | Asn | Phe | Phe | Cys | Leu | Cys | Lys | Ala | Gly | Trp | Gly | Gly |
|  |  |  |  | 140 |  |  |  | 145 |  |  |  | 150 |
| Arg | Leu | Cys | Asp | Lys | Asp | Val | Asn | Glu | Cys | Ser | Gln | Glu | Asn | Gly |
|  |  |  |  | 155 |  |  |  | 160 |  |  |  | 165 |
| Gly | Cys | Leu | Gln | Ile | Cys | His | Asn | Lys | Pro | Gly | Ser | Phe | His | Cys |
|  |  |  |  | 170 |  |  |  | 175 |  |  |  | 180 |
| Ser | Cys | His | Ser | Gly | Phe | Glu | Leu | Ser | Ser | Asp | Gly | Arg | Thr | Cys |
|  |  |  |  | 185 |  |  |  | 190 |  |  |  | 195 |
| Gln | Asp | Ile | Asp | Glu | Cys | Ala | Asp | Ser | Glu | Ala | Cys | Gly | Glu | Ala |
|  |  |  |  | 200 |  |  |  | 205 |  |  |  | 210 |
| Arg | Cys | Lys | Asn | Leu | Pro | Gly | Ser | Tyr | Ser | Cys | Leu | Cys | Asp | Glu |
|  |  |  |  | 215 |  |  |  | 220 |  |  |  | 225 |
| Gly | Phe | Ala | Tyr | Ser | Ser | Gln | Glu | Lys | Ala | Cys | Arg | Asp | Val | Asp |
|  |  |  |  | 230 |  |  |  | 235 |  |  |  | 240 |
| Glu | Cys | Leu | Gln | Gly | Arg | Cys | Glu | Gln | Val | Cys | Val | Asn | Ser | Pro |
|  |  |  |  | 245 |  |  |  | 250 |  |  |  | 255 |
| Gly | Ser | Tyr | Thr | Cys | His | Cys | Asp | Gly | Arg | Gly | Gly | Leu | Lys | Leu |
|  |  |  |  | 260 |  |  |  | 265 |  |  |  | 270 |
| Ser | Gln | Asp | Met | Asp | Thr | Cys | Glu | Asp | Ile | Leu | Pro | Cys | Val | Pro |
|  |  |  |  | 275 |  |  |  | 280 |  |  |  | 285 |
| Phe | Ser | Val | Ala | Lys | Ser | Val | Lys | Ser | Leu | Tyr | Leu | Gly | Arg | Met |
|  |  |  |  | 290 |  |  |  | 295 |  |  |  | 300 |
| Phe | Ser | Gly | Thr | Pro | Val | Ile | Arg | Leu | Arg | Phe | Lys | Arg | Leu | Gln |
|  |  |  |  | 305 |  |  |  | 310 |  |  |  | 315 |
| Pro | Thr | Arg | Leu | Val | Ala | Glu | Phe | Asp | Phe | Arg | Thr | Phe | Asp | Pro |
|  |  |  |  | 320 |  |  |  | 325 |  |  |  | 330 |
| Glu | Gly | Ile | Leu | Leu | Phe | Ala | Gly | Gly | His | Gln | Asp | Ser | Thr | Trp |
|  |  |  |  | 335 |  |  |  | 340 |  |  |  | 345 |
| Ile | Val | Leu | Ala | Leu | Arg | Ala | Gly | Arg | Leu | Glu | Leu | Gln | Leu | Arg |
|  |  |  |  | 350 |  |  |  | 355 |  |  |  | 360 |
| Tyr | Asn | Gly | Val | Gly | Arg | Val | Thr | Ser | Ser | Gly | Pro | Val | Ile | Asn |
|  |  |  |  | 365 |  |  |  | 370 |  |  |  | 375 |
| His | Gly | Met | Trp | Gln | Thr | Ile | Ser | Val | Glu | Glu | Leu | Ala | Arg | Asn |
|  |  |  |  | 380 |  |  |  | 385 |  |  |  | 390 |
| Leu | Val | Ile | Lys | Val | Asn | Arg | Asp | Ala | Val | Met | Lys | Ile | Ala | Val |
|  |  |  |  | 395 |  |  |  | 400 |  |  |  | 405 |
| Ala | Gly | Asp | Leu | Phe | Gln | Pro | Glu | Arg | Gly | Leu | Tyr | His | Leu | Asn |
|  |  |  |  | 410 |  |  |  | 415 |  |  |  | 420 |
| Leu | Thr | Val | Gly | Gly | Ile | Pro | Phe | His | Glu | Lys | Asp | Leu | Val | Gln |
|  |  |  |  | 425 |  |  |  | 430 |  |  |  | 435 |
| Pro | Ile | Asn | Pro | Arg | Leu | Asp | Gly | Cys | Met | Arg | Ser | Trp | Asn | Trp |
|  |  |  |  | 440 |  |  |  | 445 |  |  |  | 450 |
| Leu | Asn | Gly | Glu | Asp | Thr | Thr | Ile | Gln | Glu | Thr | Val | Lys | Val | Asn |
|  |  |  |  | 455 |  |  |  | 460 |  |  |  | 465 |

```
Thr Arg Met Gln Cys Phe Ser Val Thr Glu Arg Gly Ser Phe Tyr
            470                 475                 480

Pro Gly Ser Gly Phe Ala Phe Tyr Ser Leu Asp Tyr Met Arg Thr
            485                 490                 495

Pro Leu Asp Val Gly Thr Glu Ser Thr Trp Glu Val Glu Val Val
            500                 505                 510

Ala His Ile Arg Pro Ala Ala Asp Thr Gly Val Leu Phe Ala Leu
            515                 520                 525

Trp Ala Pro Asp Leu Arg Ala Val Pro Leu Ser Val Ala Leu Val
            530                 535                 540

Asp Tyr His Ser Thr Lys Lys Leu Lys Lys Gln Leu Val Val Leu
            545                 550                 555

Ala Val Glu His Thr Ala Leu Ala Leu Met Glu Ile Lys Val Cys
            560                 565                 570

Asp Gly Gln Glu His Val Val Thr Val Ser Leu Arg Asp Gly Glu
            575                 580                 585

Ala Thr Leu Glu Val Asp Gly Thr Arg Gly Gln Ser Glu Val Ser
            590                 595                 600

Ala Ala Gln Leu Gln Glu Arg Leu Ala Val Leu Glu Arg His Leu
            605                 610                 615

Arg Ser Pro Val Leu Thr Phe Ala Gly Gly Leu Pro Asp Val Pro
            620                 625                 630

Val Thr Ser Ala Pro Val Thr Ala Phe Tyr Arg Gly Cys Met Thr
            635                 640                 645

Leu Glu Val Asn Arg Arg Leu Leu Asp Leu Asp Glu Ala Ala Tyr
            650                 655                 660

Lys His Ser Asp Ile Thr Ala His Ser Cys Pro Pro Val Glu Pro
            665                 670                 675

Ala Ala Ala
    678
```

( 2 ) INFORMATION FOR SEQ ID NO:3:

( i ) SEQUENCE CHARACTERISTICS:
        ( A ) LENGTH: 676 amino acids
        ( B ) TYPE: amino acid
        ( D ) TOPOLOGY: linear ( x i ) SEQUENCE DESCRIPTION: SEQ ID NO:3:

```
Met Arg Val Leu Gly Gly Arg Cys Gly Ala Leu Leu Ala Cys Leu
 1              5                  10                  15

Leu Leu Val Leu Pro Val Ser Glu Ala Asn Phe Leu Ser Lys Gln
            20                  25                  30

Gln Ala Ser Gln Val Leu Val Arg Lys Arg Ala Asn Ser Leu
            35                  40                  45

Leu Glu Glu Thr Lys Gln Gly Asn Leu Glu Arg Glu Cys Ile Glu
            50                  55                  60

Glu Leu Cys Asn Lys Glu Glu Ala Arg Glu Val Phe Glu Asn Asp
            65                  70                  75

Pro Glu Thr Asp Tyr Phe Tyr Pro Lys Tyr Leu Val Cys Leu Arg
            80                  85                  90

Ser Phe Gln Thr Gly Leu Phe Thr Ala Ala Arg Gln Ser Thr Asn
            95                  100                 105

Ala Tyr Pro Asp Leu Arg Ser Cys Val Asn Ala Ile Pro Asp Gln
            110                 115                 120

Cys Ser Pro Leu Pro Cys Asn Glu Asp Gly Tyr Met Ser Cys Lys
```

-continued

```
                         125                          130                          135
Asp Gly Lys Ala Ser Phe Thr Cys Thr Cys Lys Pro Gly Trp Gln
                140                          145                          150
Gly Glu Lys Cys Glu Phe Asp Ile Asn Glu Cys Lys Asp Pro Ser
                155                          160                          165
Asn Ile Asn Gly Gly Cys Ser Gln Ile Cys Asp Asn Thr Pro Gly
                170                          175                          180
Ser Tyr His Cys Ser Cys Lys Asn Gly Phe Val Met Leu Ser Asn
                185                          190                          195
Lys Lys Asp Cys Lys Asp Val Asp Glu Cys Ser Leu Lys Pro Ser
                200                          205                          210
Ile Cys Gly Thr Ala Val Cys Lys Asn Ile Pro Gly Asp Phe Glu
                215                          220                          225
Cys Glu Cys Pro Glu Gly Tyr Arg Tyr Asn Leu Lys Ser Lys Ser
                230                          235                          240
Cys Glu Asp Ile Asp Glu Cys Ser Glu Asn Met Cys Ala Gln Leu
                245                          250                          255
Cys Val Asn Tyr Pro Gly Gly Tyr Thr Cys Tyr Cys Asp Gly Lys
                260                          265                          270
Lys Gly Phe Lys Leu Ala Gln Asp Gln Lys Ser Cys Glu Val Val
                275                          280                          285
Ser Val Cys Leu Pro Leu Asn Leu Asp Thr Lys Tyr Glu Leu Leu
                290                          295                          300
Tyr Leu Ala Glu Gln Phe Ala Gly Val Val Leu Tyr Leu Lys Phe
                305                          310                          315
Arg Leu Pro Glu Ile Ser Arg Phe Ser Ala Glu Phe Asp Phe Arg
                320                          325                          330
Thr Tyr Asp Ser Glu Gly Val Ile Leu Tyr Ala Glu Ser Ile Asp
                335                          340                          345
His Ser Ala Trp Leu Leu Ile Ala Leu Arg Gly Gly Lys Ile Glu
                350                          355                          360
Val Gln Leu Lys Asn Glu His Thr Ser Lys Ile Thr Thr Gly Gly
                365                          370                          375
Asp Val Ile Asn Asn Gly Leu Trp Asn Met Val Ser Val Glu Glu
                380                          385                          390
Leu Glu His Ser Ile Ser Ile Lys Ile Ala Lys Glu Ala Val Met
                395                          400                          405
Asp Ile Asn Lys Pro Gly Pro Leu Phe Lys Pro Glu Asn Gly Leu
                410                          415                          420
Leu Glu Thr Lys Val Tyr Phe Ala Gly Phe Pro Arg Lys Val Glu
                425                          430                          435
Ser Glu Leu Ile Lys Pro Ile Asn Pro Arg Leu Asp Gly Cys Ile
                440                          445                          450
Arg Ser Trp Asn Leu Met Lys Gln Gly Ala Ser Gly Ile Lys Glu
                455                          460                          465
Ile Ile Gln Glu Lys Gln Asn Lys His Cys Leu Val Thr Val Glu
                470                          475                          480
Lys Gly Ser Tyr Tyr Pro Gly Ser Gly Ile Ala Gln Phe His Ile
                485                          490                          495
Asp Tyr Asn Asn Val Ser Ser Ala Glu Gly Trp His Val Asn Val
                500                          505                          510
Thr Leu Asn Ile Arg Pro Ser Thr Gly Thr Gly Val Met Leu Ala
                515                          520                          525
```

| | | | | | | | | | | | | |
|---|---|---|---|---|---|---|---|---|---|---|---|---|
|Leu|Val|Ser|Gly|Asn<br>530|Asn|Thr|Val|Pro|Phe<br>535|Ala|Val|Ser|Leu|Val<br>540|
|Asp|Ser|Thr|Ser|Glu<br>545|Lys|Ser|Gln|Asp|Ile<br>550|Leu|Leu|Ser|Val|Glu<br>555|
|Asn|Thr|Val|Ile|Tyr<br>560|Arg|Ile|Gln|Ala|Leu<br>565|Ser|Leu|Cys|Ser|Asp<br>570|
|Gln|Gln|Ser|His|Leu<br>575|Glu|Phe|Arg|Val|Asn<br>580|Arg|Asn|Asn|Leu|Glu<br>585|
|Leu|Ser|Thr|Pro|Leu<br>590|Lys|Ile|Glu|Thr|Ile<br>595|Ser|His|Glu|Asp|Leu<br>600|
|Gln|Arg|Gln|Leu|Ala<br>605|Val|Leu|Asp|Lys|Ala<br>610|Met|Lys|Ala|Lys|Val<br>615|
|Ala|Thr|Tyr|Leu|Gly<br>620|Gly|Leu|Pro|Asp|Val<br>625|Pro|Phe|Ser|Ala|Thr<br>630|
|Pro|Val|Asn|Ala|Phe<br>635|Tyr|Asn|Gly|Cys|Met<br>640|Glu|Val|Asn|Ile|Asn<br>645|
|Gly|Val|Gln|Leu|Asp<br>650|Leu|Asp|Glu|Ala|Ile<br>655|Ser|Lys|His|Asn|Asp<br>660|
|Ile|Arg|Ala|His|Ser<br>665|Cys|Pro|Ser|Val|Trp<br>670|Lys|Lys|Thr|Lys|Asn<br>675|

Ser
676

( 2 ) INFORMATION FOR SEQ ID NO:4:

( i ) SEQUENCE CHARACTERISTICS:
( A ) LENGTH: 1872 bases
( B ) TYPE: nucleic acid
( C ) STRANDEDNESS: single
( D ) TOPOLOGY: linear ( x i ) SEQUENCE DESCRIPTION: SEQ ID NO:4:

```
GAATTCGGGA CAGCCTCTCC TGCCGCCGCT GCTGCTGCCG CCGCCGCCAC  50
CGCCGGCTGG TCCTCCTTCT GCTTTTACTT CTCCTGCATG ACAGTTGTTT 100
TCTTCATCTG AGCAGACACC AGCTTCAGAT GCTCGAGGTG AGAAACATGC 150
CTTTCAGTTT GGGCTACTGG TTTACTTAAT TAATCAGCCG GCAGCTCCGT 200
CGATCTATTT TCGTCCCTGT CCTCTTGACG AGCCCGGGAT GGTTTGGAGT 250
AGCATTTAAA AGAACTAGAA AAGTGGCCCA GAAACAGCAG CTTAAAGAAT 300
TATTACGATA TACTTTGATT TTGTAGTTGC TAGGAGCTTT TCTTCCCCCC 350
TTGCATCTTT CTGAACTCTT CTTGATTTTA ATAATGGCCT TGGACTTGGA 400
CGATTTATCG ATTTCCCCCT GTAAGATGCT GTATCATTTG GTTGGGGGGG 450
CCTCTGCGTG GTAATGGACC GTGAGAGCGG CCAGGCCTTC TTCTGGAGGT 500
GAGCCGATGG AGATTTATTC CCCAGACATG TCTGAGGTCG CCGCCGAGAG 550
GTCCTCCAGC CCCTCCACTC AGCTGAGTGC AGACCCATCT CTTGATGGGC 600
TTCCGGCAGC AGAAGACATG CCAGAGCCCC AGACTGAAGA TGGGAGAACC 650
CCTGGACTCG TGGGCCTGGC CGTGCCCTGC TGTGCGTGCC TAGAAGCTGA 700
GCGCCTGAGA GGTTGCCTCA ACTCAGAGAA AATCTGCATT GTCCCCATCC 750
TGGCTTGCCT GGTCAGCCTC TGCCTCTGCA TCGCCGGCCT CAAGTGGGTA 800
TTTGTGGACA AGATCTTTGA ATATGACTCT CCTACTCACC TTGACCCTGG 850
GGGGTTAGGC CAGGACCCTA TTATTTCTCT GGACGCAACT GCTGCCTCAG 900
```

-continued

```
CTGTGTGGGT GTCGTCTGAG GCATACACTT CACCTGTCTC TAGGGCTCAA  950
TCTGAAAGTG AGGTTCAAGT TACAGTGCAA GGTGACAAGG CTGTTGTCTC 1000
CTTTGAACCA TCAGCGGCAC CGACACCGAA GAATCGTATT TTTGCCTTTT 1050
CTTTCTTGCC GTCCACTGCG CCATCCTTCC CTTCACCCAC CCGGAACCCT 1100
GAGGTGAGAA CGCCCAAGTC AGCAACTCAG CCACAAACAA CAGAAACTAA 1150
TCTCCAAACT GCTCCTAAAC TTTCTACATC TACATCCACC ACTGGGACAA 1200
GCCATCTTGT AAAATGTGCG GAGAAGGAGA AAACTTTCTG TGTGAATGGA 1250
GGGGAGTGCT TCATGGTGAA AGACCTTTCA AACCCCTCGA GATACTTGTG 1300
CAAGTGCCCA AATGAGTTTA CTGGTGATCG CTGCCAAAAC TACGTAATGG 1350
CCAGCTTCTA CAGTACGTCC ACTCCCTTTC TGTCTCTGCC TGAATAGGAG 1400
CATGCTCAGT TGGTGCTGCT TTCTTGTTGC TGCATCTCCC CTCAGATTCC 1450
ACCTAGAGCT AGATGTGTCT TACCAGATCT AATATTGACT GCCTCTGCCT 1500
GTCGCATGAG AACATTAACA AAAGCAATTG TATTACTTCC TCTGTTCGCG 1550
ACTAGTTGGC TCTGAGATAC TAATAGGTGT GTGAGGCTCC GGATGTTTCT 1600
GGAATTGATA TTGAATGATG TGATACAAAT TGATAGTCAA TATCAAGCAG 1650
TGAAATATGA TAATAAAGGC ATTTCAAAGT CTCACTTTTA TTGATAAAAT 1700
AAAAATCATT CTACTGAACA GTCCATCTTC TTTATACAAT GACCACATCC 1750
TGAAAAGGGT GTTGCTAAGC TGTAACCGAT ATGCACTTGA AATGATGGTA 1800
AGTTAATTTT GATTCAGAAT GTGTTATTTG TCACAAATAA ACATAATAAA 1850
AGGAAAAAAA AAACCCGAAT TC 1872
```

( 2 ) INFORMATION FOR SEQ ID NO:5:

( i ) SEQUENCE CHARACTERISTICS:
        ( A ) LENGTH: 296 amino acids
        ( B ) TYPE: amino acid
        ( D ) TOPOLOGY: linear ( x i ) SEQUENCE DESCRIPTION: SEQ ID NO:5:

```
Met Glu Ile Tyr Ser Pro Asp Met Ser Glu Val Ala Ala Glu Arg
 1               5                  10                  15

Ser Ser Ser Pro Ser Thr Gln Leu Ser Ala Asp Pro Ser Leu Asp
                20                  25                  30

Gly Leu Pro Ala Ala Glu Asp Met Pro Glu Pro Gln Thr Glu Asp
                35                  40                  45

Gly Arg Thr Pro Gly Leu Val Gly Leu Ala Val Pro Cys Cys Ala
                50                  55                  60

Cys Leu Glu Ala Glu Arg Leu Arg Gly Cys Leu Asn Ser Glu Lys
                65                  70                  75

Ile Cys Ile Val Pro Ile Leu Ala Cys Leu Val Ser Leu Cys Leu
                80                  85                  90

Cys Ile Ala Gly Leu Lys Trp Val Phe Val Asp Lys Ile Phe Glu
                95                 100                 105

Tyr Asp Ser Pro Thr His Leu Asp Pro Gly Gly Leu Gly Gln Asp
               110                 115                 120

Pro Ile Ile Ser Leu Asp Ala Thr Ala Ala Ser Ala Val Trp Val
               125                 130                 135

Ser Ser Glu Ala Tyr Thr Ser Pro Val Ser Arg Ala Gln Ser Glu
               140                 145                 150
```

| | | | | | | | | | | | | | |
|---|---|---|---|---|---|---|---|---|---|---|---|---|---|
|Ser|Glu|Val|Gln|Val|Thr|Val|Gln|Gly|Asp|Lys|Ala|Val|Val|Ser|
| | | | |155| | | |160| | | | |165|
|Phe|Glu|Pro|Ser|Ala|Ala|Pro|Thr|Pro|Lys|Asn|Arg|Ile|Phe|Ala|
| | | | |170| | | |175| | | | |180|
|Phe|Ser|Phe|Leu|Pro|Ser|Thr|Ala|Pro|Ser|Phe|Pro|Ser|Pro|Thr|
| | | | |185| | | |190| | | | |195|
|Arg|Asn|Pro|Glu|Val|Arg|Thr|Pro|Lys|Ser|Ala|Thr|Gln|Pro|Gln|
| | | | |200| | | |205| | | | |210|
|Thr|Thr|Glu|Thr|Asn|Leu|Gln|Thr|Ala|Pro|Lys|Leu|Ser|Thr|Ser|
| | | | |215| | | |220| | | | |225|
|Thr|Ser|Thr|Thr|Gly|Thr|Ser|His|Leu|Val|Lys|Cys|Ala|Glu|Lys|
| | | | |230| | | |235| | | | |240|
|Glu|Lys|Thr|Phe|Cys|Val|Asn|Gly|Gly|Glu|Cys|Phe|Met|Val|Lys|
| | | | |245| | | |250| | | | |255|
|Asp|Leu|Ser|Asn|Pro|Ser|Arg|Tyr|Leu|Cys|Lys|Cys|Pro|Asn|Glu|
| | | | |260| | | |265| | | | |270|
|Phe|Thr|Gly|Asp|Arg|Cys|Gln|Asn|Tyr|Val|Met|Ala|Ser|Phe|Tyr|
| | | | |275| | | |280| | | | |285|
|Ser|Thr|Ser|Thr|Pro|Phe|Leu|Ser|Leu|Pro|Glu| | | | |
| | | | |290| | | |295|296| | | | | |

( 2 ) INFORMATION FOR SEQ ID NO:6:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( x i ) SEQUENCE DESCRIPTION: SEQ ID NO:6:

GATATCGATC CATGGCCCCT TCGCTCTC 28

( 2 ) INFORMATION FOR SEQ ID NO:7:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( x i ) SEQUENCE DESCRIPTION: SEQ ID NO:7:

CATGGATCCT ACCGGAAGTC AAACTCAGCT A 31

( 2 ) INFORMATION FOR SEQ ID NO:8:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( x i ) SEQUENCE DESCRIPTION: SEQ ID NO:8:

GATATCGATG AGTGTGAAGT CCTTGTAC 28

( 2 ) INFORMATION FOR SEQ ID NO:9:

( i ) SEQUENCE CHARACTERISTICS:
        ( A ) LENGTH: 27 bases
        ( B ) TYPE: nucleic acid ( C ) STRANDEDNESS: single
( D ) TOPOLOGY: linear ( x i ) SEQUENCE DESCRIPTION: SEQ ID NO:9:

GTCGGATCCG ACAGAGACTG AGAAGCC 27

ISOLATING AND CULTURING SCHWANN CELLS

BACKGROUND OF THE INVENTION

1. Field of the Invention

This invention relates to a method for isolating and culturing Schwann cells, to the isolated Schwann cells per se and to uses thereof In particular, the invention provides a method for enhancing the survival and proliferation of human Schwann cells by culturing them in serum free culture medium supplemented with a Rse/Axl receptor activator and other mitogenic agents.

2. Description of Related Art

1. Schwann cells

Schwann cells are the principal support cells in the peripheral nervous system. The cells originate from the neural crest during early embryonic development and migrate with the extending axons of the nerve into the periphery. During this phase, Schwann cells undergo rapid proliferation to produce an adequate number of cells to accommodate the growing axons. Subsequently, Schwann cells become terminally differentiated by ensheathing or myelinating the axons and then remain quiescent during adult life. However, Schwann cell proliferation can be stimulated under pathological conditions and plays a crucial role in nerve regeneration following injury. When a peripheral nerve is transected, Schwann cells at the site of the injury begin to demyelinate and reenter the cell cycle (Bunge, Current Opin. in Neurobiol. 3:805 [1993]). The proliferating Schwann cells produce neurotropic factors and extracellular matrix proteins to guide or facilitate the regrowth of the transected axons and finally complete the process of regeneration by remyelinating the regenerated axons.

The remarkable capacity of Schwann cells to promote nerve fiber regeneration, in both the peripheral and central nervous system, has been demonstrated by peripheral nerve graft (Paino and Bunge, Experimental Neurology 114:254 [1991]) and the implantation of guidance channels impregnated with Schwann cells (Guénard et al., J. Neuroscience 12(9):3310 [1992] and Paino et al., J. Neurocytol. 23:433 [1994]). A cellular prosthesis containing human Schwann cells has been proposed for clinical applications such as transplantation to the site of spinal cord injury to influence the regeneration of central axons and to repair complex peripheral nerve injuries containing lengthy gaps (Levi et al., J. Neuroscience 14(3):1309 [1994]). The clinical success of these procedures, which use autologous Schwann cells, depends on the ability to expand in vitro a pure Schwann cell population starting from material in a small biopsy.

Several reports have described techniques for culturing rat Schwann cells. See Brockes et al., Brain Research 165: 105–118 (1979); Brockes et al., J. Biol. Chem. 255(18):8374–8377 (1980); Brockes et al., Ann. Neurol. 20(3):317–322 (1986); Brockes, J., Methods in Enzym. 147:217–225 (1987); Morrissey et al., J. Neuroscience 11(8):2433–2442 (1991); Paino and Bunge, Experimental Neurology 114:254 (1991); Guenard et al., J. Neuroscience 12(9):3310–3320 (1992); Peulve et al., Exper. Cell Res. 214:543–550 (1994); Li et al., J. Neuroscience 14(7):4050–4063 (1994); Collier and Martin, Exper. Neurol. 124:129–133 (1993); Scherer et al. J. Neuroscience Res. 38:575–589 (1994); Yamamoto et al., Brain Res. 653:335–339 (1994); Morgan et al. Development 120:1399–1409 (1994); Paino et al. J. Neurocytol. 23:433–452 (1994); Messing et al., J. Neurosci. 14:3533–3539 (1994); Haynes et al., J. Neurosci. Methods 52:119–127 (1994); WO 92/03536; WO 92/18627; WO 94/00140; and WO 94/04560.

Watabe et al., J. Neurosci. Res. 39:525–534 (1994) studied the mitogenic effects of platelet-derived growth factor, fibroblast growth factor, transforming growth factor-β, and heparin-binding serum factor on adult mouse Schwann cells in cell culture.

Recently, techniques for culturing human Schwann cells have been described. See Rutkowski et al., Ann. Neurol. 31(6):580–586 (1992); Levi et al., J. Neuroscience 14(3) 1309–1319 (1994); and Levi et al., J. Neuroscience 15(2): 1329–1340 (1995).

Traditionally, Schwann cells have been grown in culture medium supplemented with serum. Fibroblasts are a major contaminant of these preparations, particularly when adult tissues are used, and will overgrow the Schwann cells. The fibroblast population varies with the time in the culture (Levi et al., J. Neuroscience 14(3): 1309 [1994]), or is reduced through laborious protocols such as sequential outgrowth (Morrissey et al., J. Neuroscience 11(8):2433–2442 [1991]), antibody selection (Brockes, J., Methods in Enzym. 147:217–225 [1987] and Watabe et al., J. Neurosci. Res. 39:525–534 [1994]) or use of anti-mitotic agents (Levi et al., J. Neuroscience 15(2): 1329–1340 [1995]).

2. Rse and Axl receptors

Mark et al. recently described the human and murine complementary DNA sequences of the receptor tyrosine kinase Rse that is preferentially expressed in the adult brain (Mark et al. J. Biol. Chem. 269:10720 [1994]). The extracellular domain of Rse receptor is composed of two immunoglobulin-like (Ig-L) repeats followed by two fibronectin type III repeats. Complementary DNA sequences encoding proteins identical to human (Ohashi et al., Oncogene 9:699 [1994]) and murine Rse (Lai et al., Oncogene 9:2567 [1994]) have been reported independently, and termed Sky and Tyro3, respectively. See also Fujimoto and Yamamoto Oncogene 9:693 (1994) concerning the murine equivalent to Rse they call brt and Dai et al. Oncogene 9:975 (1994) with respect to the human molecule they call tif.

The expression of Rse in various tissues has been investigated. Lai et al., Oncogene 9:2567 [1994], found that, in the adult brain, Rse mRNA is localized in neurons of the neocortex, cerebellum and hippocampus. Schulz et al. similarly found that Rse is expressed at high levels in the cerebral cortex, the lateral septum, the hippocampus, the olfactory bulb and in the cerebellum. The highest levels of Rse expression in the brain were found to be associated with neurons. (Schulz et al. Molec. Brain Res. 28:273–280 [1995]). In the central nervous system (CNS) of mice, the expression of Rse was detected at highest levels during late embryonic gages and post birth, coincident with the establishment and maintenance of synaptic circuitry in conical and hippocampal neurons (Lai et al., Oncogene 9:2567 [1994] and Schneider et al., Cell 54:787–793 [1988]). This process is believed to be regulated locally, by cells that are in direct contact or positioned close to one another.

Rse is structurally related to Axl (also known as Ufo or Ark) and shares 43% overall amino acid sequence identity with this tyrosine kinase receptor. See O'Bryan et al., Mol. Cell. Biol. 11:5016 (1991), Janssen et al., Oncogene 6:2113 (1991), Rescigno et al. Oncogene 5:1908 (1991) and Bellosta et al. 15:614 (1995) concerning Axl. Rse and Axl, together with c-Mer (Graham et al., Cell Growth Differ. 5:647 [1994]), define a class of receptor tyrosine kinases whose extracellular domains resemble neural cell recognition and adhesion molecules (reviewed by Ruitishauser, U.

in *Current Opin. Neurobiology* 3:709 [1993] and Brummendorf and Rathjen in *J. Neurochemistry* 61:1207 [1993]). Like Rse, Axl is also expressed in the nervous system, but is more widely expressed than Rse in peripheral tissues.

Putative ligands for the Rse and Axl receptors have been reported. Varnum et al. *Nature* 373:623 (1995) and Stitt et al., *Cell* 80:661-670 (1995) recently reported that gas6 (for growth arrest-specific gene 6) is a ligand for Axl. Gas6 belongs to a set of murine genes which are highly expressed during serum starvation in NIH 3T3 cells (Schneider et al., *Cell* 54:787-793 [1988]). These genes were designated growth arrest-specific genes, since their expression is negatively regulated during growth induction. The human homolog of murine gas6 was also cloned and sequenced by Manfioletti et al. in *Molec. Cell Biol.* 13(8):4976-4985 (1993). They concluded that gas6 is a vitamin K-dependent protein and speculated that it may play a role in the regulation of a protease cascade relevant in growth regulation. Gas6 is expressed in a variety of tissues including the brain. See also Colombo et al. *Genome* 2:130-134 (1992) and Ferrero et al. *J. Cellular Physiol.* 158:263-269 (1994) concerning gas6.

Stitt et al., *Cell* 80:661-670 (1995) further reported that protein S is the ligand for Tyro3. Protein S is a vitamin K-dependent plasma protein that functions as an anticoagulant by acting as a cofactor to stimulate the proteolytic inactivation of factors Va and VIIIa by activated protein C. Reviewed in Esmon et al. *Aterioscler. Thromb.* 12:135 (1992). Accordingly, protein S is an important negative regulator of the blood-clotting cascade. See Walker et al., *J. Biol. Chem.* 255:5521-5524(1980), Walker et al., *J. Biol. Chem.* 256:11128-11131 (1981), Walker et al., *Arch. Biochem. Biophys.* 252:322-328 (1991), Griffin et al. *Blood* 79:3203 (1992) and Easmon, D., *Aterioscler. Thromb.* 12:135 (1992). The discovery that about half of the protein S in human plasma is bound to C4BP further supports the notion that protein S is involved in the complement cascade. Dahlback et al., *PNAS(USA)* 78:2512-2516 (1981). The role of protein S as a mitogen for smooth muscle cells has also been reported. Gasic et al., *PNAS(USA)* 89:2317-2320 (1992).

Protein S can be divided into four domains (see FIGS. 1A, 1C and 1D herein). Residues 1-52 (Region A) are rich in γ-carboxyglutamic acid (Gla) residues which mediate the $Ca^{2+}$ dependent binding of protein S to negatively charged phospholipids (Walker, *J. Biol. Chem.* 259:10335 [1984]). Region B includes a thrombin-sensitive loop. Region C contains four epidermal growth factor (EGF)-like repeats. Region D is homologous to the steroid hormone binding globulin (SHBG) protein (Hammond et al., *FEBS Lett.* 215:100 [1987]). As discussed by Joseph and Baker (*FASEB J.* 6:2477 [1994]), this region is homologous to domains in the A chain of laminin (23% identity) and merosin (22% identity) and to a domain in the Drosophila crumbs (19%).

Murine and human gas6 cDNAs encode proteins having 43 and 44% amino acid sequence identity respectively to human protein S.

SUMMARY OF THE INVENTION

This application discloses the use of a defined, serum-free culture system which will not support fibroblast growth or survival (despite the absence of fibroblast-specific inhibitory factor(s) in the preferred culture medium) and yields substantially homogenous Schwann cell cultures. Gas6 is demonstrated to be a potent growth/survival factor for Schwann cells in defined, serum free culture. The synergistic effect of gas6 with forskolin and heregulin, enables the efficient expansion of a pure Schwann cell population in defined medium.

Accordingly, the invention can be said to relate to a method for enhancing the survival and/or proliferation of Schwann cells (especially human Schwann cells) in cell culture comprising culturing the Schwann cells in serum free culture medium, wherein the culture medium comprises a Rse/Axl receptor activator (e.g. gas6) and a second mitogenic agent (e.g. heregulin). The Rse/Axl receptor activator and second mitogenic agent are each present in an amount effective to enhance survival or proliferation of the Schwann cells. Preferably, the Schwann cells are cultured in a laminin-coated culture plate. The method can be used to enhance survival and/or proliferation of Schwann cells derived from an adult patient, thus facilitating autologous transplants into the patient.

The invention further provides a serum free culture medium for culturing Schwann cells, which medium comprises a Rse/Axl receptor activator and a second mitogenic agent (e.g. heregulin). Optionally, the culture medium also comprises an agent which elevates cAMP levels in the culture medium (e.g. forskolin); an iron source (e.g. transferrin); insulin or an insulin like growth factor (e.g. IGF-I or IGF-II); a vitamin (e.g. Vitamin E); and a protease inhibitor.

The invention also provides a method for isolating Schwann cells comprising: (a) pre-incubating nerve tissue containing the Schwann cells in culture medium, where the culture medium comprises a mitogenic agent, for a sufficient period of time such that demyelination of the Schwann cells occurs; and (b) culturing the demyelinated Schwann cells in the culture medium of the preceding paragraph.

The invention also relates to a composition comprising human Schwann cells and a pharmaceutically acceptable carrier, wherein the composition is essentially free of serum. In addition, a composition comprising human Schwann cells in serum free culture medium is provided wherein the culture medium further comprises a mitogenic factor.

The Schwann cells isolated as dislosed herein can be used in a method of treating a mammal (e.g. one which has suffered a nervous system injury), which method involves administering to the mammal an effective mount of human Schwann cells which have been cultured according to the procedures disclosed herein. Accordingly, the invention provides a method of promoting nervous system repair in a mammal comprising transplanting Schwann cells which have been isolated and cultured using the techniques disclosed herein into a region of injury in the central or peripheral nervous system of the mammal.

BRIEF DESCRIPTION OF THE DRAWINGS

FIGS. 1A-1D provide a schematic representation of the structures of protein S and gas6 (FIG. 1A) and comparison of the amino acid homology between the bovine (b) and human (h) forms of protein S (FIGS. 1C and 1D, respectively) with human gas6 (FIG. 1B). For h gas6, boxes represent the Gla region (i.e. the A domain), the loop region (i.e. the B domain), the 4 EGF-like repeats (labeled $C_1$–$C_4$) which form the C domain, and the region homologous to sex-hormone binding globulin (i.e. the D domain), which is also related to the G domains of laminin A chain and merosin and to Drosphilia crumbs protein. The percentage of amino acid identity shared between h gas6 and either b protein S or h protein S is indicated within the corresponding boxes. The amino acids at the boundaries of each of the regions are indicated above the boxes.

FIG. 2 shows a comparison of the amino acid sequences of murine gas6 (m gas6) [SEQ ID NO: 1], h gas6 [SEQ ID NO: 2] and h protein S [SEQ ID NO: 3]. Residues of the "pre" and "pro" sequences are indicated (with the arrow indicating the last residue of each precursor sequence). The A–D domains are delineated, as are the two G domains which reside in the D domain (i.e. G domain 1 and G domain 2).

FIG. 3 depicts the cDNA sequence [SEQ ID NO: 4] and deduced amino acid sequence [SEQ ID NO: 5] of sensory and motor neuron derived factor (SMDF). The EGF-like domain and the apolar and uncharged domains (i.e. "apolar I" consisting of residues from about 48–62 and "apolar II" consisting of residues from about 76–100) are underlined. Cysteines are boxed. The stop codon is denoted by the letter "O".

FIGS. 4A–4B depict dose response of forskolin in embryonic (ESC) and adult (ASC) Schwann cell lines. ESC of passage 21 and ASC cells of passage 16 were inoculated at $1.4 \times 10^4$ cells/well and $3.1 \times 10^4$ cells/well respectively in 12 well plates in "7F" medium: F12/DMEM containing bovine pituitary extract (BPE) (2 µg/ml), insulin (10 µg/ml), heregulin (1 nM), Vitamin E (5 µg/ml), progesterone (3 nM), transferrin (10 µg/ml), forskolin (5 µM) and gentamycin. Wells were coated with laminin. Forskolin was omitted initially then added at the indicated concentrations. Duplicate wells of cells for each condition were counted with a Coulter™ counter on day 5 of culture. Values shown are the mean and standard deviation for each condition.

FIGS. 5A–B depict dose response of heregulin in ESC and ASC (passage 21) cell lines. Cells were inoculated at $2.1 \times 10^4$ cells/well and $2.2 \times 10^4$ cells/well, respectively, in 12 well plates in F12/DMEM. Medium was supplemented with 7F as described for FIGS. A–B and all webs were coated with laminin. Recombinant human heregulin was omitted initially then added at the indicated concentrations. Duplicate wells of cells for each condition were counted with a Coulter™ counter on day 5 of culture.

FIGS. 6A–B depict dose response of bovine pituitary extract (BPE) in ESC and ASC cell lines at passage 21 and 16, respectively. Cells were inoculated at $1.7 \times 10^4$ cells/well and $3.1 \times 10^4$ cells/well, respectively, in 12 well plates in F12/DMEM. Medium was supplemented with 7F as described for FIGS. 4A–B and all webs were coated with laminin. Bovine pituitary extract (BPE) was omitted initially then added at the indicated concentrations. Duplicate wells of cells for each condition were counted with a Coulter™ counter on day 5 of culture.

FIGS. 7A–F depict dose response of insulin (FIGS. 7A–B), IGF-I (FIGS. 7C–D), and IGF-II (FIGS. 7E–F) in ESC and ASC cell lines. ESC and ASC cells between passages 16 and 30, were inoculated at $1.3 \times 10^4$ cells/well (except $3.1 \times 10^4$ cells/well in 7B) in 12 well plates in F12/DMEM. Medium was supplemented with 7F as described for FIGS. 4A–B and all webs were coated with laminin unless otherwise noted. Recombinant human insulin was omitted initially then insulin, IGF-I or IGF-II were added at the indicated concentrations. Duplicate wells of cells for each condition were counted with a Coulter™ counter on day 5 of culture FIGS. 8A–8C depict the effect of gas6 and other growth factors on human Schwann cell growth and DNA synthesis. All data are presented as mean ± standard error (n=4). FIG. 8A shows dose responsive curves of human Schwann cells to gas6 in different conditions. Medium "6F" is F12/DME supplemented with insulin (10 µg/ml), transferrin (10 µg/ml), Vitamin E (5 µml), chemically defined lipids (50 µg/ml), aproteinin (25 µg/ml) and progesterone ($3 \times 10^{-8}$M).

Medium "8SF" is "6F" medium with the addition of forskolin (5 µM) and heregulin (10 nm). Cell numbers were counted with Coulter™ counter at 84 hours after culture with the indicated concentrations of gas6. FIG. 8B shows that gas6 increased thymidine incorporation in Schwann cells cultured as in FIG. 8A in the presence of different concentrations of gas6. $^3$H-[methyl]-thymidine (0.5 µCi/ml) was added at 48 hours of culture. Cells were harvested at 96 hours of culture and processed for measurement of the radioactivity incorporated in DNA. FIG. 8C shows the influence of growth factors on Schwann cell growth in the presence of 8F medium. Schwann cells were plated in 8F medium with or without PDGF (10 ng/ml), basic FGF (20 ng/ml), IL-1α(1 ng/ml), TGF-β1 (1 ng/ml) and gas6 (30 ng/ml). Cell numbers were counted after 108 hours.

FIG. 9 illustrates a time course of human Schwann cell growth in culture. Human Schwann cells were plated at $2 \times 10^4$ cells/well in 24 well multiplates in F12/DME medium (1:1) supplemented with 8F with or without gas6 or 10% dia-filtered fetal bovine serum (FBS). Four wells of cultures were taken from each group for cell counting every 24 hours. Data shown are mean ± standard error (n=4).

FIGS. 10A–10D are phase contrast micrographs of human Schwann cells grown in 6F+heregulin (FIG. 10A), 6F+heregulin+gas6 (FIG. 10B), 8F+gas6 (FIG. 10C) and 8F+10% fetal bovine serum (FIG. 10D). Micrographs were taken after 96 hours of culture.

DETAILED DESCRIPTION OF THE PREFERRED EMBODIMENTS

I. Definitions

In general, the following words or phrases have the indicated definition when used in the description, examples, and claims:

A "Schwann cell" is a cell of neural crest origin that forms a continuous envelope around each nerve fiber of peripheral nerves in situ. A Schwann cell can be identified as such by detecting the presence of one or more Schwann cell markers such as glial fibrillar acidic protein (GFAP), S100 protein, laminin, or nerve growth factor (NGF) receptor, e.g., using antibodies against these markers. Furthermore, Schwann cells have a characteristic morphology which can be detected by microscopic examination of cultures thereof. See Example 2 (iv). Isolated Schwann cells can also be evaluated for the maintenance of differentiated Schwann cell functions, such as the ability to associate with sensory neurons in culture or the ability to produce myelin or myelin related proteins such as Po and myelin associated glycoprotein (MAG). To study this, the isolated Schwann cells can be seeded onto a substantially pure population of sensory neurons in culture and cell interactions and protein production can be observed over a period of several weeks.

The term "cell culture medium" and "culture medium" refer to a nutrient solution used for growing mammalian cells that typically provides at least one component from one or more of the following categories:

1) an energy source, usually in the form of a carbohydrate such as glucose;
2) all essential amino acids, and usually the basic set of twenty amino acids plus cystine;
3) vitamins and/or other organic compounds required at low concentrations;
4) free fatty acids; and
5) trace elements, where trace elements are defined as inorganic compounds or naturally occurring elements that are typically required at very low concentrations, usually in the micromolar range.

The nutrient solution may optionally be supplemented with one or more components from any of the following categories:

1) one or more mitogenic agents;
2) salts and buffers as, for example, calcium, magnesium, and phosphate;
3) nucleosides and bases such as, for example, adenosine and thymidine, hypoxanthine; and
4) protein and tissue hydrolysates.

The terms "amino acids" and "amino acid" refer to all naturally occurring a amino acids in both their D and L stereoisomeric forms, and their analogs and derivatives. An analog is defined as a substitution of an atom in the amino acid with a different atom that usually has similar properties. A derivative is defined as an amino add that has another molecule or atom attached to it. Derivatives would include, for example, acetylation of an amino group, amination of a carboxyl group, or oxidation of the sulfur residues of two cysteine molecules to form cystine.

The cell culture medium is generally "serum free", which means that the medium is essentially flee of serum from any mammalian source (e.g. fetal bovine serum [FBS]). By "essentially free" is meant that the cell culture medium comprises between about 0–5% serum, preferably between about 0–1% serum and most preferably between about 0–0.1% serum. Advantageously, serum free "defined" medium can be used, wherein the identity and concentration of each of the components in the medium is known (i.e. an undefined component such as bovine pituitary extract [BPE] is not present in the culture medium).

A "mitogenic agent" or "growth factor" is a molecule which stimulates mitosis of the Schwann cells. Generally, the mitogenic agent or growth factor enhances survival and proliferation of Schwann cells in cell culture and is a polypeptide. The mitogenic polypeptide can be a "native" or "native sequence" polypeptide (i.e. having the amino acid sequence of a naturally occurring growth factor) regardless of the method by which it is produced (e.g. it can be isolated from an endogenous source of the molecule or produced by synthetic techniques including recombinant techniques), or a variant or mutant thereof (see definition below). Preferably, the mitogenic polypeptide has the same amino acid sequence as a growth factor derived from a human, or a fragment thereof. Examples of mitogenic agents include Rse/Axl receptor activators; activators of one or more members of the erbB receptor family; agents which elevate cAMP levels in the culture medium (e.g. forskolin, cholera toxin, cAMP or analogues thereof); adhesion molecules such as neural cell adhesion molecule (N-CAM), laminin or fibronectin; progesterone; neurotrophic factors such as bone-derived neurotrophic factor (BDNF) and ciliary neuronotrophic factor (CNTF); neurotrophin-3, -4, -5, or -6(NT-3, NT-4, NT-5, or NT-6); or a nerve growth factor such as NGF-β; platelet-derived growth factor (PDGF); fibroblast growth factor such as acidic FGF (aFGF) and basic FGF (bFGF); transforming growth factor (TGF) such as TGF-α and TGF-β, including TGF-β1, TGF-β2, TGF-β3, TGF-β4, or TGF-β5; insulin-like growth factors, including IGF-I, IGF-II and des(1-3)-IGF-I (brain IGF-I); insulin-like growth factor binding proteins; and hormones such as estrogen, testosterone, thyroid hormone, and insulin.

A "Rse/Axl receptor activator" comprises a molecule capable of causing the intracellular kinase domain of the Rse and/or Axl receptor to phosphorylate tyrosine residues in a substrate polypeptide. Often, the tyrosine residues are intrinsic to the Rse and/or Axl receptor (i.e. the "substrate" comprises the intracellular domain of the Rse and/or Axl receptor). Therefore, the degree of activation correlates with Rse and/or Axl receptor "autophosphorylation". Rse and/or Axl receptor autophosphorylation can be detected by Western blotting using an anti-phosphotyrosine antibody. See, e.g., Example 2 (vi). However, activation of the Rse and/or Axl receptor may correlate with phosphorylation of a substrate other than the Rse and/or Axl receptor (e.g. a tyrosine kinase existing adjacent the Rse and/or Axl receptor in the cell membrane). This can be detected by measuring tyrosine phosphorylation of the substrate (e.g. by Western blotting). Examples of Rse/Axl receptor activators include gas6, protein S and agonist antibodies which bind to, and activate, the Rse or Axl receptor (see Mark et al, supra).

As used herein, the terms "gas6" and "gas6 polypeptide" refer to a polypeptide which is able to activate the Rse and/or Axl receptor and encompass the mature, pre-, prepro- and pro-forms of gas6 polypeptide, either purified from a natural source, chemically synthesized or recombinantly produced. The present definition specifically includes "human" gas6 polypeptide comprising the amino acid sequence published in Manfioletti et al., *Mol. Cell. Biol.* 13(8):4976–4985 (1993) and other mammalian gas6 polypeptides (such as murine gas6) as well as variants and mutants thereof.

Gas6 has various amino acid domains which are delineated in FIG. 2. The A domain or "Gla region" at the amino terminus of the polypeptide has residues which are rich in γ-carboxyglutamic add (Gla residues) and appear to mediate calcium dependent binding of gas6 to negatively charged phospholipids in cell membranes. The A-domain stretches from about residue 49–89 of human gas6. The following B domain comprises a thrombin sensitive loop and extends from about residue 90–117 of human gas6. The third domain called the C domain herein has four epidermal growth factor (EGF)-like repeats ($C_1$–$C_4$). This C domain extends from about residue 118–278 of human gas6. The remaining D domain is homologous to steroid hormone binding globulin (SHBG) protein and comprises about residues 279–678 of human gas6. The D domain comprises a pair of G domains called G Domain 1 (i.e. about residues 314–471 of human gas6) and G Domain 2 (i.e. about residues 503–671 of human gas6).

The erbB receptor family encompasses those receptors having homology to the epidermal growth factor (EGF) receptor (encoded by the erbB gene) and includes the EGF receptor as well as the HER2, HER3 and HER4 receptors (i.e. erbB2–4, respectively). See U.S. Pat. No. 5,183,884 and EP Pat. Appln No. 599,274. Examples of mitogenic agents which are able to activate one or more members of this family include EGF; heregulin-α (HRG-α), heregulin-β1 (HRG-β1), heregulin-β2, (HRG-β2), heregulin-β2-like (HRG-β2-like), heregulin-Θ3 (HRG-β3) and fragments thereof (see U.S. Pat. No. 5,367,060); acetylcholine receptor inducing activity (ARIA) (Falls et al., *Cell,* 72:801–815 [1993]); glial growth factors (GGFs) (Marchionni et al., *Nature,* 362:312–318 [1993]); and sensory and motor neuron derived factor (SMDF) (see FIG. 3 herein).

The term "antibody" is used in the broadest sense and specifically covers monoclonal antibodies and antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor mounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The monoclonal antibodies herein include hybrid and recombinant antibodies produced by splicing a variable (including hypervariable) domain of an antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. (See, e.g. U.S. Pat. No. 4,816,567 and Mage & Lamoyi, in *Monoclonal Antibody Productions Techniques and Application*, pp.79–97(Marcel Dekker, Inc., New York [1987]),. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature* 256:495 (1975), or may be made by recombinant DNA methods (U.S. Pat. No. 4,816, 567). The "monoclonal antibodies" may also be isolated from phage libraries generated using the techniques described in McCafferty et al., *Nature* 348:552–554 (1990), for example.

"Humanized" forms of non-human (e.g. murine) antibodies are specific chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Polyclonal antibodies directed toward the polypeptide generally are raised in animals by multiple subcutaneous or intraperitoneal injections of the polypeptide and an adjuvant. It may be useful to conjugate the antigen or a peptide fragment thereof to a carrier protein that is immunogenic in the species to be immunized, such as keyhole limpet hemocyanin, serum albumin, bovine thyroglobulin, or soybean trypsin inhibitor, using a bifunctional or derivatizing agent, for example, maleimidobenzoyl sulfosuccinimide ester (conjugation through cysteine residues), N-hydroxysuccinimide (conjugation through lysine residues), glutaraldehyde, succinic anhydride, SOCl$_2$, or R$^1$N=C=NR, where R and R$^1$ are different alkyl groups.

Animals are immunized with such antigen-carrier protein conjugates combining 1 mg or 1 µg of conjugate (for rabbits or mice, respectively) with 3 volumes of Freund's complete adjuvant and injecting the solution intradermally at multiple sites. One month later the animals are boosted with 1/5th to 1/10th the original mount of conjugate in Freund's complete adjuvant by subcutaneous injection at multiple sites. Seven to 14 days later animals are bled and the serum is assayed for anti-gas6 antibody titer. Animals are boosted until the antibody liter plateaus. Preferably, the animal is boosted by injection with a conjugate of the same antigen with a different carrier protein and/or through a different cross-linking agent. Conjugates of the antigen and a suitable carrier protein also can be made in recombinant cell culture as fusion proteins. Also, aggregating agents such as alum are used to enhance the immune response.

Monoclonal antibodies directed toward the antigen are produced using any method which provides for the production of antibody molecules by continuous cell lines in culture. Examples of suitable methods for preparing monoclonal antibodies include the original hybridoma method of Kohler et al., *Nature* 256:495–497 (1975), and the human B-cell hybridoma method, Kozbor, J., *Immunol.* 133:3001 (1984); Brodeur et al., *Monoclonal Antibody Production Techniques and Applications*, pp. 51–63 (Marcel Dekker, Inc., New York, 1987).

Methods for humming non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be performed following methods known in the art (Jones et al., *Nature* 321:522–525 [1986]; Riechmann et al., *Nature* 332:323–327 [1988]; and Verhoeyen et al., *Science* 239:1534–1536 [1988]), by substituting rodent complementary-determining regions (CDRS) for the corresponding regions of a human antibody.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (J$_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, for example, Jakobovits et al., *PNAS* 90:2551–2555 (1993); Jakobovits et al., *Nature* 362:255–258 (1993); and Bruggermann et al., *Year in Immuno.* 7:33 (1993). Human antibodies can also be produced in phage-display libraries. Hoogenboom et al., *J. Mol. Biol.* 227:381 (1991); and Marks et al., *J. Mol. Biol.* 222:581 (1991).

The invention also contemplates the use of "variants" or "mutants" of the polypeptides disclosed. Such variants include fragments of the native polypeptide sequence; polypeptides wherein one or more amino acid residues are added at the N- or C-terminus of, or within, the native polypeptide sequence; one or more amino acid residues are deleted, and optionally substituted by one or more amino acid residues; and derivatives of the above proteins, polypeptides, or fragments thereof, wherein an amino acid residue has been covalently modified so that the resulting product is a non-naturally occurring amino acid. Polypeptide variants may be made synthetically, for example, by site-directed or PCR mutagenesis, or may exist naturally, as in the case of allelic forms and other naturally occurring variants of the translated amino acid sequence that may occur in human and other animal species. Examples of polypeptide variants which can be used include heregulin fragments (e.g. HRG-$\beta 1_{177-244}$; see Holmes et al., Science, 256:1205–1210 [1992]) and gas6 fragments (e.g. a fragment of gas6 which lacks the A domain thereof, such as a D domain fragment or G domain fragment of gas6).

A polypeptide variant is included within the scope of the invention provided that it is functionally active. As used herein, "functionally active" and "functional activity" in reference to the mitogenic factor means that the mitogenic polypeptide is able to enhance survival and/or proliferation of Schwann cells in cell culture.

Often polypeptide variants will share at least about 75% (preferably greater than 80% and more preferably greater than 90%) sequence identity with the translated amino acid sequence encoding the native polypeptide or fragments thereof after aligning the sequences to provide for maximum homology, as determined, for example, by the Fitch et al., PNAS (USA) 80:1382–1386 (1983), version of the algorithm described by Needleman et al., J. Mol. Biol. 48:443–453 (1970). In order to screen for functionally active polypeptide variants, Schwann cells in cell culture can be exposed to the variant and the effect of the variant on Schwann cell survival and/or proliferation relative to one or more controls (e.g. the native polypeptide and a negative control) can be determined. Those variants which enhance Schwann cell survival and preferably promote Schwann cell proliferation in cell culture can be selected for use in the culturing techniques disclosed herein.

Amino acid sequence variants of polypeptides can be prepared by introducing appropriate nucleotide changes into polypeptide DNA and thereafter expressing the resulting modified DNA in a host cell, or by in vitro synthesis. Such variants include, for example, deletions from, or insertions or substitutions of, amino acid residues within the native polypeptide amino acid sequence Any combination of deletion, insertion, and substitution may be made to arrive at an amino acid sequence variant of the native polypeptide, provided that such variant possesses the desired characteristics described herein. Changes that are made in the amino acid sequence to arrive at an amino acid sequence variant of the polypeptide may also result in further modifications of the polypeptide upon its expression in host cells, for example, by virtue of such changes introducing or moving sites of glycosylation.

There are two principal variables in the construction of amino acid sequence variants of the polypeptide: the location of the mutation site and the nature of the mutation. These are variants from the native polypeptide amino acid sequence, and may represent naturally occurring allelic forms of the polypeptide, or predetermined mutant forms of the polypeptide made by mutating polypeptide DNA, either to arrive at an allele or a variant not found in nature.

For example, due to the degeneracy of nucleotide coding sequences, mutations can be made in the nucleotide sequence without affecting the amino acid sequence of the polypeptide encoded thereby. Other mutations can be made that will result in a polypeptide that has an amino acid sequence different from the native sequence, but which is functionally active. Such functionally active amino acid sequence variants are selected, for example, by substituting one or more amino acid residues in the native amino acid sequence with other amino acid residues of a similar or different polarity or charge.

One useful approach is called "alanine scanning mutagenesis". Here, an amino acid residue or group of target residues is/are identified (e.g., charged residues such as arg, asp, his, lys, and glu) and, by means of recombinant DNA technology, replaced by a neutral or negatively charged amino acid (most preferably alanine or polyalanine) to affect the interaction of the amino acids with the surrounding aqueous environment in or outside the cell. Cunningham et al., Science 244:1081–1085 (1989). Those domains demonstrating functional sensitivity to the substitutions are then refined by introducing further or other variants at or for the sites of substitution.

Thus, while the site for introducing an amino acid sequence variation is predetermined, the nature of the mutation per se need not be predetermined. For example, to optimize the performance of a mutation at a given site, ala scanning or random mutagenesis is conducted at the target codon or region and the expressed variants are screened for functional activity as discussed above.

Amino acid sequence deletions generally range from about 1 to 30 residues, more preferably about 1 to 10 residues, and typically are contiguous. Deletions from regions of substantial homology with other mitogenic factors, for example, are more likely to affect the functional activity of the polypeptide. Generally, the number of consecutive deletions will be selected so as to preserve the tertiary structure of the polypeptide in the affected domain, e.g., $\beta$-pleated sheet or $\alpha$ helix.

Amino acid sequence insertions include amino- and/or carboxyl-terminal fusions ranging in length from one amino acid residue to polypeptides containing a hundred or more residues, as well as intrasequence insertions of single or multiple amino acid residues. Intrasequence insertion may range generally from about 1 to 10 residues, more preferably 1 to 5, most preferably 1 to 3. Examples of terminal insertions include variant polypeptide with an N-terminal methionyl residue (such as may result from the direct expression of the polypeptide in recombinant cell culture), and the polypeptide with a heterologous N-terminal signal sequence to improve the secretion of the polypeptide from recombinant host cells. Other insertions include the fusion to the N- or C-terminus of the polypeptide of immunogenic polypeptides (for example, bacterial polypeptides such as lactamase or an enzyme encoded by the E. coli trp locus, or yeast protein), and C-terminal fusions with proteins having a long half-life such as immunoglobulin constant regions, albumin, or ferritin, as described in PCT Pub. No. WO 89/02922 (.published Apr. 6, 1989).

The third group of variants are those in which at least one amino acid residue in the native polypeptide amino acid sequence, and preferably only one, has been removed and a different residue inserted in its place. The sites of greatest interest for making such substitutions are in the regions of the polypeptide amino acid sequence that have the greatest homology with other mitogenic factors. Those sites are likely to be important to the functional activity of the mitogenic factor. Accordingly, to retain functional activity, those sites, especially those falling within a sequence of at least three other identically conserved sites, are substituted in a relatively conservative manner. Such conservative substitutions are shown in Table 1 under the heading of "Preferred Substitution". If such substitutions do not result in a change in functional activity, then more substantial changes, denominated "Exemplary Substitutions" in Table 1, or as further described below in reference to amino acid classes, may be introduced and the resulting variant analyzed for functional activity.

TABLE 1

| Original Residue | Exemplary Substitutions | Preferred Substitution |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | ala; pro | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Insertional, deletional, and substitutional changes in the polypeptide amino acid sequence may be made to improve the stability of the polypeptide. For example, trypsin or other protease cleavage sites are identified by inspection of the encoded amino acid sequence for an arginyl or lysinyl residue. These are rendered inactive to protease by substituting the residue with another residue, preferably a basic residue such as glutamine or a hydrophobic residue such as serine; by deleting the residue; or by inserting a prolyl residue immediately after the residue. Also, any cysteine residues not involved in maintaining the proper conformation of the polypeptide for functional activity may be substituted, generally with serine, to improve the oxidative stability of the molecule and prevent aberrant crosslinking.

DNA encoding amino acid sequence variants is prepared by a variety of methods known in the art. These methods include, but are not limited to, isolation from a natural source (in the case of naturally occurring amino acid sequence variants) or preparation by site-directed (or oligonucleotide-mediated) mutagenesis, PCR mutagenesis, and cassette mutagenesis of an earlier prepared DNA encoding a variant or a non-variant form of the polypeptide.

Site-directed mutagenesis is a preferred method for preparing substitution, deletion, and insertion variants. This technique is well known in the art (see, e.g., Zoller et al., *Meth. Enz.* 100:4668–500 [1983]; Zoller et al., *Meth. Enz.* 154:329–350 [1987]; Carter, *Meth. Enz.* 154:382–403 [1987]; and Horwitz et al., *Meth. Enz.* 185:599–611 [1990]), and has been used, for example, to produce amino acid sequence variants of trypsin and T4 lysozyme, which variants have certain desired functional properties. Perry et al., *Science* 266:555–557 (1984); and Craik et al., *Science* 228:291–297 (1985).

Briefly, in carrying out site-directed mutagenesis, the DNA of interest is altered by first hybridizing an oligonucleotide encoding the desired mutation to a single strand of such DNA. After hybridization, a DNA polymerase is used to synthesize an entire second strand, using the hybridized oligonucleotide as a primer, and using the single strand of DNA as a template. Thus, the oligonucleotide encoding the desired mutation is incorporated in the resulting double-stranded DNA.

PCR mutagenesis is also suitable for making amino acid sequence variants. See Higuchi, in PCR Protocols, pp. 177–183 (Academic Press, 1990); and Vallette et al., *Nuc. Acids Res.* 17:723–733 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., *Gene* 34:315–323 (1985). The starting material is the plasmid (or other vector) comprising the DNA to be mutated. The codon(s) in the DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Covalent modifications of polypeptide molecules also are included within the scope of this invention. For example, covalent modifications are introduced into the polypeptide by reacting targeted amino acid residues of the polypeptide with an organic derivatizing agent that is capable of reacting with selected amino acid side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are different alkyl groups, such as 1-cyclohexyl-3-(2-morpholinyl4-ethyl) carbodiimide or 1-ethyl-3-(4-azonia4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. Alternatively, these residues are deamidated under mildly acidic conditions. Either form of these residues fails within the scope of this invention.

Other modifications include hydroxylation of proline and lysine, phosphorylation of hydroxyl groups of seryl or threonyl residues, methylation of the a-amino groups of lysine, arginine, and histidine side chains, acetylation of the N-terminal amine, and amidation of any C-terminal carboxyl group. Creighton, *Proteins: Structure and Molecular Properties*, pp.79–86 (W. H. Freeman & Co., 1983). The polypeptide can also be covalently linked to nonproteinaceous polymers, e.g. polyethylene glycol, polypropylene glycol or polyoxyalkylenes, in the manner set forth in U.S. Pat. Nos. 4,179,337; 4,301,144; 4,496,689; 4,640,835; 4,670,417; or 4,791,192.

An "iron source" is a molecule or composition which provides Fe ions to the Schwann cells being cultured. Examples include iron carders (e.g. transferrin) and iron salts (e.g. $FeSO_4$).

An "protease inhibitor" reduces or eliminates the proteolytic action of proteases, e.g. Schwann cell-derived proteases, during culturing of the Schwann cells. Examples of protease inhibitors include aprotinin, phenylmethylsulfonyl fluoride (PMSF), leupeptin, pepstatin, 4-(2-aminoethyl)-benzenesulfonyl fluoride hydrochloride-bestatin, chymostatin and benzamidine, the preferred protease inhibitor being aprotinin.

The expression "enhancing survival of a cell" refers to the act of increasing the duration of the viable lifespan of a Schwann cell in cell culture.

The phrase "enhancing proliferation of a cell" encompasses the step of increasing rate and/or extent of cell division in cell culture relative to an untreated cell. An increase in cell proliferation in cell culture can be detected by counting the number of cells before and after culturing in the cell culture medium disclosed herein. The extent of proliferation can be quantified via microscopic examination of the percentage and number of mitotic figures in the culture and the degree of confluency. Cell proliferation can also be quantified by measuring $^3H$ uptake and incorporation into DNA by the cells.

The isolated Schwann cell populations are desirably "substantially homogenous" which means that between about 90 to 100%, and preferably 99% to 100% of the cells in the population are Schwann cells.

By "demyelination" is meant the loosening, breakdown and eventual disintegration of the structure of the myelin membrane surrounding an axon. This expression encompasses partial and complete demyelination of the Schwann cells.

"Pharmaceutically acceptable" carders or vehicles are ones which are nontoxic to the mammal being exposed thereto at the dosages and concentrations employed. Often the pharmaceutically acceptable carrier is an aqueous pH buffered solution. Examples of pharmaceutically acceptable carders include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or polyethylene glycol (PEG). The preferred pharmaceutically acceptable carrier or vehicle is a semi-solid, gelatinous or viscous support medium. Examples of such gelatinous carriers or vehicles include collagen, collagen-glycosaminoglycan, fibrin, polyvinyl chloride, polyamino acids such as polylysine or polyornithine, hydrogels, agarose, dextran sulfate and silicone.

A "nervous system injury" is a disease or disorder which results in disconnection of axons, degeneration of neurons, or demyelination. Examples of nervous system injuries include traumatic lesions (e.g. caused by physical injury or surgery, and compression injuries); ischemic lesions (e.g. cerebral or spinal cord infarction and ischemia); malignant lesions; infectious lesions (e.g. resulting from an abscess or associated with infection by human immunodeficiency virus, Lyme disease, tuberculosis, syphillis, or herpes infection); degenerative lesions (e.g. associated with Parkinson's disease, Alzheimer's disease, Huntington's chorea or amyotrophic lateral sclerosis); lesions associated with nutritional diseases or disorders (e.g. Vitamin B 12 deficiency, folic acid deficiency, Wernicke disease, tobacco-alcohol amblyopia, Marchiafava-Bignami disease and alcoholic cerebellar degeneration); neurological lesions associated with systemic diseases (e.g. associated with diabetes, systemic lupus erythematosos, carcinoma or sarcoidosis); lesions caused by toxic substances (e.g. alcohol, lead or neurotoxin); and demyelinated lesions (e.g. associated with multiple sclerosis, human immunodeficiency ms-associated myelopathy, transverse myelopathy of various etiologies, progressive multifocal leukoencepholopathy and central pontine myelinolysis).

The terms "treating", "treatment", and "therapy" refer to curative therapy, prophylactic therapy, and preventative therapy.

The term "mammal" refers to any mammal classified as a mammal, including humans, cows, horses, dogs, sheep and cats. In a preferred embodiment of the invention, the mammal is a human.

II. Modes for Practicing the Invention

1. Starting Materials and Pre-incubation

Nerve tissue which comprises Schwann cells (e.g. peripheral nerve tissue) is derived from a mammal, preferably a human (upon receipt of the patient's consent). The tissue may be embryonic tissue (e.g. dorsal root ganglia), but in the preferred embodiment is derived from an adult patient, since this facilitates autologous transplants and thus reduces the likelihood of adverse immunogenic reactions in the patient.

The invention provides for heterologous transplantation of Schwann cells (e.g. from one mammalian species to another mammalian species or from an embryo to an adult patient) as well as autotransplantation. If a patient for autotransplant has damaged tissue, the damaged tissue can provide a source for the Schwann cells. Alternatively, a surgical procedure such as nerve biopsy can be performed in order to harvest tissue comprising the Schwann cells to be isolated and cultured. Potential sources of peripheral nerve include the sural nerve of the ankle, the saphenous nerve, or the brachial or antebrachial nerve of the upper limb. The nerves are preferably sensory nerves.

A suitable size for the starting nerve tissue is between about 10 mg to 10 gm, preferably between about 100 mg to 1 gm. The nerve tissue can be stored in medium (e.g. RPMI-1640 [Sigma], Liebovitz's L15 or Belzer's UW solution), prior to a pre-incubation step which normally precedes the primary culturing phase of the instant invention. Pre-incubation is advantageous since it facilitates demyelination of the Schwann cells. For the pre-incubation step, the nerve tissue is desirably treated with one or more protease enzymes for a sufficient period of time to loosen connective tissue and thereby promote demyelination. Many protease enzymes are commercially available which can be used for this step and include collagenase, dispase and other serine proteases, for example. In the preferred embodiment, the nerve tissue is exposed to a 1% collagenase/dispase solution. The time required to loosen the connective tissue can vary depending on the protease enzymes chosen, but will normally be a period of about 10 minutes to 100 minutes and preferably about 20 minutes to 50 minutes. The enzymatic treatment can be carded out at about 37° C., for example. Excess enzyme can be removed by gentle washing with culture medium.

Following enzymatic treatment, the nerve tissue is cultured under appropriate conditions and for a sufficient period of time to facilitate demyelination of the Schwann cells (which may have already started to occur). Accordingly, the nerve tissue may be placed in dishes (e.g. 100 mm petri dishes) in culture medium supplemented with mitogenic agents and other components as desired. For example, the culture medium can be serum free medium which is supplemented with one or more mitogenic agents. Normally, at least an erbB activator (e.g. heregulin), insulin (or an IGF) and at least one protease inhibitor (e.g. aprotinin) in the ranges exemplified below will be present in the culture medium for the pre-incubation period. Often, the culture medium for the primary culturing can be used. This step is distinguished from the primary culturing phase, in that the cells are not adhered to the culture plate by an adhesion protein, but are suspended in the cell culture medium (however, some cells may naturally adhere to the surface of the dishes in which pre-incubation is performed). The Schwann cells are cultured for a sufficient period of time for demyelination to occur, with exemplary culturing times being in the range of about 12 hours to 120 hours and preferably about 18 hours to 48 hours.

Optionally, the cells can then be pooled by centrifugation and resuspended in culture medium by pipetting.

2. Obtaining Schwann Cell Primary Cultures

While the foregoing pre-incubation step will normally precede the culturing step, in alternative embodiments, the Schwann cells can be subjected directly to the following culturing procedure. Also, this culturing procedure can be preceded, or followed by, other culturing steps as desired.

A solid phase (e.g. a plastic tissue culture dish or plate) is normally coated with extracellular matrix/adhesion proteins such as laminin, fibronectin, poly-lysine or collagen, with laminin being preferred. This allows preferential adhesion and migration of the Schwann cells onto the coated solid phase. The Schwann cells are cultured in the laminin-coated culture plates in a suitable culture medium. Suitable culture media are well known to persons skilled in the art and include, but are not limited to, commercially available media such as F12/DME, Ham's F10 (Sigma), Minimal Essential Medium ([MEM], Sigma), RPMI-1640 (Sigma), and Dulbecco's Modified Eagle's Medium ([DMEM], Sigma). In addition, any of the media described in Ham and Wallace, Meth. Enz., 58:44 (1979), Barnes and Sato, Anal Biochem., 102:255 (1980), U.S. Pat. Nos. 4,767,704; 4,657,866; 4,927, 762; or 4,560,655; WO 90/03430; WO 87/00195; 30,985; or 5,122,469, the disclosures of all of which are incorporated herein by reference, may be used as culture media. Any of these media may be supplemented as necessary with mitogenic agents, ions (such as sodium, chloride, calcium, magnesium, and phosphate), buffers (such as HEPES), nucleosides (such as adenosine and thymidine), trace elements (defined as inorganic compounds usually present at final concentrations in the micromolar range), and glucose or an equivalent energy source. Any other necessary supplements may also be included at appropriate concentrations that would be known to those skilled in the art. The preferred culture medium is F12/DME (1:1).

The culture medium generally includes a first mitogenic agent which is a P, se/Axl receptor activator, with gas6 being the preferred activator. Example 26) describes a technique for the production of recombinant human gas6. The concentration of gas6 in the medium will preferably be in the range of about 0.1 ng/ml to 100 ng/ml, more preferably 1 ng/ml to 30 ng/ml, and most preferably 10 ng/ml to 30 ng/ml. A second mitogenic agent is added to the culture medium and this is suitably a molecule which activates a member of the erbB receptor family. Heregulin is the preferred activator and the human heregulin-$\beta1_{177-224}$ fragment is the most preferred second mitogenic agent (see Holmes et al., Science. 256:1205–1210 [1992]). The concentration of heregulin in the medium will preferably be in the range of about 0. 1 nM to 50 nM, more preferably 0.5 μnM to 20 nM, and most preferably 4 nM to 10 nM. Normally, further mitogenic agents will also be present. An agent which elevates cAMP levels in the medium is desirably present. Forskolin is the preferred such agent and suitable concentrations of this molecule are in the range from 0.1 μM to 50 μM forskolin, more preferably 1 μM to 20 μM forskolin, and most preferably 2 μM to 10 μM forskolin. Insulin or an IGF (e.g. IGF-I or IGF-II) can be added to the medium. Preferably, insulin will be added to the medium in the range 0.1 μg/ml to 200 μg/ml, more preferably 0.5 μg/ml to 20 μg/ml, and most preferably 5 μg/ml to 20 μg/ml. Progesterone may also be added to the culture medium in the range 0.1 M to 1000 nM, more preferably 3 mM to 200 nM, and most preferably 3 nM to 50 nM, as desired. In addition to the one or more mitogenic agents, advantageously, an iron source such as transferrin will be present in the culture medium. The concentration of transferrin in the medium will preferably be in the range 0.1 μg/ml to 100 μg/ml, more preferably 1 μg/rot to 25 μg/ml, and most preferably 5 μg/ml to 10 μg/ml. There are many other optional supplements and these include Vitamin E (an anti-oxidant and anti-transforming agent), preferably in the range 0.1 μg/ml to 100 μg/ml, more preferably 1 μg/ml to 20 μg/ml, and most preferably 5 μg/ml to 10 μg/ml; protease inhibitors such as aprotinin, preferably in the range 1 μg/ml to 500 μg/ml, more preferably 10 μg/ml to 100 μg/ml, and most preferably 20 μg/ml to 50 μg/ml; and chemically defined lipids (Sigma Cat #11905–015), preferably in the range from about 1 μL/ml to 500 μL/ml, more preferably 10 μL/ml to 100 μL/ml, and most preferably 25 μL/ml to 50 μL/ml. Any other necessary supplements may also be included at appropriate concentrations that would be known to those skilled in the art.

The culture medium can be changed at various intervals (e.g. about every 1 to 5 days) and the cells cultured at a physiologically acceptable temperature between about 33° to 38° C., preferably about 37° C.

The invention also provides serum free culture medium comprising a suitable combination of two or more of the above components (preferably in the concentration ranges specified above) for culturing Schwann cells, and especially human Schwann cells. The serum free culture medium can be provided in the form of an article of manufacture or kit. The article of manufacture comprises a container with a label. Suitable containers include, for example, bottles, vials, and test tubes. The containers may be formed from a variety of materials such as glass or plastic. The container holds the culture medium described above, preferably at room temperature, which medium is effective for enhancing survival and/or proliferation of Schwann cells. The label on the container indicates that the culture medium is used for enhancing survival and/or proliferation of Schwann cells, and may also indicate directions for in vitro use, such as those described above, and instructions for optimal storage conditions.

3. Polypeptide Production

In the event that a polypeptide is not available commercially, the following section provides methodologies for the production of polypeptides, such as mitogenic polypeptides and variants thereof for use in the culturing techniques disclosed herein.

Techniques suitable for the production of native polypeptide or polypeptide variants are well known in the art and include isolating polypeptide from an endogenous source of the polypeptide (e.g. from serum), peptide synthesis (using a peptide synthesizer) and recombinant techniques (or any combination of these techniques). The preferred technique for production of native polypeptide or a polypeptide variant is a recombinant technique.

Nucleic acid encoding native polypeptide can be isolated from a cDNA library prepared from tissue believed to possess the polypeptide mRNA and to express it at a detectable level (e.g. brain tissue). Libraries are screened with probes (such as antibodies or oligonucleotides of about 20–80 bases) designed to identify the gene of interest or the protein encoded by it. Screening the cDNA or genomic library with the selected probe may be conducted using standard procedures as described in chapters 10–12 of Sambrook et al., *Molecular Cloning: A Laboratory Manual* (New York: Cold Spring Harbor Laboratory Press, 1989).

Techniques for generating polypeptide mutants via modification of the wildtype nucleic acid have been discussed above. The nucleic acid (e.g., cDNA or genomic DNA) encoding the native polypeptide or polypeptide variant is inserted into a replicable vector for further cloning (amplification of the DNA) or for expression. Many vectors are available. The vector components generally include, but are not limited to, one or more of the following: a signal sequence, an origin of replication, one or more marker genes, an enhancer element, a promoter, and a transcription termination sequence.

The polypeptide may be produced as a fusion polypeptide with a signal sequence or other polypeptide having a specific cleavage site at the N-terminus of the polypeptide. In general, the signal sequence may be a component of the vector, or it may be a part of the DNA that is inserted into the vector. The heterologous signal sequence selected preferably is one that is recognized and processed (i.e., cleaved by a signal peptidase) by the host cell. For prokaryotic host cells, the signal sequence may be substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, alpha factor leader (including Saccharomyces and Kluyveromyces α-factor leaders, the latter described in U.S. Pat. No. 5,010,182 issued 23 Apr. 1991), or acid phosphatase leader, the C. albicans glucoamylase leader (EP 362,179 published 4 Apr. 1990), or the signal described in WO 90/13646 published 15 Nov. 1990. In mammalian cell expression the native polypeptide signal sequence is satisfactory, although other mammalian signal sequences may be suitable as well as viral secretory leaders, for example, the herpes simplex gD signal. The DNA for such precursor region is ligated in reading flame to DNA encoding the native polypeptide/polypeptide variant.

Both expression and cloning vectors contain a nucleic acid sequence that enables the vector to replicate in one or more selected host cells. Generally, in cloning vectors this sequence is one that enables the vector to replicate independently of the host chromosomal DNA and includes origins of replication or autonomously replicating sequences. Such sequences are well known for a variety of bacteria, yeast, and viruses. The origin of replication from the plasmid pBR322 is suitable for most Gram-negative bacteria, the 2 μg plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors should contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin (Southern et al., *J. Molec. Appl. Genet.* 1:327 [1982]), mycophenolic acid (Mulligan et al., *Science* 209:1422 [1980]) or hygromycin (Sugden et al., *Mol. Cell Biol.* 5:410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the polypeptide nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the polypeptide. Increased quantities of the polypeptide are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA* 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the polypeptide. This amplification technique can be used with any otherwise suitable host, e.g., ATCC No. CCL61 CHO-K1, notwithstanding the presence of endogenous DHFR if; for example, a mutant DHFR gene that is highly resistant to Mtx is employed (EP 117,060).

Alternatively, host cells (particularly wild-type hosts that contain endogenous DHFR) transformed or co-transformed with DNA sequences encoding polypeptide, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature* 282:39 [1979]; Kingsman et al., *Gene* 7:141 [1979]; or Tschemper et al., *Gene* 10:157 [1980]). The trp1 gene provides a selection marker for a mutant strain of yeast lacking the ability to grow in tryptophan, for example, ATCC No. 44076 or PEP4-1 (Jones, *Genetics* 85:12 [1977]). The presence of the trp1 lesion in the yeast host cell genome then provides an effective environment for detecting transformation by growth in the absence of tryptophan. Similarly, Leu2deficient yeast strains (ATCC 20,622 or 38,626) are complemented by known plasmids bearing the Leu2 gene.

In addition, vectors derived from the 1.6 m circular plasmid pKD1 can be used for transformation of Kluyveromyces yeasts. Bianchi et al, *Curr. Genet.* 12:185 (1987). More recently, an expression system for large-scale production of recombinant calf chymosin was reported for K. lactis. Van den Berg, *Bio/Technology* 8:135 (1990). Stable multi-copy expression vectors for secretion of mature recombinant human serum albumin by industrial strains of Kluyveromyces have also been disclosed. Fleer et al., *Bio/Technology* 9:968–975 (1991).

Expression and cloning vectors usually contain a promoter that is recognized by the host organism and is operably linked to the polypeptide nucleic acid. A large number of promoters recognized by a variety of potential host cells are well known. These promoters are operably linked to polypeptide-encoding DNA by removing the promoter from the source DNA by restriction enzyme digestion and inserting the isolated promoter sequence into the vector.

Promoters suitable for use with prokaryotic hosts include the β-lactamase and lactose promoter systems (Chang et al., *Nature* 275:615 [1978]; and Goeddel et al, *Nature* 281:544 [1979]), alkaline phosphatase, a tryptophan (trp) promoter system (Goeddel, *Nucleic Acids Res.*, 8:4057 [1980] and EP 36,776) and hybrid promoters such as the tac promoter (deBoer et al., *Proc. Natl. Acad. Sci, USA* 80:21–25 [1983]). However, other known bacterial promoters are suitable. Their nucleotide sequences have been published, thereby enabling a skilled worker operably to ligate them to DNA encoding the polypeptide (Siebenlist et al., *Cell* 20:269 [1980]) using linkers or adaptors to supply any required restriction sites. Promoters for use in bacterial systems also will contain a Shine-Dalgarno (S. D.) sequence operably linked to the DNA encoding the polypeptide.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.* 255:2073 [1980]) or other glycolytic enzymes (Hess et al., *J. Adv. Enzyme Reg.* 7:149 [1968]; and Holland, *Biochemistry* 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Polypeptide transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter or from heat-shock promoters.

The early and late promoters of the SV40 virus are conveniently obtained as an SV40 restriction fragment that also contains the SV40 viral origin of replication. Fiers et al., *Nature* 273:113 (1978); Mulligan and Berg, *Science* 209:1422–1427 (1980); Pavlakis et al., *Proc. Natl. Acad. Sci. USA* 78:7398–7402 (1981). The mediate early promoter of the human cytomegalovirus is conveniently obtained as a HindIII E restriction fragment. Greenaway et al., *Gene* 18:355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature* 295:503–508 (1982) on expressing cDNA encoding immune interferon in monkey cells; Reyes et al., *Nature* 297:598–601 (1982) on expression of human β-interferon cDNA in mouse cells under the control of a thymidine kinase promoter from herpes simplex virus; Canaani and Berg, *Proc. Natl. Acad. Sci, USA* 79:5166–5170 (1982) on expression of the human interferon β1 gene in cultured mouse and rabbit cells; and Gorman et al., *Proc. Natl. Acad. Sci. USA* 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

Transcription of DNA encoding the polypeptide by higher eukaryotes is often increased by inserting an enhancer sequence into the vector. Enhancers are relatively orientation and position independent, having been found 5'(Laimins et al., *Proc. Natl. Acad. Sci. USA* 78:993 [1981]) and 3' (Lusky et al., *Mol. Cell Bio.* 3:1108 [1983]) to the transcription unit, within an intron (Banerji et al., *Cell* 33:729 [1983]), as well as within the coding sequence itself (Osborne et al., *Mol. Cell Bio.* 4:1293 [1984]). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature* 297:17–18 (1982) on enhancing elements for activation of eukaryotic promoters. The enhancer may be spliced into the vector at a position 5' or 3' to the polypeptide-encoding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide.

Construction of suitable vectors containing one or more of the above listed components employs standard ligation techniques. Isolated plasmids or DNA fragments are cleaved, tailored, and relegated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.* 9:309 (1981) or by the method of Maxam et al., *Methods in Enzymology* 65:499 (1980).

Particularly useful in the practice of this invention are expression vectors that provide for the transient expression in mammalian cells of DNA encoding the polypeptide. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17–16.22. Transient expression systems, comprising a suitable expression vector and a host cell, allow for the convenient positive identification of polypeptides encoded by cloned DNAs, as well as for the rapid screening of polypeptide variants having desired binding specificities/affinities.

Other methods, vectors, and host cells suitable for adaptation to the synthesis of the polypeptide in recombinant vertebrate cell culture are described in Gething et al., *Nature* 293:620–625 (1981); Mantei et al., *Nature* 281:40–46 (1979); Levinson et al.; EP 117,060; and EP 117,058. A particularly useful plasmid for mammalian cell culture expression of the polypeptide is pRK5 (EP 307,247) or pSVI6B (PCT pub. no. WO 91/08291 published 13 Jun. 1991).

The choice of host cell line for the expression of polypeptide depends mainly on the expression vector. Suitable host cells for cloning or expressing the vectors herein are prokaryote, yeast, or other higher eukaryote cells described above. Suitable prokaryotes for this purpose include eubacteria, such as Gram-negative or Gram-positive organisms, for example, Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. subtilis* and *B. licheniformis* (e.g., *B. licheniformis* 41P disclosed in DD 266, 710 published 12 Apr. 1989), Pseudomonas such as *P. aeruginosa*, and Streptomyces. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Strain W3110 is a particularly preferred host or parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 27C7. The complete genotype of 27C7 is tonAΔ ptr3 phoAΔE15 Δ(argF-lac) 169 ompTΔdegP41kan'. Strain 27C7 was deposited on 30 Oct. 1991 in the American Type Culture Collection as ATCC No. 55,244. Alternatively, the strain or*E. coli* having mutant periplasmic protease disclosed in U.S. Pat. No. 4,946,783 issued 7 Aug. 1990 may be employed. Alternatively, methods of doping, e.g., PCR or other nucleic acid polymerase reactions, are suitable.

In addition to prokaryotes, eukaryotic microbes such as filamentous fungi or yeast are suitable cloning or expression hosts for polypeptide-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* (Beach and Nurse, *Nature* 290:140 [1981]; EP 139,383 published May 2, 1985); Kluyveromyces hosts (U.S. Pat. No. 4,943,529; Fleer et al., supra) such as, e.g., *K. lactis* (MW98-8C, CBS683, CBS4574; Louvencourt et al., *J. Bacteriol.*, 737 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., supra), *K. thermotolerans*, and *K. marxianus*; *yarrowia* (EP 402,226); *Pichia pastoris* (lip 183,070; Sreekrishna et al., *J. Basic Microbiol.* 28:265–278 [1988]); Candida; *Trichoderma reesia* (lip 244,234); *Neurospora crassa* (Case et al., *Proc.*

*Natl. Acad. Sci. USA* 76:5259–5263 [1979]); Schwanniomyces such as *Schwanniomyces occidentalis* (EP 394,538 published 31 Oct. 1990); and filamentous fungi such as, e.g., Neurospora, Penicillium, Tolypocladium (WO 91/00357 published 10 Jan. 1991), and Aspergillus hosts such as *A. nidulans* (Ballance et al., *Biochem. Biophys. Res. Commun.* 112:284–289 [1983]; Tilburn et at, *Gene* 26:205–221 [1983]; Yelton et al, *Proc. Natl. Acad. Sci. USA* 81:1470–1474 [1984]) and *A. niger* (Kelly and Hynes, *EMBO J.* 4:475–479 [1985]).

Suitable host cells for the expression of glycosylated polypeptides are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology* 6:47–55 (1988); Miller et al., in *Genetic Engineering*, Setlow et al., eds., Vol. 8 (Plenum Publishing, 1986), pp. 277–279; and Maeda et al., *Nature* 315:592–594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the polypeptide DNA. During incubation of the plant cell culture with *A. tumefaciens*, the DNA encoding the polypeptide is transferred to the plant cell host such that it is transfected, and will, under appropriate conditions, express the polypeptide DNA. In addition, regulatory and signal sequences compatible with plant cells are available, such as the nopaline synthase promoter and polyadenylation signal sequences. Depicker et al., *J. Mol. Appl. Gen.* 1:561 (1982). In addition, DNA segments isolated from the upstream region of the T-DNA 780 gene are capable of activating or increasing transcription levels of plant-expressible genes in recombinant DNA-containing plant tissue. EP 321,196 published 21 Jun. 1989.

Propagation of vertebrate cells in culture (tissue culture) has become a routine procedure in recent years (*Tissue Culture*, Academic Press, Kruse and Patterson, editors [1973]). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 [1977]); baby hamster kidney cells (BHK, ATCC CCL 10); Chinese hamster ovary cells/-DHFR (CHO, Urlaub and Chasin, *Proc. Natl. Acad. Sci. USA* 77:4216 [1980]); mouse sertoli cells (TM4, Mather, *Biol. Reprod.* 23:243–251 [1980]); monkey kidney cells (CV1 ATCC CCL 70); African green monkey kidney cells (VERO-76, ATCC CRL-1587); human cervical carcinoma cells (HELA ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44–68 [1982]); MRC 5 cells; FS4 cells; and a human hepatoma line (Hep G2).

Host cells are transfected with the above-described expression or cloning vectors of this invention and cultured in conventional nutrient media modified as appropriate for inducing promoters, selecting transformants, or amplifying the genes encoding the desired sequences. Depending on the host cell used, transfection is done using standard techniques appropriate to such cells. The calcium treatment employing calcium chloride, as described in section 1.82 of Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene* 23:315 (1983) and WO 89/05859 published 29 Jun. 1989. In addition, plants may be transfected using ultrasound treatment as described in WO 91/00358 published 10 Jan. 1991.

For mammalian cells without such cell walls, the calcium phosphate precipitation method of Graham and van der Eb, *Virology* 52:456–457 (1978) is preferred. General aspects of mammalian cell host system transformations have been described by Axel in U.S. Pat. No. 4,399,216 issued 16 August 1983. Transformations into yeast are typically carried out according to the method of Van Solingen et al., *J. Bact.* 130:946 (1977) and Hsiao et al., *Proc. Natl. Acad. Sci. (USA)* 76:3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology* (1989), Keown et al, *Methods in Enzymology* 185:527–537 (1990), and Mansour et al., *Nature* 336:348–352 (1988).

Prokaryotic cells used to produce the polypeptide are cultured in suitable media as described generally in Sambrook et al., supra.

The mammalian host cells used to produce the polypeptide of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.* 58:44 (1979), Barnes and Sato, *Anal. Biochem.* 102:255 (1980), U.S. Pat. Nos. 4,767,704; 4,657,866; 4,927, 762; or 4,560,655; WO 90/03430; WO 87/00195; U.S. Pat. No. 30,985; or U.S. Pat. No. 5,122,469, the disclosures of all of which are incorporated herein by reference, may be used as culture media for the host cells. Any of these media may be supplemented as necessary with mitogenic agents (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art.

For production of gas6, it may be desirable to culture host cells transformed with gas6 nucleic acid in the absence of Vitamin K as this can reduce y carboxylation of the A domain of gas6. Alternatively, the transformed host cells can be cultured in the presence of a carboxylase inhibitor, such as warfarin, as desired.

The culture conditions, such as temperature, pH, and the like, are those previously used with the host cell selected for expression, and will be apparent to the ordinarily skilled artisan. In general, principles, protocols, and practical techniques for maximizing the productivity of mammalian cell cultures can be found in *Mammalian Cell Biotechnology a Practical Approach*, M. Butler, ed., IL Press, 1991. The host cells referred to in this disclosure encompass cells in culture as well as cells that are within a host animal.

The polypeptide preferably is recovered from the culture medium as a secreted polypeptide, although it also may be recovered from host cell lysates.

To purify the polypeptide from other cell polypeptides, the particulate debris, either host cells or lysed fragments, is removed, for example, by centrifugation or ultrafiltration. Optionally, the protein may be concentrated with a commercially available protein concentration filter, followed by separating the polypeptide from other impurities by one or more steps selected from heparin Sepharose chromatography, immunoaffinity chromatography, ion-exchange column fractionation (e.g., on DEAE or matrices containing carboxymethyl or sulfopropyl groups), chromatography on BLUE-SEPHAROSE™, CM BLUE-SEPHAROSE™, MONO-Q™, MONO-S™, LENTIL LECTIN-SEPHAROSE™, WGA-SEPHAROSE™, CON-A-SEPHAROSE™, Ether TOYOPEARL™, Butyl TOYOPEARL™, Phenyl TOYOPEARL™, or protein A SEPHAROSE™, SDS-PAGE chromatography, silica chromatography, chromatofocusing, reverse phase HPLC (e.g., silica gel with appended aliphatic groups), gel filtration using, e.g., SEPHADEX™ molecular sieve or size-exclusion chromatography, chromatography on columns that selectively bind the polypeptide, and ethanol or ammonium sulfate precipitation. A protease inhibitor may be included in any of the foregoing steps to inhibit proteolysis and antibiotics may be included to prevent the growth of adventitious contaminants. Examples of suitable protease inhibitors include phenylmethylsulfonyl fluoride (PMSF), leupeptin, pepstatin, aprotinin, 4-(2-aminoethyl)-benzenesulfonyl fluoride hydrochloride-bestatin, chymostatin, and benzamidine.

Polypeptide variants in which residues have been deleted, inserted, or substituted are recovered in the same fashion as native polypeptide, taking account of any substantial changes in properties occasioned by the variation. For example, preparation of epitope tagged polypeptide facilitates purification using an immunoaffinity column containing antibody to the epitope tag to adsorb the fusion polypeptide. Immunoaffinity columns such as a rabbit polyclonal anti-polypeptide column can be employed to absorb the polypeptide variant by binding it to at least one remaining immune epitope. One skilled in the art will appreciate that purification methods suitable for native polypeptide may require modification to account for changes in the character of polypeptide or its variants upon production in recombinant cell culture.

4. Pharmaceutical formulations and prostheses

Pharmaceutical formulations comprising isolated Schwann cells and a pharmaceutically acceptable carrier or vehicle as described above can be prepared using techniques which are well known in the art. Optionally, the pharmaceutical formulation may include one or more mitogenic agents (e.g. heregulin and gas6) and other components (e.g. extracellular matrix proteins such as laminin). If a gelatinous support is used as the pharmaceutically acceptable vehicle, the Schwann cells may be introduced into a liquid phase of the vehicle which can be treated such that it becomes more solid (e.g. a unpolymerized vehicle may be induced to polymerize). For example, the Schwann cells may be added to collagen solubilized in acetic acid in $H_2O$. When this mixture is brought to neutral pH, by addition of a suitable base such as NaOH and to isotonicity by the addition of salts, a gel should form.

The Schwann cells can also be delivered in prostheses or devices such as those which have been described in the literature. Generally, a solid tube filled with the Schwann cells (preferably formulated in a gelatinous vehicle) is used as the prosthesis to bridge a gap in a peripheral nerve, optical nerve or other parts of the nervous system. For example, Paino and Bunge, *Experim. Neurol.* 114:254–257 (1991) describe polymerized collagen rolls enclosing Schwann cells which can be used as nerve repair prostheses. Guénard et al., *J. Neuroscience* 12(9): 3310–3320 (1992) refer to semipermeable guidance channels in which Schwann cells are seeded. U.S. Pat. No. 5,030,225 is concerned with a medical device or prosthesis for regenerating a severed nerve which includes an electrically-charged membrane having openings adapted to receive the ends of the severed nerve and a lumen for permitting regeneration of the nerve therethrough. The lumen can be filled with the Schwann cells prior to placing the device in a patient. U.S. Pat. No. 4,662,884 describes another type of prothesis for promoting nerve regeneration which can also be filled with Schwann cells which have been isolated using the techniques described herein.

5. Non-therapeutic Uses for the Schwann Cells

Schwann cells produce a number of neurotrophic and neurite-promoting factors including NGF, IGF-I, CNTF and BDNF (see Collier et al., *Exper. Neurol.* 124:129–133 [1993]). Accordingly, Schwann cells isolated and cultured using the techniques described herein can be used to produce these factors. It is desirable to have populations of Schwann cells in cell culture for isolation of Schwann cell-specific factors e.g. P75$^{NGFR}$, S-100 protein, laminin and GFAP. Such factors are useful as diagnostic tools themselves or can be used an antigens to generate antibodies for diagnostic use.

In other embodiments, the Schwann cells can be transformed with nucleic acid encoding a polypeptide of interest, and used for the production of the polypeptide by recombinant techniques such as those described herein above.

The Schwann cell primary cultures may also be used to support the growth and/or differentiation of other cells in cell culture. In this manner, Schwann cells may promote neuronal survival or the growth and survival of embryonic neuronal percursors in cell culture.

It is also desirable to have stable populations of Schwann cells in cell culture to facilitate characterization of other mitogens and growth inhibitory agents for these cells.

6. Therapeutic uses for the Schwann cells

It is beneficial to have populations of mammalian Schwann cells (preferably human Schwann cells) for transplantation into areas of damaged spinal cord in an effort to influence regeneration of interrupted central axons, for assisting in the repair of peripheral nerve injuries and as alternatives to multiple autografts. See Levi et al., *J. Neuroscience* 14(3): 1309 (1994). The use of cell culture techniques to obtain an abundant source of autologous graft material from a small biopsy has already met with clinical success in providing human epidermal cells to cover extensive burns (Gallico et al., *N. Eng J. Med.*, 311: 338–51 [1984]). Furthermore, it has been shown that Schwann cells from human xenografts are capable of myelinating regenerating peripheral axons from mice which have been immunosuppressed (Aguayo et al., *Nature*, 268:753–755 [1977], and Aguayo et al., Soc. *Neurosci. Symp.* 4:361–383 [1979]). Accordingly, it is expected that the above approach will meet with success in humans.

Schwann cells isolated and cultured using the techniques described herein can be utilized in the treatment of a nervous system injury, such as those described above. Isolated Schwann cells, pharmaceutical compositions comprising Schwann cells, or prostheses filled with the Schwann cells can be introduced into a nervous system lesion using any method known in the art. Methods of introducing the Schwann cells into the mammal include surgical techniques which expose the neurological lesion and permit introduction of the cells, and direct injection of the cells into the lesion without exposing the lesion. For example, if the spinal cord has been destroyed, laminectomy may be used to expose the affected region of the spinal cord. After contusion lesions, the damaged central region of the cord is often removed by macrophage action, leaving a fluid-filled cyst. Using ultrasound to visualize the cyst, an injection of the Schwann cells (optionally in a pharmaceutically acceptable carrier) may be made directly into the cystic defect. Where a lesion occurs in a structurally clearly defined nerve (e.g. a facial or optic nerve), a delivery device as described above may be molded to conform in size and shape to a segment of the affected nerve, thereby forming a nerve prosthesis. The affected nerve may be surgically exposed and the lesion removed and replaced with the nerve prosthesis, which may be sutured or otherwise fixed in place. In another embodiment, if a lesion occurs within an infarcted area or area of demyelination deep within the spinal cord or cerebral hemisphere, the Schwann cells (preferably in a liquid pharmaceutical carrier) may be injected into the affected area (e.g. into the brain in the case of Parkinson's disease) using radiologic guidance, being careful to limit the injected material to a volume easily accommodated by the tissue so as to avoid increased pressure within the tissue and/or intracranially. See, for example, Spencer et al., Unilateral transplantation of human fetal mesencephalic tissue into the caudate nucleus of patients with Parkinson's disease, *New Eng. J. Med.* 327:1541–1548 (1992). Other techniques for delivering the Schwann cells to an affected area are available. See, for example, WO 92/03536 concerning delivery of Schwann cells in the repair of a cauda equina lesion.

An "effective amount" of the Schwann cells to be administered to the patient will depend, for example, upon the therapeutic objectives, the route of administration, and the condition of the patient. Accordingly, it will be necessary for the therapist to titer the dosage and modify the route of administration as required to obtain the optimal therapeutic effect. A typical dosage might range from about $1\times10^4$ to $1\times10^6$ Schwann cells, for example. A single dose or multiples doses of Schwann cells may be administered to the patient. Where possible, it is desirable to determine appropriate dosage ranges first in vitro, for example, using animal models such as those described above, from which dosage ranges for human patients may be extrapolated.

The following examples are offered by way of illustration and not by way of limitation. The disclosures of all citations in the specification are expressly incorporated herein by reference.

EXAMPLE 1

Isolating and Culturing Rat Schwann Cells

This example discloses a defined, serum-free culture system which yields homogenous Schwann cell cultures but does not support the growth of fibroblasts. The serum free culture system allows for the continuous growth and subculture of the Schwann cell component at a rapid rate from the first days of primary culture. Since the fibroblasts do not proliferate, they rapidly disappear from the cultures leading to pure Schwann cell cultures by the second passage. Using this approach, it is possible to continuously grow and establish normal Schwann cell lines from the dorsal root ganglia (DRG) of both embryonic and adult rats. These cells do not undergo a "crisis" period during which there is significant cell loss and the expansion of a transformed cell phenotype. They do, however, undergo distinct growth phases characterized by differences in their response to, and production of, growth and attachment factors.

(i) Primary Culture

Dorsal root ganglia (DRG) were dissected from E14 embryo or adult Sprague Dawley rats and connective tissue was removed under a dissecting microscope. Clean DRGs were incubated with collagenase/dispase (Boehringer Mannheim) at a concentration of 0.3% for embryonic and 5% for adult DRGs for 45 minutes. Then, the DRGs were dispersed by gentle pippetting with a 1 ml Pipettman™. The dispersed cells were collected by centrifugation (1000 rpm, 5 min), washed 3× with F12/DMEM and plated on laminin coated dishes in F12/DMEM supplemented with 7F: recombinant human insulin (5 µg/ml), transferrin (10 µg/ml), progesterone ($2\times10^{-8}$M), bovine pituitary extract (Roberts et al., *Amer. J. Physiol: Lung Cell. & Molec. Physiol.*, 3:415–425 [1990]) (10 µl/ml), recombinant heregulin (3 mM, HRG-$\beta1_{177-244}$) (Sliwkowski et al., supra), forskolin (5 µM) and α-tocopherol (5 µg/ml). Schwann cells grew to a confluent monolayer after 4 days for embryonic, and 7 days for adult cells.

Cells from the primary cultures grown on the laminin substrate were passaged every 4 days at a 1:4 split ratio onto laminin-coated dishes in medium supplemented with progesterone, insulin, α-tocopherol, heregulin, forskolin, and transferrin, as well as bovine pituitary extract. The rapid growth seen initially continued until the eight subculture (1 6th population doubling). At this point both the adult and embryonic cultures "paused" in their growth. This consisted of a period of 7–9 days during which the cultures were viable but did not divide. At the end of this period all cells in the culture, including replicate cultures carded separately started to divide again and continued at the initial rapid doubling time through more than 30 subcultures. There was no die-off or selection for a resistant subpopulation such as is typically seen in "crisis" or senescence. This pause was a repeatable phenomenon when new primary cultures were started in the same manner. Neither conditioned medium from later passages, extra vitamins or nutrients nor other growth factors would alter this growth pause. However, increasing the heregulin concentration from 1nM to 10 nM delayed the onset of the pause to passage 10 and shortened the duration of the lag. Cultures of adult and embryonic Schwann cells were morphologically very similar and continued to exhibit the bi-polar spindle shaped morphology typical of primary cultures. When stained for the Schwann cell markers GFAP and S-100 protein both adult and embryonic SC cultures showed 100% of the cells staining by the third passage. These lines were designated the normal rat embryonic Schwann cell (nrESC or ESC) and normal rat adult Schwann cell (nrASC or ASC) lines. The ESC was karyotyped after 40 passages in continuous culture and maintained a diploid karyotype. However, freezing and thawing of cells at early passages led to aneuploidy and chromosome aberration. Similar results were seen with the ASC line (ii) Immunohistochemistry Schwann cells were plated in laminin coated chamber slides and grown for 2 days. For NGF receptor immunocytochemistry, live cells were incubated with 4 mg/ml monoclonal anti-NGFr (Boehringer Mannheim; clone 192) in F12/DMEM containing 1% BSA for 4 hours at 4° C., then washed 5× with the same medium and fixed with 4% paraformaldehyde for 30 minutes. For GFAP and S-100 immunocytochemistry, cells were washed with phosphate buffered saline (PBS) and fixed with 4% paraformaldehyde for 30 minutes. Fixed cells were washed 3× with PBS and blocked by incubation with 10% goat serum, 0.1% Triton X-100 in PBS for 2 hours at 37° C. Incubation with polyclonal anti-GFAP (ICN) and anti-S100 (ICN), diluted in PBS with 1% goat serum and 0.1% Triton X-100 according to Distributor's suggestion, was carded out at 4° C. overnight. After 3× washes with PBS, conjugated second antibodies, goat anti-rabbit IgG(H+L) F(ab')2-FITC (Boehringer Mannheim) and goat anti-mouse IgG(H+L) F(ab')$_2$-ohycoerithrin (Boehringer Mannheim), were used to stain the bound primary antibodies. Fluorescence micrographs were taken on a Nikon Microphot FX with epiflourescence. For laminin immunocytochemistry, Schwann cells were grown on poly-D-lysine or in suspension for two passages. The cells were either fixed/n situ or fixed on the slide after cytospin and processed for immunofluorescence as for GFAP and S-100 protein above.

(iii) Matrix Study

Coating of 24 well plates was carded out by incubation with different matrix proteins for 1 hour at room temperature at concentrations of 1:10 dilution for rat tail collagen solution (Collaborative Research Laboratories) and 10 μg/ml for human plasma fibronectin (GIBCO BRL), mouse laminin (GIBCO, BRL) and poly-D-lysine (Boehringer Mannheim). The plates coated with poly-D-lysine or collagen were washed 2× with PBS to remove excess mount of the matrix before use. Dissociated embryonic DRG cells were plated in 24 well plates precoated with different extracellular matrices in 7F medium. Cells were observed and micrographs were taken using a Nikon Diaphot inverted phase contrast microscope. At 96 hours of culture, the cells was dispersed o with a trypsin-EDTA solution and counted with a Coulter™ particle counter.

A marked difference in cell morphology was apparent on the different substrata (laminin, poly-lysine, fibronectin, or collagen). Within 24 hours, cells plated on laminin had migrated away from the tissue clump with the Schwann cells migrating off the neural processes. Far fewer cells migrated onto the polylysine substrate and Schwann cells and neurons remain closely associated in a clump of tissue. By 3 days of culture, even more striking differences were seen in the cultures on different substrates. There was extensive neurite outgrowth in the cultures on poly-lysine and collagen, but few Schwann cells had migrated out from the central clumps of cells and little cell division was seen. On fibronectin-coated plates as well, the Schwann cells and neurons remained in tight clumps with long processes connecting them and little cell replication. In contrast, the cultures on the laminin substrate had undergone extensive replication with rapidly dividing Schwann cells readily apparent. The Schwann cells had migrated away from the neurons and formed a confluent monolayer interspersed with tight clusters of neurons. These neuron clusters then floated off the plate and were lost by the first subculture. Even at this very early stage in primary culture it was clear that the Schwann cells, from both adult and embryonic DRG-s, were rapidly dividing and constituted the majority of the cells in the culture. These cells were then passaged on the laminin substrate, for which the embryonic cells show a strong preference.

A very similar growth pattern was seen in primary cultures derived from adult DRG. Again cells plated on laminin substrates rapidly moved away from the neuronal processes and started to divide while those on other substrates remained more clumped and quiescent. These cells were also carried through multiple passages by subculturing onto laminin. However, they did not show such a strong specificity for the laminin substrate on subsequent passage as the embryonic cells, and would grow well on cells plated with poly-D-lysine as well as laminin.

(iv) Growth Factor Studies

Schwann cells of adult or embryonic origin at indicated passages were plated in laminin coated multiwell plates in F12/DMEM supplemented with 7F with the individual growth factor being studied deleted. This factor was then added at a series of concentrations. The cells were cultured for 96 hours before counting with a Coulter™ counter.

Cells were carded through multiple passage in medium supplemented with mitogens (progesterone, insulin and heregulin), vitamins (α-tocopherol, Vitamin E), iron source (transferrin), as well as forskolin, and bovine pituitary extract. The response of the embryonic and adult cells to these factors was compared. Both ESC and ASC showed a biphasic growth response to the cAMP stimulator, forskolin. The best growth stimulation was seen at about 2.5 μM forskolin in both cell lines (FIGS. 4A and 4B) in the presence of all other growth factors. Heregulin was also a major stimulator of growth under these conditions. FIGS. 5A and 5B compare the response to heregulin of ASC and ESC both at passage 21 of culture. The cells show a half-maximal response at 1–2 nM heregulin. An effect of bovine pituitary extract (BPE) (FIGS. 6A and 6B) is seen in the presence of heregulin and of heregulin in the presence of bovine pituitary extract for both cell lines. Both cell lines are significantly stimulated by as little as 0.125 μl (21 μg total protein) of BPE with a maximum stimulation seen at 2–8 μl. These cells contain the receptors for heregulin as shown by direct competable binding of $^{125}$I-heregulin.

Another major growth stimulator of both cell lines is insulin. The response to insulin, IGF-I and IGF-II is shown in FIGS. 7A–F. ASC cells responded to low levels of both IGF-I and insulin, but not to low levels of IGF-II. In contrast, the ESC cells responded primarily to IGF-II and only showed a minor stimulation by insulin or IGF-II at physiological levels. Both cell lines showed some growth stimulation by very high levels of all three factors.

Laminin substrate was an important part of the culture conditions not only in the primary culture stage as described above, but in subsequent passages where cell attachment and subsequent growth response to the hormones and growth factors was dependent on the presence of a laminin coat.

(v) Myelination Studies

Dorsal root ganglia neurons were isolated from 60–70 day old adult rats. Clean dorsal root ganglia (DRGs) were dissociated with 5% collagenase/dispase at 37° C. Cells were collected by centrifugation (900 rpm, 2 min) and DRG neurons, associated with satellite cells, were enriched by centrifugation through 5% bovine serum albumin (BSA) cushion. The harvested cells were further dissociated with a trypsin solution (GIBCO, BRL) for 30 minutes at 37° C. and pelleted at 900 rpm for 2 minutes. The pellets were resuspended in F12/DMEM and DRG neurons were purified by sedimentation twice through a 1%–3% BSA gradient at unit gravity. The purity of DRG neurons purified by this protocol exceeded 99.9%, as determined by titration in microwell culture and observation for any contaminating Schwann cells. For testing for remyelination, DRG neurons and the established Schwann cell lines were cultured separately or in co-culture in F12/DMEM with 5 ng/ml NT-3 and 15% fetal bovine serum. Culture medium was changed once a week. After the first week of culture, L-ascorbic acid was added at a final concentration of 50 µg/ml every two days. The co-cultures were stained for myelin with SUDAN BLACK™ after 40 days of culture. Myelin associated glycoprotein (MAG) was immunostained by immunocytochemistry. Cultures were incubated with anti-MAG monoclonal antibody (Boehringer Mannheim) for 4 hours at 40° C. and fixed with 4% paraformaldehyde after 5× washes with medium to remove free antibodies. The fixed cells were sequentially washed 3× with PBS, blocked by incubation with 10% goat serum in PBS for 2 hours and then incubated with goat anti-mouse IgG(H+L)-peroxidase conjugates. The specific binding of second antibody was revealed by color reaction of peroxidase with DAB-$H_2O_2$. After 40 days in culture, one could see numerous axons which stained positive for MAG. This suggests that the ESC cells have maintained the ability to myelinate axons.

EXAMPLE 2

Isolating and Culturing Human Schwann Cells (i) Gas6 and Heregulin Production

Using Rse- and Axl-specific antibodies, Rse and Axl receptor tyrosine kinases were detected in human Schwann cells. The ability of gas6 to enhance the proliferation of human Schwann cells was determined.

Human gas6 was produced recombinantly. Gas6 cDNA clones were obtained by polymerase chain reaction cloning from reverse transcribed human brain cDNA. The full-length human gas6 clone was constructed by linking together cDNAs encoding amino acids 1–318 and 319–678. Gas6 cDNAs were obtained by PCR using 1 µg of human fetal brain cDNA (Clontech) as template with Pfu DNA polymerase as described (Mark et al., *J. Biol. Chem.* :267:26166 [1992]). Forward and reverse primers designed to obtain the 5' and 3' portions of hgas6 were:

(5'-GATATCGATCCATGGCCCCTTCGCTCTC [SEQ ID NO: 6];

5'-CATGGATCCTACCGGAAGTCAAACTCAGCTA [SEQ ID NO: 7]) and (5'-GATATCGATGAGTGTGAAGTCCTTGTAC [SEQ ID NO: 8];

5'-GTCGGATCCGACAGAGACTGAGAAGCC [SEQ ID NO: 9]), respectively.

Recombinant gas6 was purified from conditioned media by affinity chromatography. Human fetal kidney 29:3 cells were transiently transfected as described in Mark et al., *J. Biol. Chem.* 267:26166 (1992). After a 4 h incubation, the media was replaced with serum free growth media plus antibiotics and 2 µg/ml Vitamin K. Conditioned media were collected at two and 4 days following transfection. The conditioned media of the transfected cells, but not those of either nontransfected or mock transfected 293 cells, activated binding of $^{125}$I-Rse-IgG (see Mark et al., *J. Biol. Chem.* 269:10720 [1994]). A liter of pooled conditioned media was clarified by centrifugation, diluted with 1 volume of buffer A (50 mM TrisHCl, pH 7.5, 0.1% CHAPS, 5 mM benzamidine), and applied to a 6 ml RESOURCE Q™ column (Pharmacia) previously equilibrated with buffer A. The column was eluted with a 12 column volume gradient of 0 to 0.4M NaCl in buffer A. The active fractions were pooled and diluted with 1 volume buffer A and applied to a Rse-IgG affinity column that was prepared using 2 mg of Rse-IgG per ml EMPHASE™ resin according to the supplier's instructions (Pierce).

The identity of recombinant gas6 was verified by amino terminal sequence. The signal from the glutamic acid residues in this sequence was weak, consistent with γ carboxylation.

Recombinant heregulin-$\beta1_{177-244}$ fragment was produced as described in Holmes et al., *Science*, 256: 1205–1210 (1992).

(ii) Pre-Incubation

Peripheral nerve tissues were obtained at the University of Miami School of Medicine, with appropriate patient consent, as previously described (Levi et al., *J. Neuroscience* 15(2):1329–1340 [1995]). Pieces of peripheral nerve fibers were placed in Belzer's UW solution and shipped to California. Upon receipt, the nerve fibers were washed with fresh F12/DME (1:1) and incubated with 1% collagenase/ dispase solution (Boehringer Mannheim) at 37° C. for 30 minutes. Then, the tissue was gently washed 3× by transferring the tissue to fresh tissue culture medium. The fibers were plated in 100 mm petri dishes in serum free medium supplemented with the following: F12/E)ME (1:1) supplemented with insulin (10 µg/ml), transferrin (10 µg/ml), α-tocopherol (5 µg/ml), recombinant human heregulin-$\beta1_{177-244}$ (10 nmole/L), forskolin (5 µmolar), progesterone ($3 \times 10^{-8}$ molar), and bovine pituitary extract (BPE) prepared as described in Example 1 (3 µl/ml). The Schwann cells were cultured in suspension for 48 hours to allow partial demyelination. The nerve fibers were then pooled by centrifugation at 1000 rpm for 5 minutes and resuspended and dispersed by gentle pipetting.

(iii) Obtaining Primary Cultures

The dispersed Schwann cells were replated on laminin (Gibco BRL) coated tissue culture 48 well multiplates at $8 \times 10^3$ cells/well in defined medium with the addition of aprotinin (25 µg/ml) and chemically defined lipids (Sigma Cat#11905–015; Gibco BRL). These cultures were designated the "primary culture". Medium was changed every 5 days. Confluent cultures of pure Schwann cells could be obtained within 2 weeks. At the first and second passage, cells were removed from the plate using collagenase/dispase (Boerhinger Mannheim), washed with medium containing 3% BSA, and plated as described. The media used were "6F" medium: F12/DME (1:1) supplemented with insulin (10 µg/ml), transferrin (10 µg/ml), α-tocopherol (5 µg/ml), progesterone ($3 \times 10^{-8}$ molar), aprotinin (25 µg/ml) and chemically defined lipids (Sigma Cat#11905–015) (50 µg/ml). 8F medium contains the supplements of 6F medium as well as recombinant human heregulin-$\beta1_{177-244}$ (10 nmole/L) and forskolin (5 µM). The effect of gas6 on Schwann cell survival and proliferation was studied by adding gas6 to either of these culture mediums.

Gas6 stimulates human Schwann cell growth in a dose dependent manner (FIG. 8A) with a significant effect seen at 1 ng/ml (14 pM) and maximal effect with doses over 10 ng/ml. Gas6 alone produces a significant increase in Schwann cell number compared to control medium. In the presence of the cAMP activator, forskolin, the increase in total cell number with gas6 is more pronounced. A synergistic effect is also observed between gas6 and heregulin. G-as6 increased both cell number and thymidine incorporation even in the presence of preferred concentrations of both forskolin and heregulin (FIG. 8B).

In the presence of the preferred concentrations of both heregulin and forskolin, other growth factors previously reported to stimulate Schwann cell growth had no effect (PDGF, FGF-β) or reduced cell number (IL-1α and TGF-β1) (FIG. 8C). Addition of human or bovine protein S at 10 ng–5 μg did not increase Schwann cell number after 5 days of culture. In contrast, gas6 at 30 μg/ml maximally increased the cell number. The combination of gas6 with forskolin and heregulin resulted in maximal cell growth over a 5 day period comparable to that seen in the combination of 6F+forskolin+heregulin+5% FBS.

(iv) Cell Morphology

Gas6 had a marked effect on cell morphology as determined by viewing phase contrast micrographs of human Schwann cells grown in 6F+heregulin; 6F+heregulin+gas6; 8F+gas6; and 8F+10% fetal bovine serum. Micrographs were taken after 96 hours of culture. The Schwann cell grown in the presence of gas6 had processes which are much longer than those seen in cells grown in the presence of heregulin or heregulin with forskolin (FIGS. 10A–C). Mitotic figures were also clearly seen in the 8F+gas6 cultures, even in those cells with the fully developed Schwann cell spindle-shaped morphology. The addition of serum to the 8F cultures altered cell morphology, causing the cells to flatten, spread and eventually become vacuolated (FIG. 10D).

(v) Schwann Cell Markers

Cells were stained by immunofluorescence for the Schwann cell markers GFAP and S 100 protein. Briefly, passage 4 human Schwann cells grown in 8F+gas6 were cultured for 24 hours on laminin coated Chamber slides and fixed in 10% formalin in PBS. Fixed cells were blocked with 10% goat serum and incubated with rabbit anti-GFAP (ICN) and anti-S-100 protein (ICN) at dilutions recommended by the distributor. Specific binding of the primary antibody was stained with goat anti-rabbit IgG (Fab')2-FITC conjugates. Cells were counter-stained with DNA dye propidium iodide. Negative controls were run on WI-38 cells which stained negative. Cells grown showed 100% immunofluorescent staining for the Schwann cell markers GFAP and S 100 protein after 4 subcultures.

(vi) Rse/Axl Receptor Activation

The ability of gas6 to stimulate human Schwann cell proliferation through the Axl-Rse family of tyrosine kinase receptors was investigated. Human Schwann cells were stimulated with 0, 0.01, 0.1 or 1 μg/ml of human gas6 (hgas6) for 15 min at 37° C. incubator. Cell lysates were prepared and immunoprecipitated with rabbit anti-hRseFc fusion protein antibody and rabbit anti-hAxl antibody. Tyrosine phosphorylation ofhRse and hAxl receptor was detected with 4G10 anti-phosphorylation antibody. $10^6$ human Schwann cells were grown to near confluence in defined medium (SF+gas6) and changed to 6F medium 24 hours before experiment. Cells were treated with purified recombinant hgas6 for 15 min in 37° C. incubator and lysed on ice with 1 ml of lysis buffer (20 mM HEPES, pH7.4, 135 mM NaCl, 50 mM NaF, 1 mM sodium vanadate and 1 mM sodium molybdate, 2 mM EDTA and 2 mM EGTA, 10% glycerol, 1% NP40, 1 μM okadaic acid, 1 mM PMSF and 1 mM AEBSF). Cell lysates were clarified by centrifuging at 14000× g 4° C. for 10 min. Immunoprecipitations were performed using 1 μg of rabbit anti-hRseFc fusion protein antibody or 2 μl of rabbit anti-hAxl antiserum raised against the 10 amino acids at the COOH-terminal of hAxl at 4° C. for 2 hrs. Immunocomplex were collected with 10 μl of Protein A SEPHAROSE CL-4B ™ beads. Proteins were separated on Novex 4–12% gradient gel and transferred onto nitrocellulose membrane. Anti-phosphotyrosine immunoblots were performed using 4G10 mouse anti-phosphotyrosine antibody (UBI), goat anti-mouse horseradish peroxidase conjugate and ECL developing kit (Amersham). Addition of human gas6 to human Schwann cells caused autophosphorylation of both Axl and he receptors on tyrosine residue(s). Activation of Axl and Rse could be detected at 1.4–14μM gas6. Such phosphorylation of Axl and Rse was not observed in cultures stimulated with heregulin. Gas6 expression in cultured rat Schwann cells was not detected by northern blot. Furthermore, gas6 activity in rat Schwann cell conditioned medium was not seen. Without being bound by any one theory, it is possible that gas6 is produced by growing axons, or by nearby fibroblast cells (from which gas6 was initially cloned). This activation of Axl-Rse receptors on Schwann cells by gas6 is highly specific, since growth factors known to act via other tyrosine kinase receptors, such as PDGF and FGF, do not increase human Schwann cell proliferation under these defined conditions. The Schwann cell growth factors, GGF/heregulin, acting independently through the erbB receptor family, synergize with gas6 in this study.

(vii) ERK2 Activation

Activation of p42 ERK2 in human Schwann cells following hgas6 treatment was studied. Human Schwann cells were stimulated with hgas6 for 15 rain and cell lysates were prepared. Cell lysates containing equal mount of proteins were run on 8% SDS-PAGE gels. Proteins were transferred onto a nitrocellulose membrane and immunoblotted with C20 mouse anti-ERK1+2 monoclonal antibody (Santa Cruz Biotechnology), goat anti-mouse horseradish peroxidase conjugate and ECL developing kit. Activation of Axl and Rse receptors induced a characteristic gel mobility shift of p42 ERK2, consistent with the activation of ERK2. Activation of ERK2 by growth factor receptors leads to multiple cellular events, including cell proliferation.

We claim:

1. A method for enhancing the survival or proliferation of Schwann cells in cell culture without supporting the growth of fibroblasts, said method comprising culturing the Schwann cells in serum free culture medium, wherein the culture medium comprises a nutrient solution for growing mammalian cells supplemented with a first mitogenic agent which is a Rse/Axl receptor activator and a second mitogenic agent, wherein the first and second mitogenic agents are each present in the culture medium in an amount effective to enhance survival or proliferation of the Schwann cells.

2. The method of claim 1 wherein the Schwann cells are human Schwann cells.

3. The method of claim 1 wherein the Rse/Axl receptor activator is gas6.

4. The method of claim 1 wherein the culturing is performed in the presence of laminin.

5. The method of claim 4 comprising culturing the Schwann cells in a laminin-coated culture plate.

6. The method of claim 1 wherein the second mitogenic agent is an erbB receptor activator.

7. The method of claim 1 wherein the second mitogenic agent is an agent which elevates cAMP levels.

8. The method of claim 7 wherein the agent which elevates cAMP levels is forskolin.

9. The method of claim 1 wherein said culture medium additionally comprises a molecule or composition which provides Fe ions to the Schwann cells, wherein the molecule or composition is present in the culture medium in an amount effective to enhance survival or proliferation of the Schwann cells cultured therein.

10. The method of claim 9 wherein said molecule or composition which provides Fe ions to the Schwann cells is transferrin.

11. The method of claim 1 wherein the second mitogenic agent is insulin or an insulin like growth factor, and the insulin or insulin like growth factor is present in the culture medium in an amount effective to enhance survival or proliferation of Schwann cells cultured therein.

12. The method of claim 1 wherein said culture medium additionally comprises Vitamin E, wherein the concentration of Vitamin E in the culture medium is in the range form 0.1 µg/ml to 100 µg/ml.

13. The method of claim 1 wherein said culture medium additionally comprises a protease inhibitor, wherein the concentration of protease inhibitor in the culture medium is in the range from 1 µg/ml to 500 µg/ml.

14. The method of claim 6 wherein the erbB receptor activator is heregulin.

15. A method for isolating Schwann cells comprising:
   (a) incubating nerve tissue containing the Schwann cells in serum-free culture medium which does not support the growth of fibroblasts, said incubation being for a period of time from about 1 day to about 5 days so that demyelination of the Schwann cells occurs, said culture medium comprising a nutrient solution for growing mammalian cells supplemented with a first mitogenic agent which is a Rse/Axl receptor activator and a second mitogenic agent; and
   (b) culturing the demyelinated Schwann cells in the culture medium of (a).

16. The method of claim 15 wherein step (a) is preceded by a step wherein the nerve tissue is contacted with a protease for a period from about 10 minutes to about 100 minutes.

17. The method of claim 16 wherein the nerve tissue is contacted with collagenase and dispase prior to step (a).

18. The method of claim 15 wherein the culture medium additionally comprises heregulin, insulin and forskolin.

19. The method of claim 15 wherein step (b) comprises culturing the demyelinated Schwann cells in a laminin-coated culture plate.

20. A method for enhancing the survival or proliferation of Schwann cells in cell culture without supporting the growth of fibroblasts, said method comprising culturing the Schwann cells in serum free culture medium, wherein the culture medium comprises a nutrient solution for growing mammalian cells supplemented with an activator of the human Rse receptor, an erbB receptor activator and an agent which elevates cAMP levels, wherein the Rse receptor activator, the erbB receptor activator and the agent which elevates cAMP levels are each present in the culture medium in an amount effective to enhance survival or proliferation of the Schwann cells cultured therein.

21. The method of claim 20 wherein the Rse receptor activator is gas6.

22. The method of claim 21 wherein the concentration of gas6 in the culture medium is in the range from about 0.1 ng/ml to 100 ng/ml.

23. The method of claim 20 wherein the erbB receptor activator is heregulin.

24. The method of claim 23 wherein the heregulin is human heregulin-$\beta 1_{177-244}$ fragment.

25. The method of claim 23 wherein the concentration of heregulin in the culture medium is in the range from about 0.1 nM to 50 nM.

26. The method of claim 20 wherein the agent which elevates cAMP levels is forskolin.

27. The method of claim 26 wherein the concentration of forskolin in the culture medium is in the range from 0.1 µM to 50 µM.

28. The method of claim 20 wherein said culture medium additionally comprises insulin or an insulin like growth factor, wherein the insulin or insulin like growth factor is present in the culture medium in an amount effective to enhance survival or proliferation of Schwann cells cultured therein.

29. The method of claim 20 wherein said culture medium additionally comprises insulin, wherein the concentration of insulin in the culture medium is in the range form 0.1 µg/ml to 200 µg/ml.

30. The method of claim 28 wherein said culture medium additionally comprises a molecule or composition which provides Fe ions to Schwann cells.

31. The method of claim 30 wherein the molecule or composition which provides Fe ions to the Schwann cells is transferrin.

32. The method of claim 30 wherein said culture medium additionally comprises progesterone, wherein the concentration of progesterone in the culture medium is in the range from 0.1 nM to 1000 nM.

33. The method of claim 32 wherein said culture medium additionally comprises Vitamin E, wherein the concentration of Vitamin E in the culture medium is in the range from 0.1 µg/ml to 100 µg/ml.

34. The method of claim 33 wherein said culture medium additionally comprises a protease inhibitor, wherein the concentration of protease inhibitor in the culture medium is in the range form 1 µg/ml to 500 µg/ml.

* * * * *